(12) United States Patent
Li et al.

(10) Patent No.: US 8,889,876 B2
(45) Date of Patent: Nov. 18, 2014

(54) HISTONE DEACETYLASE INHIBITORS AND USES THEREOF

(75) Inventors: Jianqi Li, Shanghai (CN); Juan Feng, Shanghai (CN); Wangping Cai, Jiangsu (CN)

(73) Assignee: Jiangsu Hengyi Pharmaceutical Co., Ltd., Nanjing, Jiangsu Province (CN)

( * ) Notice: Subject to any disclaimer, the term of this patent is extended or adjusted under 35 U.S.C. 154(b) by 553 days.

(21) Appl. No.: 13/000,186

(22) PCT Filed: Jun. 9, 2009

(86) PCT No.: PCT/CN2009/072186
§ 371 (c)(1),
(2), (4) Date: Mar. 9, 2011

(87) PCT Pub. No.: WO2009/152735
PCT Pub. Date: Dec. 23, 2009

(65) Prior Publication Data
US 2011/0152323 A1 Jun. 23, 2011

(30) Foreign Application Priority Data
Jun. 20, 2008 (CN) .......................... 2008 1 0043526

(51) Int. Cl.
| | |
|---|---|
| A61K 31/44 | (2006.01) |
| C07D 213/76 | (2006.01) |
| A61K 31/165 | (2006.01) |
| A61K 31/4406 | (2006.01) |
| C07D 213/73 | (2006.01) |
| C07D 213/75 | (2006.01) |

(52) U.S. Cl.
CPC ............ *A61K 31/165* (2013.01); *C07D 213/76* (2013.01); *A61K 31/44* (2013.01); *A61K 31/4406* (2013.01); *C07D 213/73* (2013.01); *C07D 213/75* (2013.01)
USPC ............................ 546/308; 514/352; 514/183

(58) Field of Classification Search
USPC .......................................................... 546/308
See application file for complete search history.

(56) References Cited

U.S. PATENT DOCUMENTS

| | | |
|---|---|---|
| 6,174,905 B1 | 1/2001 | Suzuki et al. |
| 2004/0058903 A1* | 3/2004 | Takasugi et al. ........... 514/210.2 |

FOREIGN PATENT DOCUMENTS

| | | |
|---|---|---|
| WO | WO 03/035602 A1 * | 5/2003 |
| WO | 2007017728 | 2/2007 |

OTHER PUBLICATIONS

Feng et al., Synthesis and anti-tumor activities of N-substituted benzamide derivatives, 2009, Yaoxue Xuebao, 44(6), 603-608—CAS React Summary only, including abstract and reactions.*
STN Entry for WO 03/035602, 2 pages entered into STN 2005, accessed Dec. 7, 2013.*
STN Entry for Lu et al. (CN 1513839), 2 pages, entered into STN in 2005, accessed Dec. 7, 2013.*
International Search Report for PCT/CN2009/072186 dated Aug. 9, 2009.
English Abstract for CN1513839, 2004.
English Abstract for JP11335375, 1999.

* cited by examiner

*Primary Examiner* — Jeffrey S. Lundgren
*Assistant Examiner* — Meghan Finn
(74) *Attorney, Agent, or Firm* — Andrus Intellectual Property Law, LLP

(57) ABSTRACT

The present invention discloses a group of histone deacetylase inhibitors and use thereof. The histone deacetylase inhibitors are useful in the treatment of malignant tumors and the diseases associated with differentiation and proliferation. The histone deacetylase inhibitors are the compounds represented by the following formula or salts thereof:

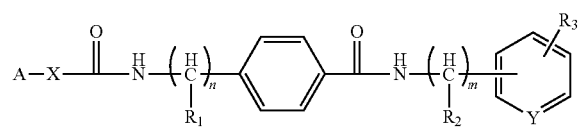

3 Claims, No Drawings

US 8,889,876 B2

HISTONE DEACETYLASE INHIBITORS AND USES THEREOF

CROSS-REFERENCE TO RELATED APPLICATIONS

This application is the U.S. national stage application of International Application PCT/CN2009/072186, filed Jun. 9, 2009, which international application was published on Dec. 23, 2009, as International Publication WO2009/152735A1 in the Chinese language. The International Application claims priority of Chinese Patent Application No. 200810043526.2 filed Jun. 20, 2008.

TECHNICAL FIELD

The present invention relates to use of a type of histone deacetylase inhibitors and the type of small molecular compounds in treating malignant tumors and diseases associated with differentiation and proliferation.

BACKGROUND

The histone acetylation and deacetylation of chromatin is one of the critical steps in modulating gene expression, whereas abnormal gene expression is the molecular biological basis of occurrence of tumors and some inherited and metabolic disorders. The acetylation degree of histone is coordinately controlled by histone acetylase (HAT) and histone deacetylase (HDAC). When HDAC are in over expression and recruited by transcription factor, it will result in abnormal inhibition of particular genes, thereby the occurrence of tumors and other diseases. According to the following documents, the activity of HDAC is related to the occurrence of cancers, immune disorders, and some psychiatric and cardiovascular disorders. Experiments show that HDAC inhibitors increase the acetylation level of histone of chromatin, thereby resulting in activated expression of particular genes and the corresponding terminal differentiation of cells and apoptosis of cancer cells. Primary clinical study shows that humans can obtain a high acetylation level of histone safely by inhibiting HDAC activity. Therefore, HDAC has become the latest and hottest target in the research of chemotherapeutic drugs of tumors.

REFERENCE DOCUMENTS (1) *British Journal of Pharmacology* (2007), 150 (7), 862-872.
(2) *Bioorganic & Medicinal Chemistry* (2008), 16 (9), 5254-5265.
(3) WO 2003083067
(4) *Proceedings of the National Academy of Sciences of the United States of America* (2006), 103 (5), 1587-1592.
(5) *Journal of biomedicine & biotechnology* 2006 (2), 13474.

Histone deacetylase is a large family and can be deviced into three groups based on the identity of the sequences: the first group includes rpd3 similar proteins such as HDAC1, HDAC2, HDAC3, HDAC8, HDAC11, which type of enzymes contain about 400-500 amino acids, mailly present in cell nucleus; the second group includes yeast HDA1 similar proteins such as HDAC4, HDAC5, HDAC6, HDAC7, HDAC9, and HDAC10, which are proteins containing about 1000 amino acids, wherein the catalytic sites are mainly at C-terminal of peptide, but wherein HDAC6 further contains a duplicated catalytic center at N-terminal; the third group includes yeast SIR-2 similar proteins, which contain nicotinamide adenine dinucleotide (NAD+)-dependent activity. Most of the above subgroups have structural similarity and present from prokaryotes to eukaryotes, whereas most of them are not for qualifying study yet.

Several types of histone deacetylase inhibitors have been reported in foreign countries, which are divided into the following groups based on their chemical structures:
(1) Hydroxamic acids, such as trichostatin (TSA), Suberolanilide hydroxamic acid (SAHA);
(2) cyclopeptides such as Apicidin;
(3) benzamides such as MS-275;
(4) short-chain and aromatic fatty acids such as sodium butyrate;
(5) heterocycle compounds such as Depudecina.

In the above various inhibitors, the first type, i.e., the hydroxamic acids, belongs to reversible HDAC inhibitors, represented by SAHA, and is the only commercially available histone deacetylase inhibitor. It is approved by the Food and Drug Administration of U.S. on Oct. 6, 2006 for the treatment of metastatic cutaneous T-cell lymphoma (CTCL) that cannot be cured, or is deteriorated or recrudescence during or after using of other drugs. The second type, i.e., cyclopeptides, is HDAC inhibitors having complicated structures, which also has the structural features of general HDAC inhibitors, such as, a large ring including hydrophobic amino acid as identifying region of enzyme surface and linking groups and functional groups bonding to meta ions. The third type, i.e., the benzamides, of which the in votro effect is worse than that of the first and second types but the in vivo effect is good, and which has strong selectivity, is the focus of the current study. The representative, MS-275, is at the stage II clinical experiment. The fourth type generally has a weak inhibition activity, and has to combined and tested with other drugs for having strong actions. The last type does not have structural features of general HDAC inhibitors but can inhibit HDAC.

Since structures of histone deacetylase subtypes are very similar, most of the existing histone deacetylase inhibitors do not have subtype selectivity. Inhibiting a plurality of subtypes simultaneously generally causes some side toxic reaction, which affects formulation of medicaments. Therefore, to design and synthesize high selectivity histone deacetylase inhibitors to obtain a novel anti-malignant tumor agent having good effect, less side toxic effect and being safe is the focuse and technical point of the research of the field.

CONTENT OF THE INVENTION

One of the technical problems to be solved by the present application is to disclose a group of histone deacetylase inhibitors to meet the requirements of clinical applications.

The second technical problem to be solved by the present application is to disclose use of the histone deacetylase inhibitors in manufacture of a medicament for treating malignant tumors and diseases associated with differentiation and proliferation.

The histone deacetylase inhibitor of the present application is a compound represented by the following structural formula:

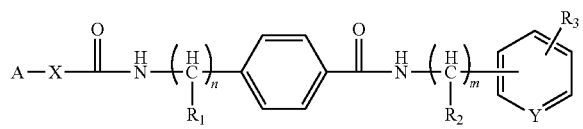

wherein, A is an aromatic ring or a heterocycle containing 1 to 4 substituents, wherein the substituents are halogen, amino, hydroxy, nitro, cyano, alkyl having 1 to 4 carbon atoms, alkoxy having 1 to 4 carbon atoms, aminoalkyl having 1 to 4 carbon atoms, alkylamino having 1 to 4 carbon atoms, acyl having 2 to 4 carbon atoms, acylamino having 2 to 4 carbon atoms, thioalkyl having 1 to 4 carbon atoms, trifluoromethyl, carboxyl having 1 to 4 carbon atoms, alkoxycarbonyl having 1 to 4 carbon atoms, phenyl or heterocycle substituents;

X is a covalent bond, alkylene having 1 to 4 carbon atoms, or a linear or cyclic structure containing —O—, —S—, —NH—, or a combination of the linear structure and the cyclic structure;

$R_1$, $R_2$ are hydrogen, $C_1$-$C_5$ alkyl, $C_5$ or $C_6$ aliphatic ring, phenyl or substituted phenyl, $R_3$ is hydrogen, —OH or —NH$_2$;

Y is N, C;

m=0, 1, 2, 3, and when Y is C, m≠0;

n=0, 1, 2, 3;

or a salt thereof.

The "aromatic ring" in the present invention has aromatic cyclic structure and can contain substituents;

The said substituted phenyl is a phenyl ring having 1 to 4 substituents, and the substituents can be halogen, hydroxy, nitro, cyano, alkoxy, alkyl having 1 to 4 carbon atoms or amino groups;

The said "heterocycle" refers to a saturated or unsaturated heterocycle containing one or more heteroatoms (nitrogen, oxygen, sulfur), such as tetrahydropyrrole, dihydropyrazole, piperidine, morpholine, imidazole or pyridine, etc.;

The said halogen is preferably fluorine, chlorine, bromine or iodine;

The said alkyl having 1 to 4 carbon atoms is preferably methyl, ethyl, n-propyl, isopropyl, n-butyl, isobutyl or tert-butyl, etc.;

The said alkoxy having 1 to 4 carbon atoms is preferably methoxy, ethoxy, n-propoxy, isopropoxy, n-butoxy or isobutoxy, etc.;

The said aminoalkyl having 1 to 4 carbon atoms is preferably aminoethyl, 1-aminopropyl or 2-aminopropyl, etc.;

The said alkylamino having 1 to 4 carbon atoms is preferably N-methyl amino, N-ethyl amino or N-isopropyl amino;

The said acyl having 2 to 4 carbon atoms is preferably acetyl, propionyl or isobutyryl, etc., The said acylamino having 2 to 4 carbon atoms is preferably acetylamino, propionylamino, butyrylamino or isobutyrylamino, etc.;

The said thioalkyl having 2 to 4 carbon atoms is preferably methylthio, ethylthio or propylthio, etc.;

The said alkylene having 1 to 4 carbon atoms is preferably methylene or ethylene, etc.:

The said salt is hydrochloride, hydrobromide, sulfate, trifluoroacetate or methanesulfonate, the said salt contains 0.5-3 molecules of crystal water.

The preferably compounds include:

V-1 N-(2-aminobenzyl)-4-[(3-pyridylmethoxyacyl)aminomethyl]benzamide;

V-2 N-(2-pyridyl)-4-[(3-pyridylmethoxyacyl)aminomethyl]benzamide;

V-3 N-(3-pyridyl)-4-[(3-pyridylmethoxyacyl)aminomethyl]benzamide;

V-4 N-(2-amino-3-pyridyl)-4-[(3-pyridylmethoxyacyl)aminomethyl]benzamide;

V-5 N-(2-amino-4-pyridyl)-4-[(3-pyridylmethoxyacyl)aminomethyl]benzamide;

V-6 N-[1-(2-aminophenyl)ethyl]-4-[(3-pyridylmethoxyacyl)aminomethyl]benzamide;

V-7 N-(2-amino-4-pyridyl)-4-(benzyloxyacylaminomethyl)benzamide;

V-8 N-(2-amino-3-pyridyl)-4-(benzyloxyacylaminomethyl)benzamide;

V-9 N-(2-amino-3-pyridyl)-4-[(4-methylbenzyloxyacyl)aminomethyl]benzamide;

V-10 N-(2-amino-4-pyridyl)-4-[(4-methylbenzyloxyacyl)aminomethyl]benzamide;

V-11 N-(2-amino-3-pyridyl)-4-[(4-methoxybenzyloxyacyl)aminomethyl]benzamide;

V-12 N-(2-amino-4-pyridyl)-4-[(4-methoxybenzyloxyacyl)aminomethyl]benzamide;

V-13 N-(2-amino-3-pyridyl)-4-[(3,4,5-trimethoxybenzyloxyacyl)aminomethyl]benzamide;

V-14 N-(2-amino-4-pyridyl)-4-[(3,4,5-trimethoxybenzyloxyacyl)aminomethyl]benzamide;

V-15 N-(2-amino-3-pyridyl)-4-[(4-nitrobenzyloxyacyl)aminomethyl]benzamide;

V-16 N-(2-amino-3-pyridyl)-4-[(4-aminobenzyloxyacyl)aminomethyl]benzamide;

V-17 N-(2-amino-4-pyridyl)-4-[(4-nitrobenzyloxyacyl)aminomethyl]benzamide;

V-18 N-(2-amino-4-pyridyl)-4-[(4-aminobenzyloxyacyl)aminomethyl]benzamide;

V-19 N-(2-amino-3-pyridyl)-4-[(4-fluorobenzyloxyacyl)aminomethyl]benzamide;

V-20 N-(2-amino-4-pyridyl)-4-[(4-fluorobenzyloxyacyl)aminomethyl]benzamide;

V-21 N-(2-amino-3-pyridyl)-4-[(4-phenylbenzyloxyacyl)aminomethyl]benzamide;

V-22 N-(2-amino-4-pyridyl)-4-[(4-phenylbenzyloxyacyl)aminomethyl]benzamide;

V-23 N-(2-amino-3-pyridyl)-4-[(2-naphthylmethoxyacyl)aminomethyl)benzamide;

V-24 N-(2-amino-4-pyridyl)-4-[(2-naphthylmethoxyacyl)aminomethyl]benzamide;

V-25 N-(2-amino-3-pyridyl)-4-(cinnamoylaminomethyl)benzamide;

V-26 N-(2-amino-4-pyridyl)-4-(cinnamoylaminomethyl)benzamide;

V-27 N-(2-amino-3-pyridyl)-4-[(4-methylcinnamoyl)aminomethyl]benzamide;

V-28 N-(2-amino-4-pyridyl)-4-[(4-methylcinnamoyl)aminomethyl]benzamide;

V-29 N-(2-amino-3-pyridyl)-4-[(4-methoxycinnamoyl)aminomethyl]benzamide;

V-30 N-(2-amino-4-pyridyl)-4-[(4-methoxycinnamoyl)aminomethyl]benzamide;

V-31 N-(2-hydroxy-5-pyridyl)-4-[(3,4,5-trimethoxycinnamoyl)aminomethyl]benzamide;

V-32 N-(2-pyridyl)-4-[(3,4,5-trimethoxycinnamoyl)aminomethyl]benzamide;

V-33 N-(3-pyridyl)-4-[(3,4,5-trimethoxycinnamoyl)aminomethyl]benzamide;

V-34 N-(2-amino-3-pyridyl)-4-[(3,4,5-trimethoxycinnamoyl)aminomethyl]benzamide;

V-35 N-(2-amino-4-pyridyl)-4-[(3,4,5-trimethoxycinnamoyl)aminomethyl]benzamide;

V-36 N-(2-amino-3-pyridyl)-4-[(4-nitrocinnamoyl)aminomethyl]benzamide;

V-37 N-(2-amino-4-pyridyl)-4-[(4-aminocinnamoyl)aminomethyl]benzamide;

V-38 N-(2-amino-4-pyridyl)-4-[(4-nitrocinnamoyl)aminomethyl]benzamide;

V-39 N-(2-amino-4-pyridyl)-4-[(4-aminocinnamoyl)aminomethyl]benzamide;

V-40 N-(2-amino-3-pyridyl)-4-[(4-fluorocinnamoyl)aminomethyl]benzamide;

V-41 N-(2-amino-4-pyridyl)-4-[(4-fluorocinnamoyl)aminomethyl]benzamide;

V-42 N-(2-amino-3-pyridyl)-4-[(3-pyridylacryloyl)aminomethyl]benzamide;
V-43 N-(2-amino-4-pyridyl)-4-[(3-pyridylacryloyl)aminomethyl]benzamide;
V-44 N-(2-amino-3-pyridyl)-4-(4-phenylcinnamoylaminomethyl)benzamide;
V-45 N-(2-amino-4-pyridyl)-4-(4-phenylcinnamoylaminomethyl)benzamide;
V-46 N-(2-amino-3-pyridyl)-4-(2-naphthylacryloylaminomethyl)benzamide;
V-47 N-(2-amino-4-pyridyl)-4-(2-naphthylacryloylaminomethyl)benzamide;
V-48 N-(2-amino-3-pyridyl)-4-[(3-phenylpropionyl)aminomethyl]benzamide;
V-49 N-(2-amino-4-pyridyl)-4-[(3-phenylpropionyl)aminomethyl]benzamide;
V-50 N-(2-amino-3-pyridyl)-4-[3-(4-methylphenyl)propionylaminomethyl]benzamide;
V-51 N-(2-amino-4-pyridyl)-4-[3-(4-methylphenyl)propionylaminomethyl]benzamide;
V-52 N-(2-amino-3-pyridyl)-4-[3-(4-methoxyphenyl)propionylaminomethyl]benzamide;
V-53 N-(2-amino-4-pyridyl)-4-[3-(4-methoxyphenyl)propionylaminomethyl]benzamide;
V-54 N-(2-amino-3-pyridyl)-4-[3-(3,4,5-methoxyphenyl)propionylaminomethyl]benzamide;
V-55 N-(2-amino-4-pyridyl)-4-[3-(3,4,5-methoxyphenyl)propionylaminomethyl]benzamide;
V-56 N-(2-amino-3-pyridyl)-4-[3-(4-nitrophenyl)propionylaminomethyl]benzamide;
V-57 N-(2-amino-3-pyridyl)-4-[3-(4-aminophenyl)propionylaminomethyl]benzamide;
V-58 N-(2-amino-4-pyridyl)-4-[3-(4-nitrophenyl)propionylaminomethyl]benzamide;
V-59 N-(2-amino-4-pyridyl)-4-[3-(4-aminophenyl)propionylaminomethyl]benzamide;
V-60 N-(2-amino-3-pyridyl)-4-[3-(4-fluorophenyl)propionylaminomethyl]benzamide;
V-61 N-(2-amino-4-pyridyl)-4-[3-(4-fluorophenyl)propionylaminomethyl]benzamide;
V-62 N-(2-amino-3-pyridyl)-4-[3-(3-pyridyl)propionylaminomethyl]benzamide;
V-63 N-(2-amino-4-pyridyl)-4-[3-(3-pyridyl)propionylaminomethyl]benzamide;
V-64 N-(2-amino-3-pyridyl)-4-[3-(4-phenyl)phenylpropionylaminomethyl]benzamide;
V-65 N-(2-amino-4-pyridyl)-4-[3-(4-phenyl)phenylpropionylaminomethyl]benzamide;
V-66 N-(2-amino-3-pyridyl)-4-[3-(2-naphthyl)propionylaminomethyl]benzamide;
V-67 N-(2-amino-4-pyridyl)-4-[3-(2-naphthyl)propionylaminomethyl]benzamide;
V-68 N-(2-amino-3-pyridyl)-4-[(3-benzylureido)methyl]benzamide;
V-69 N-(2-amino-4-pyridyl)-4-[(3-benzylureido)methyl]benzamide;
V-70 N-(2-amino-3-pyridyl)-4-[(4-methoxybenzylureido)methyl]benzamide;
V-71 N-(2-amino-4-pyridyl)-4-[(4-methylbenzylureido)methyl]benzamide;
V-72 N-(2-amino-3-pyridyl)-4-[(4-methoxybenzylureido)methyl]benzamide;
V-73 N-(2-amino-4-pyridyl)-4-[(4-methoxybenzylureido)methyl]benzamide;
V-74 N-(2-amino-3-pyridyl)-4-[(3,4,5-trimethoxybenzylureido)methyl]benzamide;
V-75 N-(2-amino-4-pyridyl)-4-[(3,4,5-trimethoxybenzylureido)methyl]benzamide;
V-76 N-(2-amino-3-pyridyl)-4-[(4-nitrobenzylureido)methyl]benzamide;
V-77 N-(2-amino-3-pyridyl)-4-[(4-aminobenzylureido)methyl]benzamide;
V-78 N-(2-amino-4-pyridyl)-4-[(4-nitrobenzylureido)methyl]benzamide;
V-79 N-(2-amino-4-pyridyl)-4-[(4-aminobenzylureido)methyl]benzamide;
V-80 N-(2-amino-3-pyridyl)-4-[(4-fluorobenzylureido)methyl]benzamide;
V-81 N-(2-amino-4-pyridyl)-4-[(4-fluorobenzylureido)methyl]benzamide;
V-82 N-(2-amino-3-pyridyl)-4-[(3-pyridylmethylureido)methyl]benzamide;
V-83 N-(2-amino-4-pyridyl)-4-[(3-pyridylmethylureido)methyl]benzamide;
V-84 N-(2-amino-3-pyridyl)-4-[(3-biphenylmethylureido)methyl]benzamide;
V-85 N-(2-amino-4-pyridyl)-4-[(3-biphenylmethylureido)methyl]benzamide;
V-86 N-(2-amino-3-pyridyl)-4-[3-(2-naphthylmethyl)ureidomethyl]benzamide;
V-87 N-(2-amino-4-pyridyl)-4-[3-(2-naphthylmethyl)ureidomethyl]benzamide;
V-88 N-(2-amino-4-pyridyl)-4-[(3,4,5-trimethoxycinnamoyl)-1-aminoethyl]benzamide;
V-89 N-(2-amino-4-pyridyl)-4-[phenylpiperazinylacyl)aminomethyl]benzamide or
V-90 N-(2-amino-4-pyridyl)-4-[(3,4,5-trimethoxycinnamoyl)-2-phenylethylamino]benzamide;
V-91 N-(2-amino-3-pyridyl)-4-[(3-methoxycinnamoyl)aminomethyl]benzamide;
V-92 N-(2-amino-4-pyridyl)-4-[(3-methoxycinnamoyl)aminomethyl]benzamide;
V-93 N-(2-amino-3-pyridyl)-4-[(3,4-dimethoxycinnamoyl)aminomethyl]benzamide;
V-94 N-(2-amino-4-pyridyl)-4-[(3,4-dimethoxycinnamoyl)aminomethyl]benzamide;
V-95 N-(2-amino-4-pyridyl)-4-[(3-methoxybenzyloxyacyl)aminomethyl]benzamide;
V-96 N-(2-amino-4-pyridyl)-4-[(3,4-dimethoxybenzyloxyacyl)aminomethyl]benzamide.

The structures are given as follow:

| No. | Structures |
|---|---|
| V-1 | 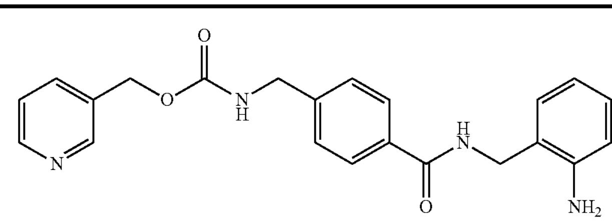 |

| No. | Structures |
|---|---|
| V-2 | 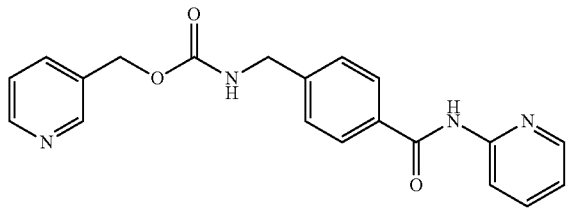 [SMILES: O=C(NCc1ccc(C(=O)Nc2ccccn2)cc1)OCc1cccnc1] |
| V-3 | 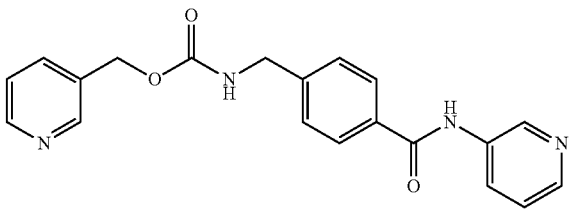 [SMILES: O=C(NCc1ccc(C(=O)Nc2cccnc2)cc1)OCc1cccnc1] |
| V-4 | 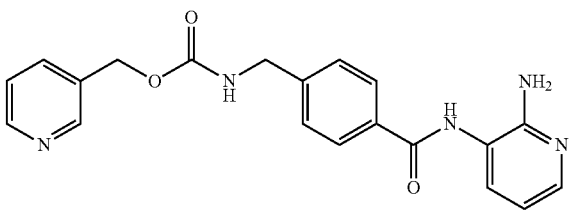 [SMILES: Nc1ncccc1NC(=O)c1ccc(CNC(=O)OCc2cccnc2)cc1] |
| V-5 | 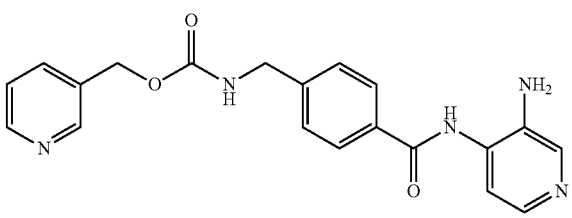 [SMILES: Nc1cnccc1NC(=O)c1ccc(CNC(=O)OCc2cccnc2)cc1] |
| V-6 | 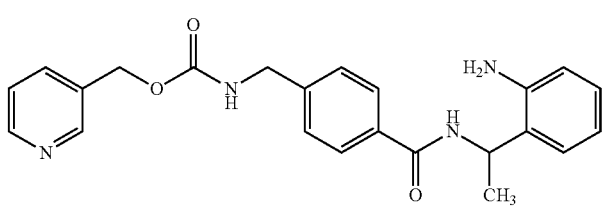 [SMILES: CC(NC(=O)c1ccc(CNC(=O)OCc2cccnc2)cc1)c1ccccc1N] |
| V-7 | 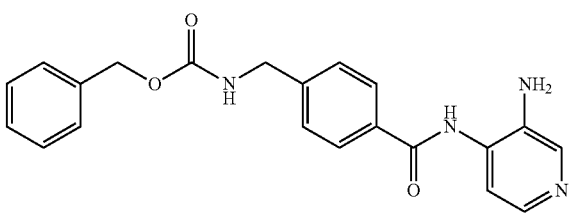 [SMILES: Nc1cnccc1NC(=O)c1ccc(CNC(=O)OCc2ccccc2)cc1] |
| V-8 | 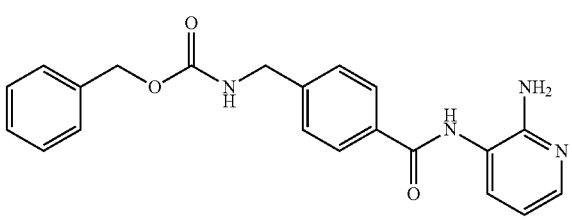 [SMILES: Nc1ncccc1NC(=O)c1ccc(CNC(=O)OCc2ccccc2)cc1] |

-continued

| No. | Structures |
|---|---|
| V-9 | 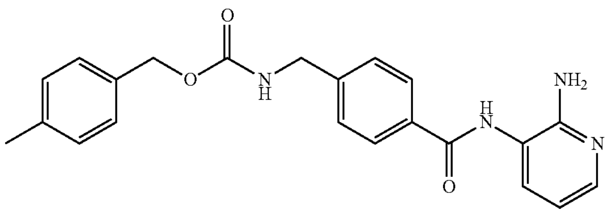 [SMILES: Cc1ccc(COC(=O)NCc2ccc(C(=O)Nc3cccnc3N)cc2)cc1] |
| V-10 | 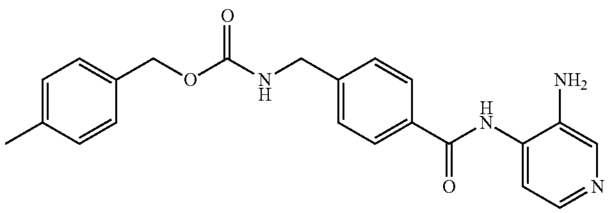 |
| V-11 | 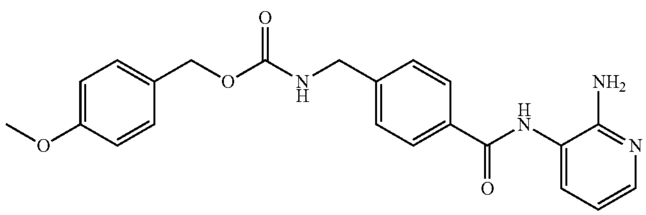 [SMILES: COc1ccc(COC(=O)NCc2ccc(C(=O)Nc3cccnc3N)cc2)cc1] |
| V-12 | 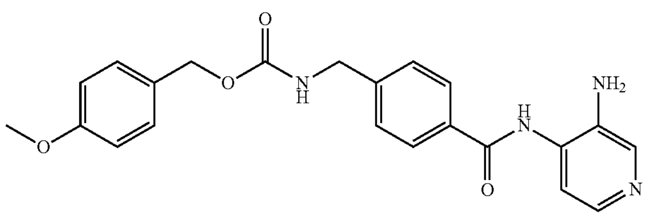 [SMILES: COc1ccc(COC(=O)NCc2ccc(C(=O)Nc3ccncc3N)cc2)cc1] |
| V-13 | 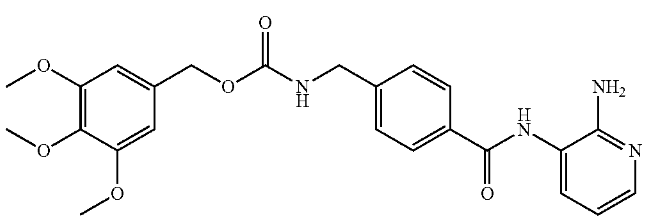 [SMILES: COc1cc(COC(=O)NCc2ccc(C(=O)Nc3cccnc3N)cc2)cc(OC)c1OC] |
| V-14 | 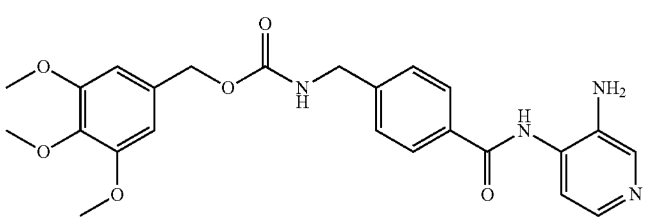 [SMILES: COc1cc(COC(=O)NCc2ccc(C(=O)Nc3ccncc3N)cc2)cc(OC)c1OC] |
| V-15 | 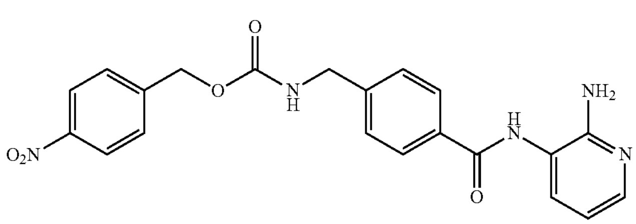 |

| No. | Structures |
|---|---|
| V-16 | 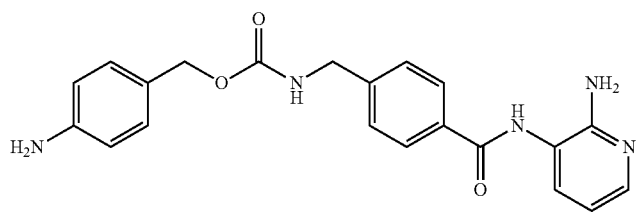 [SMILES: Nc1ncccc1NC(=O)c1ccc(CNC(=O)OCc2ccc([N+](=O)[O-])cc2)cc1] |
| V-17 | 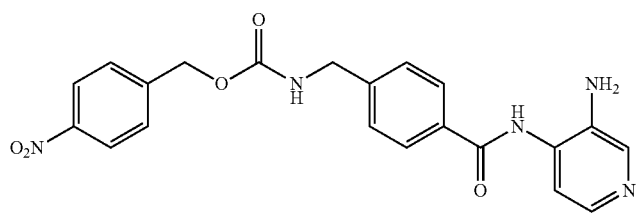 [SMILES: Nc1cnccc1NC(=O)c1ccc(CNC(=O)OCc2ccc([N+](=O)[O-])cc2)cc1] |
| V-18 | 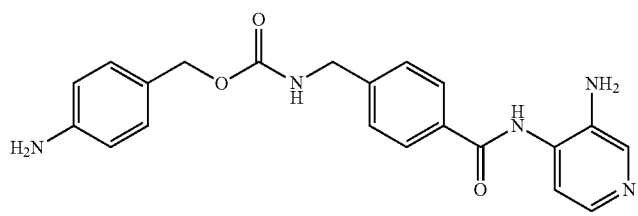 |
| V-19 | 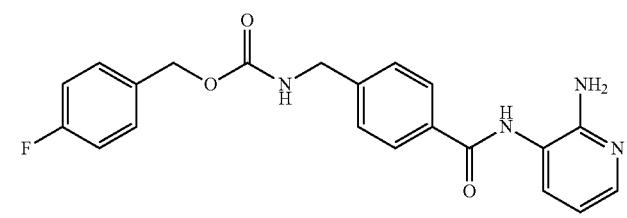 [SMILES: Nc1ncccc1NC(=O)c1ccc(CNC(=O)OCc2ccc(F)cc2)cc1] |
| V-20 | 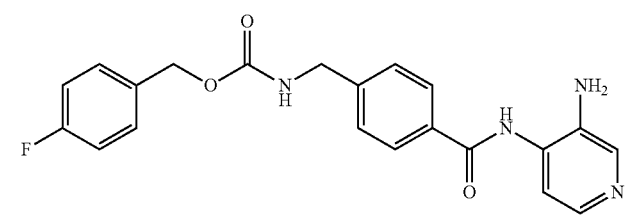 [SMILES: Nc1cnccc1NC(=O)c1ccc(CNC(=O)OCc2ccc(F)cc2)cc1] |
| V-21 | 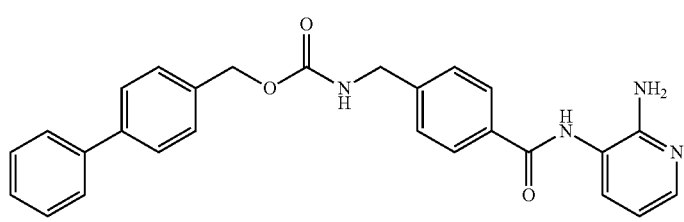 |
| V-22 | 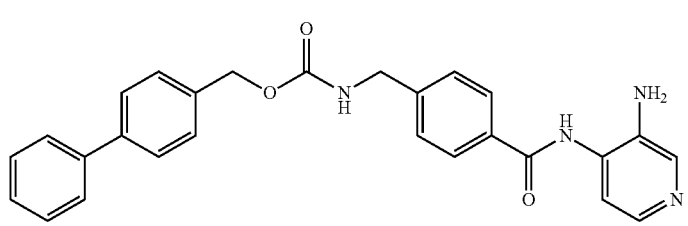 [SMILES: Nc1cnccc1NC(=O)c1ccc(CNC(=O)OCc2ccc(-c3ccccc3)cc2)cc1] |

-continued
| No. | Structures |
|---|---|
| V-23 | 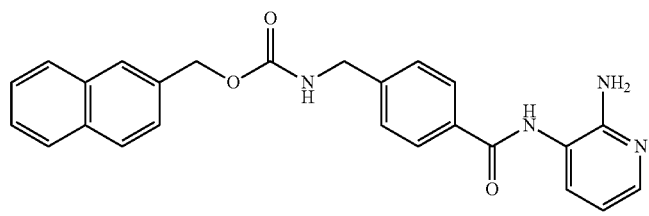 |
| V-24 | 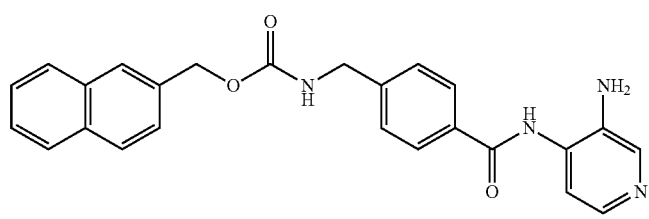 [SMILES: Nc1cnccc1NC(=O)c1ccc(CNC(=O)OCc2ccc3ccccc3c2)cc1] |
| V-25 | 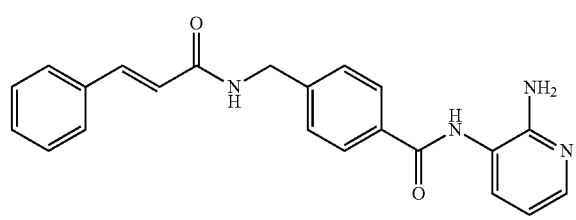 [SMILES: Nc1ncccc1NC(=O)c1ccc(CNC(=O)/C=C/c2ccccc2)cc1] |
| V-26 | 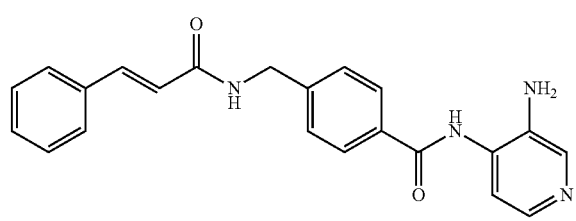 |
| V-27 | 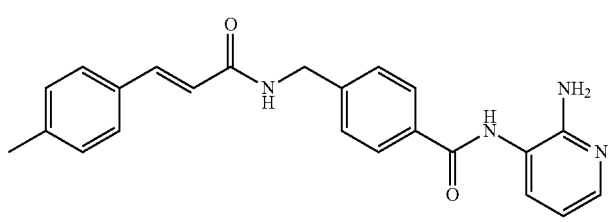 [SMILES: Cc1ccc(/C=C/C(=O)NCc2ccc(C(=O)Nc3cccnc3N)cc2)cc1] |
| V-28 | 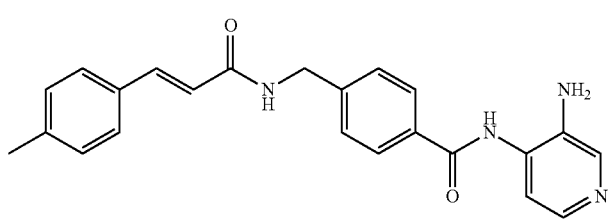 [SMILES: Cc1ccc(/C=C/C(=O)NCc2ccc(C(=O)Nc3ccncc3N)cc2)cc1] |
| V-29 | 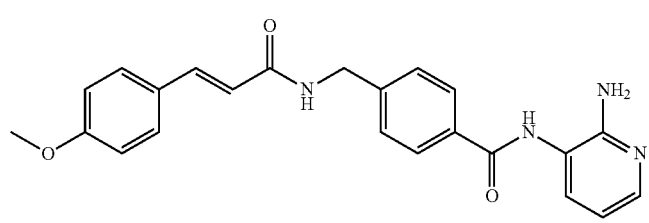 [SMILES: COc1ccc(/C=C/C(=O)NCc2ccc(C(=O)Nc3cccnc3N)cc2)cc1] |

-continued

| No. | Structures |
|---|---|
| V-30 | 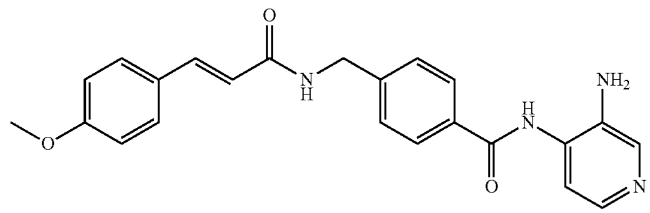 [SMILES: COc1ccc(/C=C/C(=O)NCc2ccc(C(=O)Nc3ccncc3N)cc2)cc1] |
| V-31 | 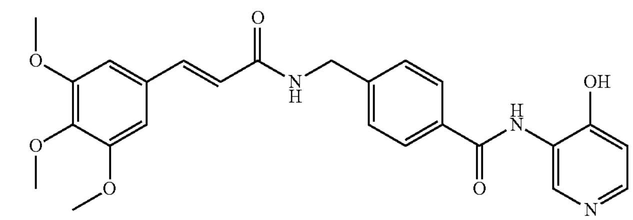 [SMILES: COc1cc(/C=C/C(=O)NCc2ccc(C(=O)Nc3cnccc3O)cc2)cc(OC)c1OC] |
| V-32 | 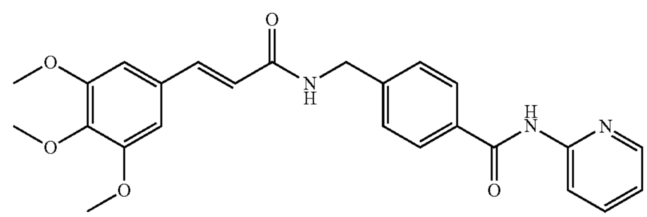 [SMILES: COc1cc(/C=C/C(=O)NCc2ccc(C(=O)Nc3ccccn3)cc2)cc(OC)c1OC] |
| V-33 | 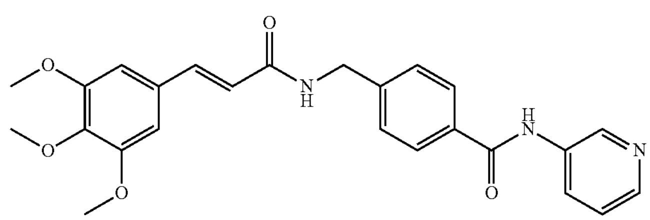 [SMILES: COc1cc(/C=C/C(=O)NCc2ccc(C(=O)Nc3cccnc3)cc2)cc(OC)c1OC] |
| V-34 | 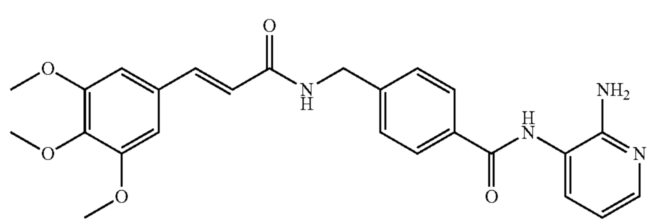 [SMILES: COc1cc(/C=C/C(=O)NCc2ccc(C(=O)Nc3cccnc3N)cc2)cc(OC)c1OC] |
| V-35 | 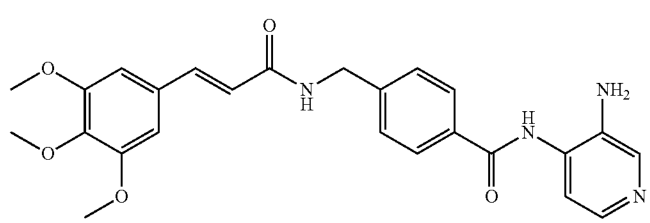 [SMILES: COc1cc(/C=C/C(=O)NCc2ccc(C(=O)Nc3ccncc3N)cc2)cc(OC)c1OC] |
| V-36 | 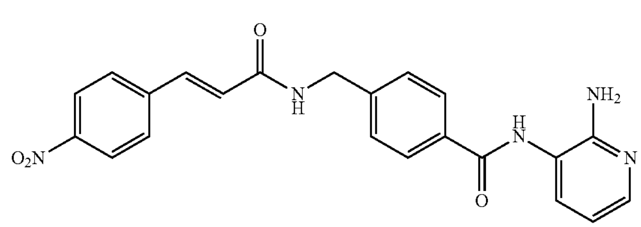 [SMILES: Nc1ncccc1NC(=O)c1ccc(CNC(=O)/C=C/c2ccc([N+](=O)[O-])cc2)cc1] |

| No. | Structures |
|---|---|
| V-37 | 4-aminocinnamoyl-NH-CH2-C6H4-C(O)NH-(2-aminopyridin-3-yl) |
| V-38 | 4-nitrocinnamoyl-NH-CH2-C6H4-C(O)NH-(3-aminopyridin-4-yl) |
| V-39 | 4-aminocinnamoyl-NH-CH2-C6H4-C(O)NH-(3-aminopyridin-4-yl) |
| V-40 | 4-fluorocinnamoyl-NH-CH2-C6H4-C(O)NH-(2-aminopyridin-3-yl) |
| V-41 | 4-fluorocinnamoyl-NH-CH2-C6H4-C(O)NH-(3-aminopyridin-4-yl) |
| V-42 | 3-(pyridin-3-yl)acryloyl-NH-CH2-C6H4-C(O)NH-(2-aminopyridin-3-yl) |
| V-43 | 3-(pyridin-3-yl)acryloyl-NH-CH2-C6H4-C(O)NH-(3-aminopyridin-4-yl) |

| No. | Structures |
|---|---|
| V-44 | 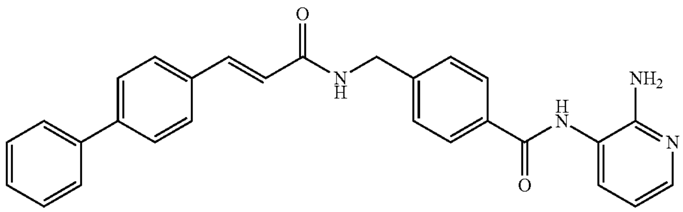 [SMILES: Nc1ncccc1NC(=O)c1ccc(CNC(=O)/C=C/c2ccc(-c3ccccc3)cc2)cc1] |
| V-45 | 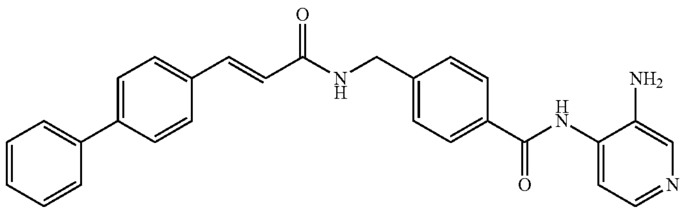 [SMILES: Nc1cnccc1NC(=O)c1ccc(CNC(=O)/C=C/c2ccc(-c3ccccc3)cc2)cc1] |
| V-46 | 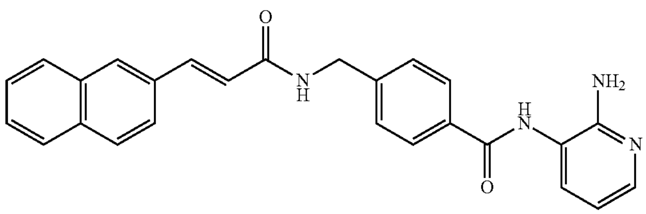 [SMILES: Nc1ncccc1NC(=O)c1ccc(CNC(=O)/C=C/c2ccc3ccccc3c2)cc1] |
| V-47 | 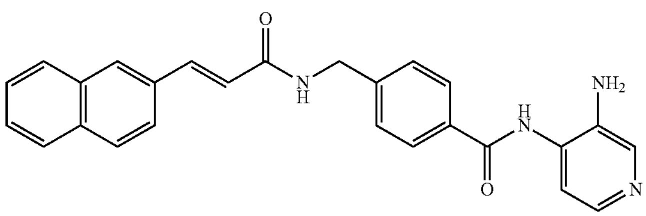 [SMILES: Nc1cnccc1NC(=O)c1ccc(CNC(=O)/C=C/c2ccc3ccccc3c2)cc1] |
| V-48 | 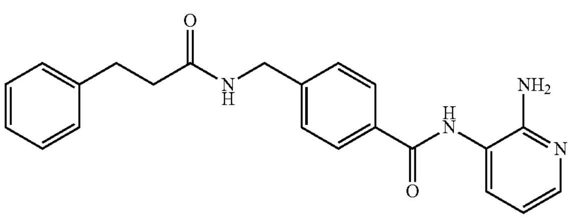 |
| V-49 | 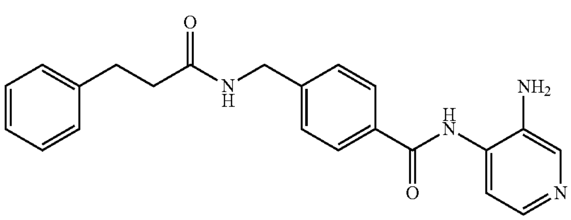 [SMILES: Nc1cnccc1NC(=O)c1ccc(CNC(=O)CCc2ccccc2)cc1] |
| V-50 | 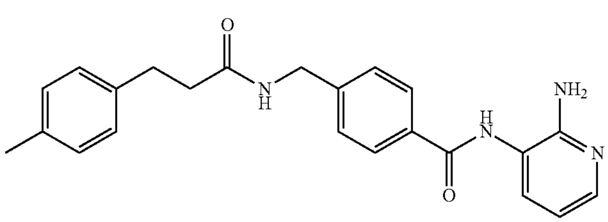 [SMILES: Cc1ccc(CCC(=O)NCc2ccc(C(=O)Nc3cccnc3N)cc2)cc1] |

| No. | Structures |
|---|---|
| V-51 | 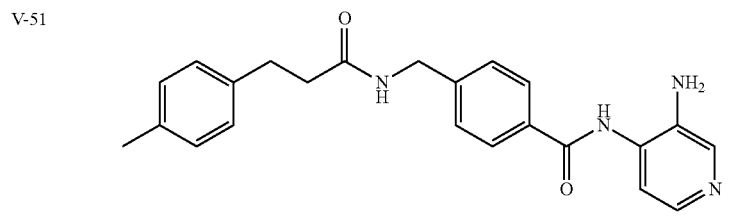 |
| V-52 | 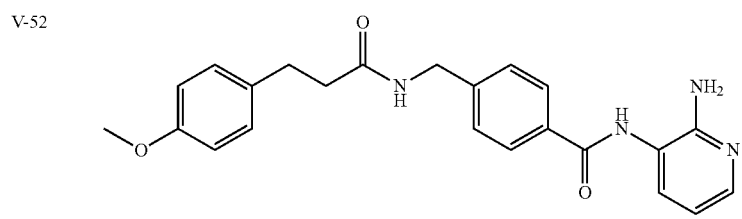 |
| V-53 | 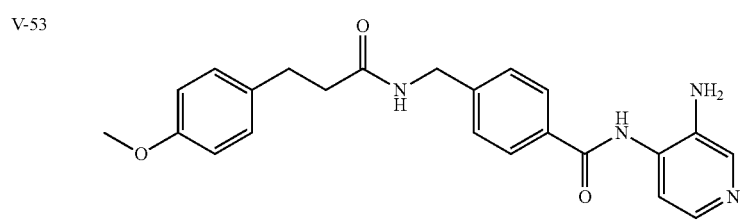 |
| V-54 | 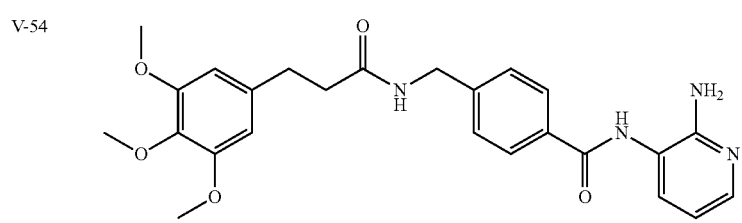 |
| V-55 | 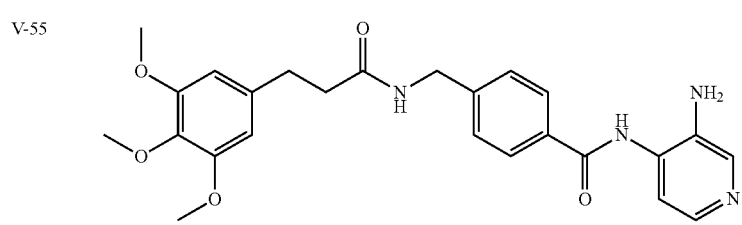 |
| V-56 | 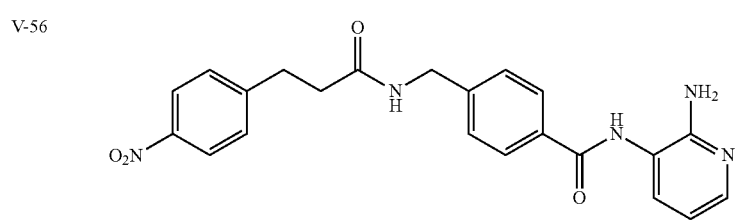 |
| V-57 | 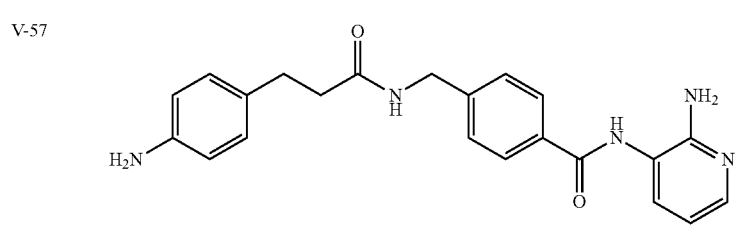 |

-continued

| No. | Structures |
|---|---|
| V-58 | 4-nitrophenyl-CH₂CH₂-C(=O)-NH-CH₂-(4-phenyl)-C(=O)-NH-(3-amino-pyridin-4-yl) |
| V-59 | 4-aminophenyl-CH₂CH₂-C(=O)-NH-CH₂-(4-phenyl)-C(=O)-NH-(3-amino-pyridin-4-yl) |
| V-60 | 4-fluorophenyl-CH₂CH₂-C(=O)-NH-CH₂-(4-phenyl)-C(=O)-NH-(2-amino-pyridin-3-yl) |
| V-61 | 4-fluorophenyl-CH₂CH₂-C(=O)-NH-CH₂-(4-phenyl)-C(=O)-NH-(3-amino-pyridin-4-yl) |
| V-62 | pyridin-3-yl-CH₂CH₂-C(=O)-NH-CH₂-(4-phenyl)-C(=O)-NH-(2-amino-pyridin-3-yl) |
| V-63 | pyridin-3-yl-CH₂CH₂-C(=O)-NH-CH₂-(4-phenyl)-C(=O)-NH-(3-amino-pyridin-4-yl) |
| V-64 | 4-biphenyl-CH₂CH₂-C(=O)-NH-CH₂-(4-phenyl)-C(=O)-NH-(2-amino-pyridin-3-yl) |

-continued
| No. | Structures |
|---|---|
| V-65 | 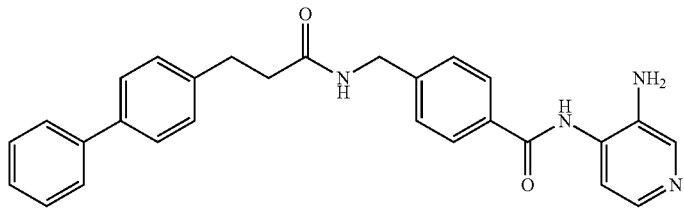 [SMILES: Nc1cnccc1NC(=O)c1ccc(CNC(=O)CCc2ccc(-c3ccccc3)cc2)cc1] |
| V-66 | 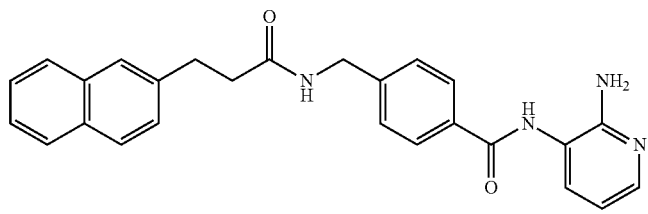 [SMILES: Nc1ncccc1NC(=O)c1ccc(CNC(=O)CCc2ccc3ccccc3c2)cc1] |
| V-67 | 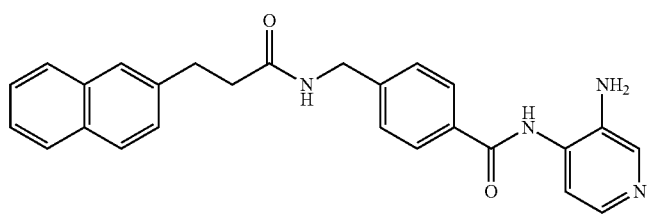 [SMILES: Nc1cnccc1NC(=O)c1ccc(CNC(=O)CCc2ccc3ccccc3c2)cc1] |
| V-68 | 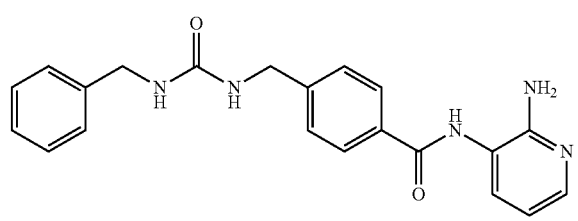 [SMILES: Nc1ncccc1NC(=O)c1ccc(CNC(=O)NCc2ccccc2)cc1] |
| V-69 | 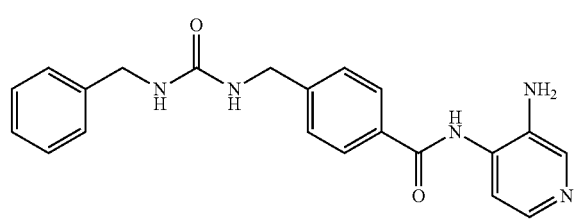 [SMILES: Nc1cnccc1NC(=O)c1ccc(CNC(=O)NCc2ccccc2)cc1] |
| V-70 | 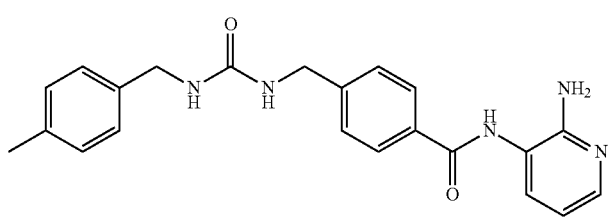 |
| V-71 | 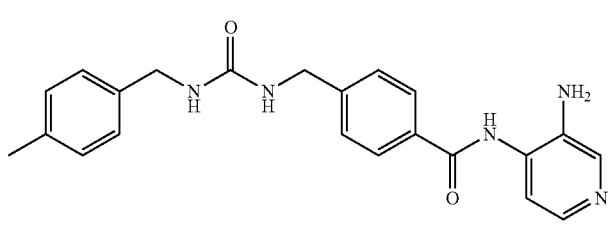 [SMILES: Cc1ccc(CNC(=O)NCc2ccc(C(=O)Nc3ccncc3N)cc2)cc1] |

-continued
| No. | Structures |
|---|---|
| V-72 | 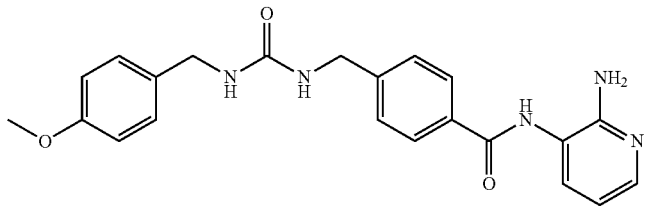 [SMILES: COc1ccc(CNC(=O)NCc2ccc(C(=O)Nc3cccnc3N)cc2)cc1] |
| V-73 | 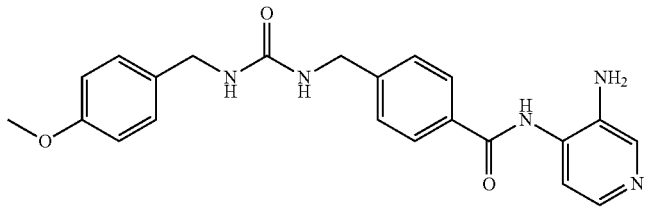 [SMILES: COc1ccc(CNC(=O)NCc2ccc(C(=O)Nc3ccncc3N)cc2)cc1] |
| V-74 | 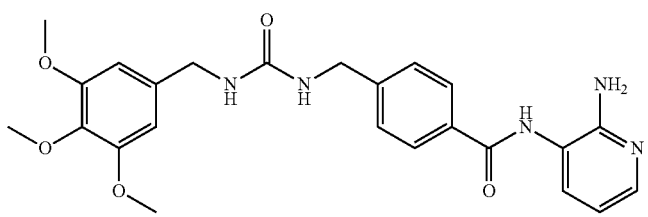 [SMILES: COc1cc(CNC(=O)NCc2ccc(C(=O)Nc3cccnc3N)cc2)cc(OC)c1OC] |
| V-75 | 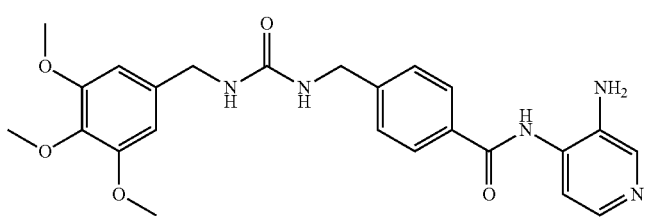 [SMILES: COc1cc(CNC(=O)NCc2ccc(C(=O)Nc3ccncc3N)cc2)cc(OC)c1OC] |
| V-76 | 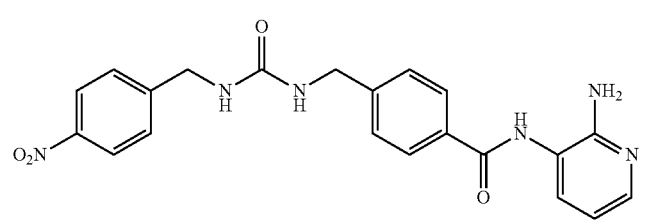 |
| V-77 | 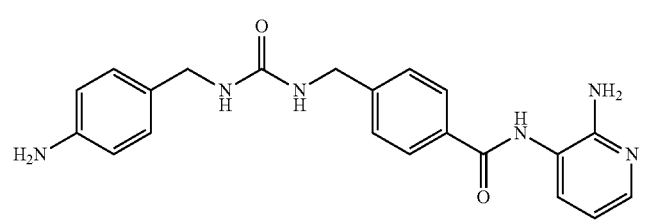 [SMILES: Nc1ncccc1NC(=O)c1ccc(CNC(=O)NCc2ccc([N+](=O)[O-])cc2)cc1] |
| V-78 | 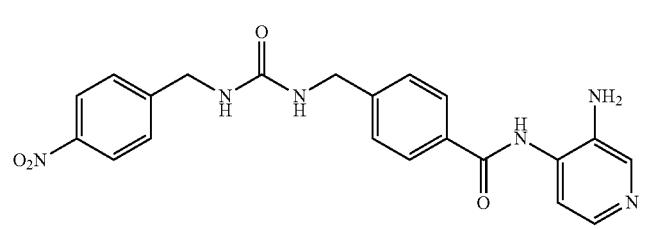 |

-continued
| No. | Structures |
|---|---|
| V-79 | 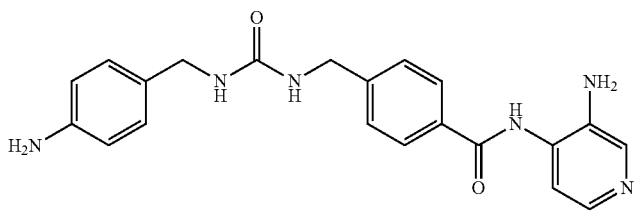 [SMILES: Nc1cnccc1NC(=O)c1ccc(CNC(=O)NCc2ccc([N+](=O)[O-])cc2)cc1] |
| V-80 | 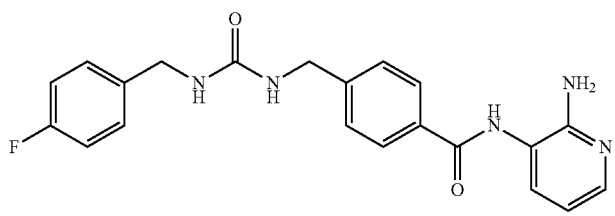 [SMILES: Nc1ncccc1NC(=O)c1ccc(CNC(=O)NCc2ccc(F)cc2)cc1] |
| V-81 | 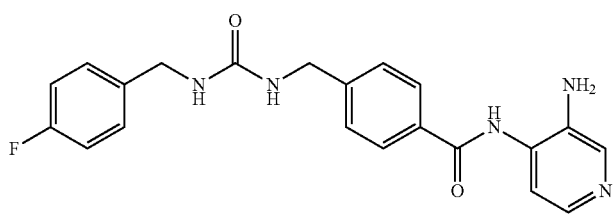 [SMILES: Nc1cnccc1NC(=O)c1ccc(CNC(=O)NCc2ccc(F)cc2)cc1] |
| V-82 | 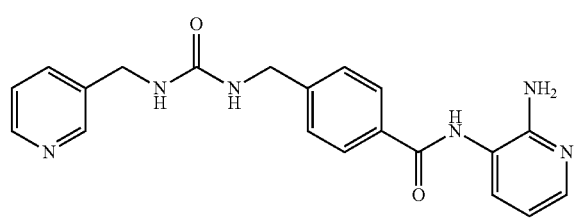 |
| V-83 | 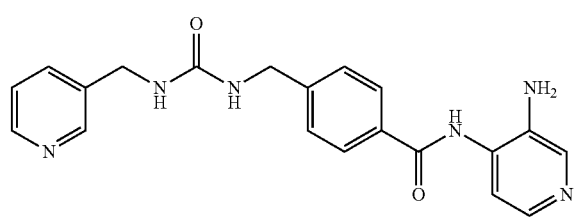 [SMILES: Nc1cnccc1NC(=O)c1ccc(CNC(=O)NCc2cccnc2)cc1] |
| V-84 | 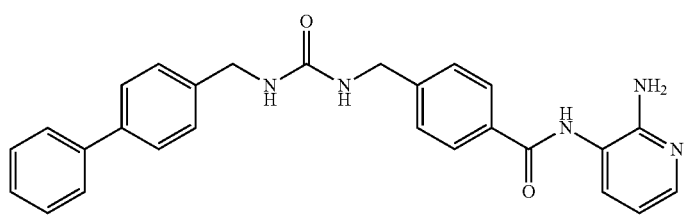 [SMILES: Nc1ncccc1NC(=O)c1ccc(CNC(=O)NCc2ccc(-c3ccccc3)cc2)cc1] |
| V-85 | 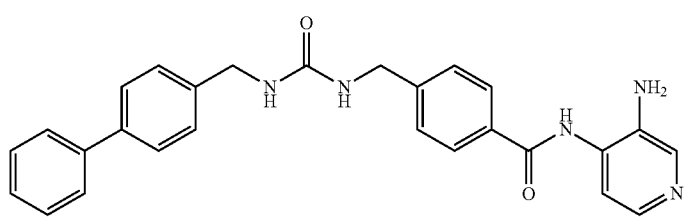 [SMILES: Nc1cnccc1NC(=O)c1ccc(CNC(=O)NCc2ccc(-c3ccccc3)cc2)cc1] |

| No. | Structures |
|---|---|
| V-86 | 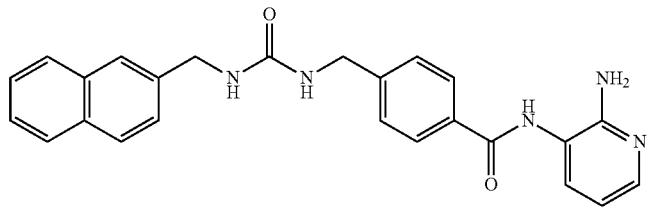 [SMILES: Nc1ncccc1NC(=O)c1ccc(CNC(=O)NCc2ccc3ccccc3c2)cc1] |
| V-87 | 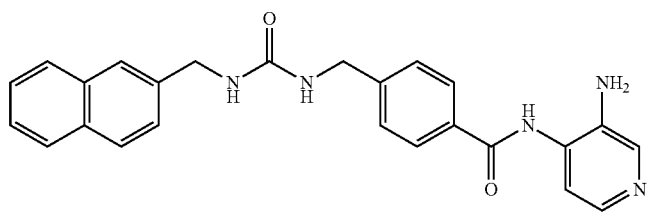 [SMILES: Nc1cnccc1NC(=O)c1ccc(CNC(=O)NCc2ccc3ccccc3c2)cc1] |
| V-88 | 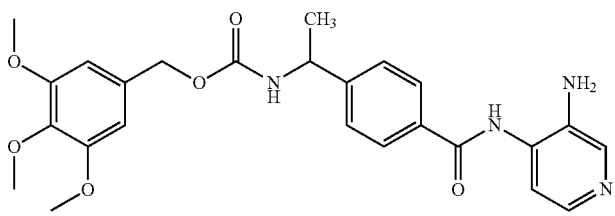 [SMILES: COc1cc(COC(=O)NC(C)c2ccc(C(=O)Nc3ccncc3N)cc2)cc(OC)c1OC] |
| V-89 | 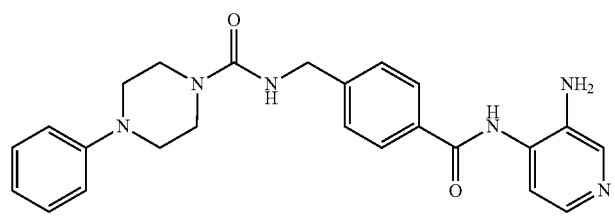 [SMILES: Nc1cnccc1NC(=O)c1ccc(CNC(=O)N2CCN(c3ccccc3)CC2)cc1] |
| V-90 | 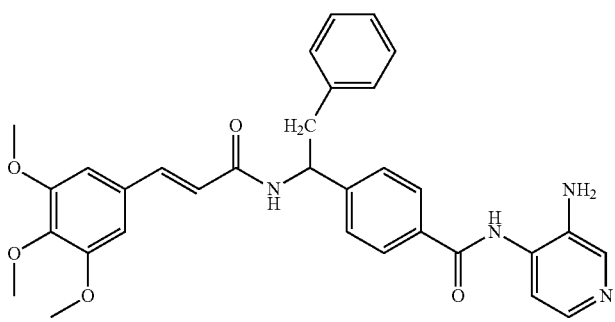 [SMILES: COc1cc(/C=C/C(=O)NC(Cc2ccccc2)c2ccc(C(=O)Nc3ccncc3N)cc2)cc(OC)c1OC] |
| V-91 | 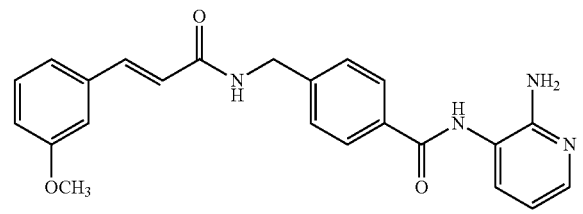 [SMILES: COc1cccc(/C=C/C(=O)NCc2ccc(C(=O)Nc3cccnc3N)cc2)c1] |

| No. | Structures |
|---|---|
| V-92 | 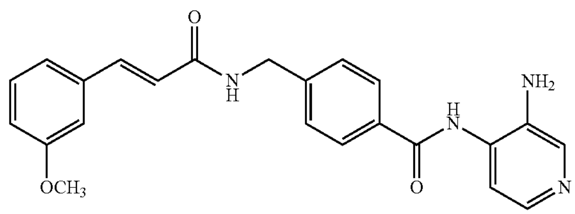 [SMILES: COc1cccc(/C=C/C(=O)NCc2ccc(C(=O)Nc3ccncc3N)cc2)c1] |
| V-93 | 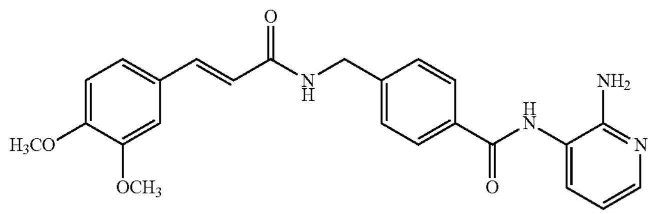 [SMILES: COc1ccc(/C=C/C(=O)NCc2ccc(C(=O)Nc3cccnc3N)cc2)cc1OC] |
| V-94 | 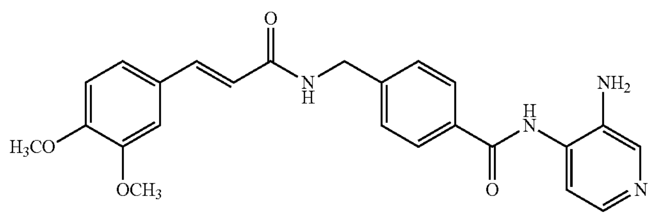 [SMILES: COc1ccc(/C=C/C(=O)NCc2ccc(C(=O)Nc3ccncc3N)cc2)cc1OC] |
| V-95 | 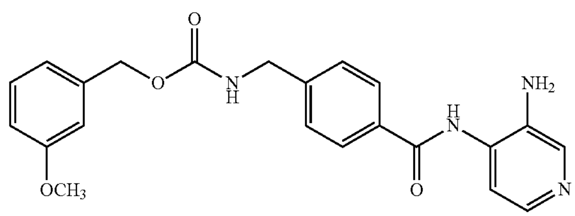 [SMILES: COc1cccc(COC(=O)NCc2ccc(C(=O)Nc3ccncc3N)cc2)c1] |
| V-96 | 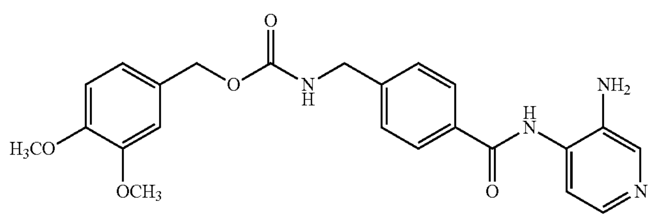 [SMILES: COc1ccc(COC(=O)NCc2ccc(C(=O)Nc3ccncc3N)cc2)cc1OC] |
The compound of the present invention can by synthesized with the following methods:
Method One:
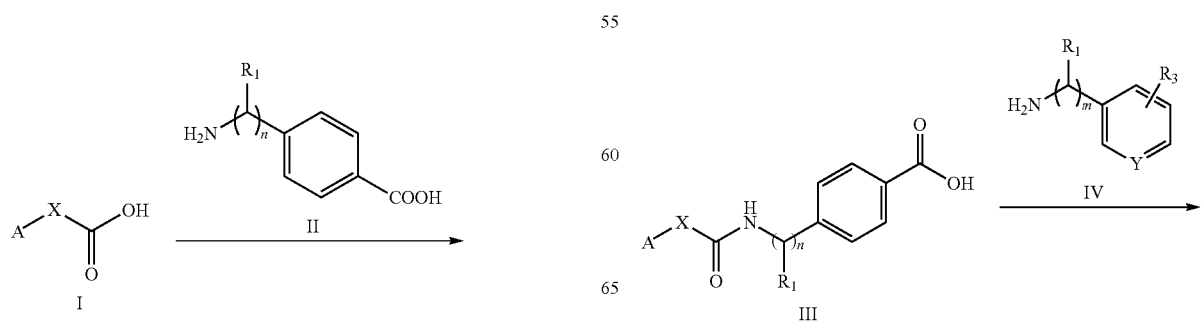

-continued

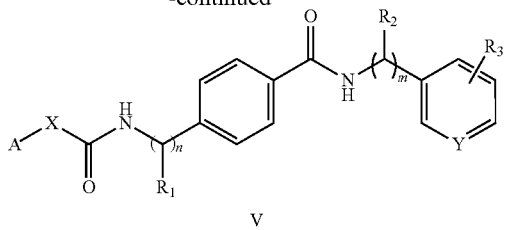

V

Compound I (10 mmol), and thionylchloride (4.72 g, 40 mmol) are dissolved in 10 ml of a solvent A and heated at flux for 4 hours. The solvent and the unreacted thionylchloride are evaporated under reduced pressure. The obtained product is drop-added to a mixed solution of Compound II (10 mmol) and sodium hydroxide (10 ml, 1 mol/L) under ice bath, stirring continuously at room temperature five hours after drop-adding. The reaction is stopped and 5N hydrochloric acid is added to adjust pH to about 4.5. Large amount of solids are precipitated, filtered and dried to obtain intermediate III;

The intermediate III (1 mmol), compound IV (1 mmol), O-(1H-benzotriazol-1-yl)-N,N,N',N'-tetramethyuronium hexafluorophosphate (abbreviated as HBTU) (0.379 g, 1 mmol) are added to 10 ml of solvent B in turn. Triethylamine (2 mmol) is drop-added thereto while maintaining cooled by the ice bath, and stirring continuously again at room temperature 4 hours. The reaction solution is poured into ice-water, and hydrochloric acid is added to adjust pH to about 7-9. Extracting with dichloromethane, drying over anhydrous magnesium sulfate and filtrating. The organic phase is concentrated, and the residue is purified through column chromatography to obtain product V.

Method Two:

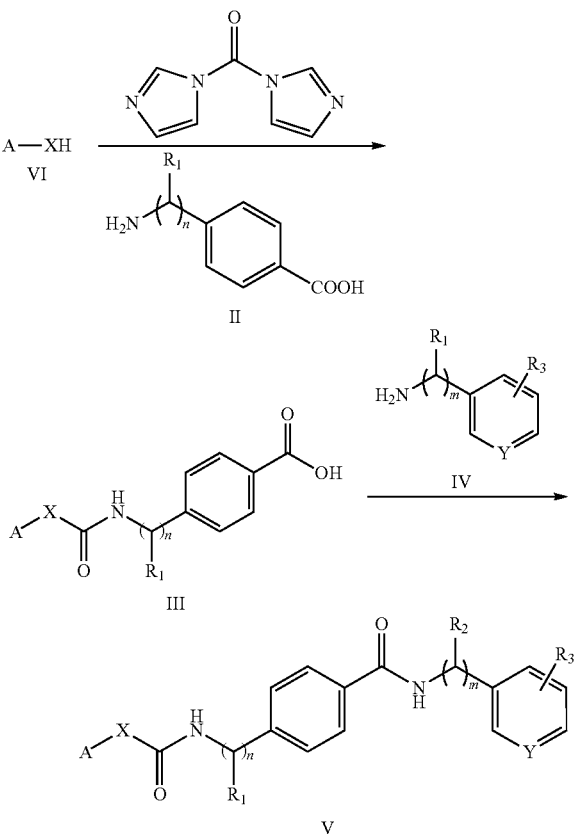

N,N-carbonyldiimidazole (1.62 g, 10 mmol) is dissolved in 10 ml of anhydrous tetrahydrofuran while controlling temperature at 0-10° C. using an ice bath. A mixed solution of VI (10 mmol) and 10 ml of anhydrous tetrahydrofuran is added in three portions in 10 minutes. Reacting continuously at 0-10° C. for 1 hour, and the reaction solution becomes clear. The above mixed solution is drop-added to a mixed solution of II (10 mmol) and sodium hydroxide aqueous solution (10 ml, 1 mol/L). Stirring continuously at room temperature 4 hours and stopping the reaction. 5N hydrochloric acid is added to adjust pH to about 4.5, and the reaction solution becomes clear. About 15 ml of the solvent is evaporated out under reduced pressure. Large amount of solids are precipitated, filtrated and dried to obtain the intermediate III.

The intermediate III (1 mmol), IV (1 mmol), HBTU (0.379 g, 1 mmol) are added to 10 ml of solvent B in turn, while maintaining cooled with ice bath. Triethylamine (2 mmol) is drop-added, then recovering to room temperature and stirring continuously 4 hours. The reaction solution is poured into ice-water, hydrochloric acid is added to adjust pH to about 7-9. Extracting with dichloromethane and drying over anhydrous magnesium sulfate. After standing, separating liquid and concentrating organic phase, and the residue is purified with column chromatography to obtain product V.

In the above reaction methods, A, X, $R_1$, $R_2$, $R_3$, Y, m, n are the same as defined above;

wherein, solvent A and B are: benzene, toluene, dichloromethane, N,N-dimethylformamide or thionylchloride, etc.

Compound I can be obtained commercially or synthesized according the method recorded in <Chinese Journal of Medicinal Chemistry>, 1993, 3 (3), 211, etc. Compound II, compound VI and HBTU can be available commercially; and compound IV can be synthesized according to the method recorded in *Heterocyclic Chem.*, 23, 669 (1986).

The pharmacological tests show that the compound or a salt thereof of the present invention not only inhibits histone deacetylase strongly, but also has strong activity in inducing differentiation and anti-proliferation to some tumor cells, and can be used for treating cancers and disorders associated with differentiation and proliferation, and are particularly excellent for the treatment of blood cancers and solid tumors.

The present invention further relates to a composition, comprising a therapeutically effective amount of the said compound or a salt thereof and a pharmaceutically acceptable carrier; the said carrier is conventional carrier materials such as flavors, sweeteners, liquid or solid fillers or diluents. The composition is formulated to conventional pharmaceutical formulations such as a tablet, capsule, powder, syrup, liquid, suspension or injection with commonly known methods of the field; the formulations typically contain 1-70 wt %, preferably 5-50% of effective ingredient.

The compound of the present invention can be administered clinically to mammals (including humans) through oral administration or injection, preferably through oral administration. The dosage is 0.0001 to 200 mg/kg (body weight) per day. The optimized dosage depends on individuals. Normally it starts from a small amount and increases gradually.

Animal tests show that the compound or a salt thereof of the present invention has less toxicity.

The benefit of the present invention lies in that the compound and pharmaceutical formulations thereof are potent for treating disorders caused by abnormal gene expression such as tumors, endocrine disorders, immune system disorders, inherited diseases and nervous system diseases.

MODE OF CARRYING OUT THE INVENTION

The contents of the present invention are further illustrated with combination of the following examples. However, the scope of protection of the present application should not be limited by the examples. The percentages described in the present invention are all weight percentages, unless particularly marked otherwise.

EXAMPLE 1

V-1 N-(2-aminobenzyl)-4-[(3-pyridylmethoxyacyl)aminomethyl]benzamide

N,N-carbonyldiimidazole (1.62 g, 10 mmol), 3-pyridylmethanol (1.08 g, 10 mmol), p-aminobenzoic acid (1.52 g, 10 mmol) are used according to the method for the production of intermediate III in Method two, are used to obtain 2.47 g of 4-[(3-pyridylmethoxyacyl)aminomethyl]benzoic acid (intermediate M-1) as a white solid, with a yield of 86.2%.

O-nitrotoluene (3.4 g, 25 mmol) is dissolved in 140 ml of anhydrous carbon tetrachloride, and benzoyl peroxide (0.290 g, 1.2 mmol) and N-bromosuccinimide (4.450 g, 25 mmol) are added. The reaction mixture is stirred, heated at reflux for 4 hours until N-bromosuccinimide is floated up completely. Cooling and then filtrating, washing with cold sodium bicarbonate aqueous solution (2×), and then ice-water (2×), and drying over anhydrous magnesium sulfate overnight. After filtration and concentration, the product is recrystallized with aqueous ethanol to obtain o-nitrobenzyl bromide as a white crystal, with a yield of 84.5%, m.p. 45-47° C.

O-nitrobenzyl (0.214 g, 1 mmol) is added to 30 ml of methanol solution of 7N amino (self-prepared) and heated under microwave at 100° C. for 15 minutes. Cooling and then evaporating methol to dryness. After recrystallization with dichloromethane, o-nitrobenzylamine hydrobromide is obtained, as a white solid, with a yield of 95.7%.

M-1 (0.286 g, 1 mmol), o-nitrobenzylamine (0.152 g, 1 mmol), HBTU (0.379 g, 1 mmol), 10 ml of dichloromethane, and triethylamine (0.202 g, 2 mmol) are used according to the method for the production of intermediate V in Method two to obtain a yellow solid. The yellow solid is dissolved in methanol, adding stannous chloride dehydrate (0.678 g, 3 mmol) and refluxing 2 hours. After concentrating methanol, the residue is poured into ice-water, and a saturated solution of potassium carbonate is added to adjust pH to 9. Extracting with dichloromethane and drying over anhydrous magnesium sulfate overnight. After concentrating the solvent, the product is recrystallized with ethyl acetate to obtain a light yellow solid, with a yield of 57.7%.

MS (ES+):m/e 391.17.

$^1$H-NMR (400 MHz, DMSO-$d_6$) δppm: 4.22 (2H, s, —C$\underline{H}_2$), 4.46 (2H, s, —C$\underline{H}_2$), 5.34 (2H, s, —C$\underline{H}_2$), 6.34 (1H, d, Ar—$\underline{H}$), 6.53 (1H, dd, Ar—$\underline{H}$), 6.81 (1H, d, Ar—$\underline{H}$), 6.96 (1H, dd, Ar—$\underline{H}$), 7.24 (2H, d, Ar—$\underline{H}$), 7.42 (1H, dd, Ar—$\underline{H}$), 7.83 (2H, d, Ar—$\underline{H}$), 7.90 (1H, d, Ar—$\underline{H}$), 8.33 (1H, d, Ar—$\underline{H}$), 8.70 (1H, s, Ar—$\underline{H}$), 9.60 (1H, s, —C(=O)—N$\underline{H}$—), 10.12 (1H, s, —C(=O)—N$\underline{H}$—), 5.97 (2H, s, —N$\underline{H}_2$).

EXAMPLE 2

V-2 N-(2-pyridyl)-4-[(3-pyridylmethoxyacyl)aminomethyl]benzamide

M-1 (0.286 g, 1 mmol), 2-aminopyridine (0.094 g, 1 mmol), HBTU (0.379 g, 1 mmol), N,N-dimethylformamide (10 ml), and triethylamine (0.202 g, 2 mmol), according to the method for the production of product V in Method two to obtain 0.231 g of a white solid, with a yield of 63.9%.

MS (ES+):m/e 363.14.

$^1$H-NMR (400 MHz, DMSO-$d_6$) δppm: 4.24 (2H, s, —C$\underline{H}_2$), 5.38 (2H, s, —C$\underline{H}_2$), 6.70 (1H, d, Ar—$\underline{H}$), 6.75 (1H, dd, Ar—$\underline{H}$), 7.24 (2H, d, Ar—$\underline{H}$), 7.39 (1H, dd, Ar—$\underline{H}$), 7.42 (1H, dd, Ar—$\underline{H}$), 7.83 (2H, d, Ar—$\underline{H}$), 7.90 (1H, d, Ar—$\underline{H}$), 7.98 (1H, d, Ar—$\underline{H}$), 8.33 (1H, d, Ar—$\underline{H}$), 8.70 (1H, s, Ar—$\underline{H}$), 9.56 (1H, s, —C(=O)—N$\underline{H}$—), 10.07 (1H, s, —C(=O)—N$\underline{H}$—).

EXAMPLE 3

V-3 N-(3-pyridyl)-4-[(3-pyridylmethoxyacyl)aminomethyl]benzamide

M-1 (0.286 g, 1 mmol), 3-aminopyridine (0.094 g, 1 mmol), HBTU (0.379 g, 1 mmol). N,N-dimethylformamide (10 ml), and triethylamine (0.202 g, 2 mmol) are used according to the method for the production of product V in Method two to obtain 0.265 g of a white solid, with a yield of 73.3%.

MS(ES+):m/e 363.14.

$^1$H-NMR (400 MHz, DMSO-$d_6$) δppm: 4.23 (2H, s, —C$\underline{H}_2$), 5.34 (2H, s, —C$\underline{H}_2$), 7.24 (2H, d, Ar—$\underline{H}$), 7.41 (1H, dd, Ar—$\underline{H}$), 7.42 (1H, dd, Ar—$\underline{H}$), 7.83 (2H, d, Ar—$\underline{H}$), 7.90 (1H, d, Ar—$\underline{H}$), 7.92 (1H, d, Ar—$\underline{H}$), 8.18 (1H, d, Ar—$\underline{H}$), 8.33 (1H, d, Ar—$\underline{H}$), 8.70 (1H, s, Ar—$\underline{H}$), 8.93 (1H, s, Ar—$\underline{H}$), 8.56 (1H, s, —C(=O)—N$\underline{H}$—), 9.24 (1H, s, —C(=O)—N$\underline{H}$—).

EXAMPLE 4

V-4 N-(2-amino-3-pyridyl)-4-[(3-pyridylmethoxyacyl)aminomethyl]benzamide

M-1 (0.286 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.216 g of a white solid, with a yield of 57.4%.

MS(ES+):m/e 378.14.

$^1$H-NMR (400 MHz, DMSO-$d_6$) δppm: 4.32 (2H, s, —C$\underline{H}_2$), 5.34 (2H, s, —C$\underline{H}_2$), 6.64 (1H, dd, Ar—$\underline{H}$), 6.95 (1H, d, Ar—$\underline{H}$), 7.24 (2H, d, Ar—$\underline{H}$), 7.42 (1H, dd, Ar—$\underline{H}$), 7.75 (1H, d, Ar—$\underline{H}$), 7.83 (2H, d, Ar—$\underline{H}$), 7.90 (1H, d, Ar—$\underline{H}$), 8.33 (1H, d, Ar—$\underline{H}$), 8.70 (1H, s, Ar—$\underline{H}$), 9.58 (1H, s, —C(=O)—N$\underline{H}$—), 10.24 (1H, s, —C(=O)—N$\underline{H}$—), 5.83 (2H, s, —N$\underline{H}_2$).

EXAMPLE 5

V-5 N-(2-amino-4-pyridyl)-4-[(3-pyridylmethoxyacyl)aminomethyl]benzamide

M-1 (0.286 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.206 g of a white solid, with a yield of 54.7%.

MS(ES+):m/e 378.16.

$^1$H-NMR (400 MHz, DMSO-$d_6$) δppm: 4.25 (2H, s, —C$\underline{H}_2$), 5.34 (2H, s, —C$\underline{H}_2$), 6.66 (1H, dd, Ar—$\underline{H}$), 7.24 (2H, d, Ar—$\underline{H}$), 7.42 (1H, dd, Ar—$\underline{H}$), 7.49 (1H, d, Ar—$\underline{H}$), 7.83 (2H, d, Ar—$\underline{H}$), 7.90 (1H, d, Ar—$\underline{H}$), 8.33 (1H, d, Ar—$\underline{H}$), 8.38 (1H, d, Ar—$\underline{H}$), 8.70 (1H, s, Ar—$\underline{H}$), 9.55 (1H, s, —C(=O)—N$\underline{H}$—), 9.78 (1H, s, —C(=O)—N$\underline{H}$—), 5.88 (2H, s, —N$\underline{H}_2$).

EXAMPLE 6

V-8 N-[1-(2-aminophenyl)ethyl]-4-[(3-pyridylmethoxyacyl)aminomethyl]benzamide

M-1 (0.286 g, 1 mmol), 2-(1-aminoethyl)aniline (0.136 g, 1 mmol), HBTU (0.379 g, 1 mmol), dichloromethane (10 ml), and triethylamine (0.202 g, 2 mmol) are used according to the method for the production of product V in Method two to obtain 0.305 g of a white solid, with a yield of 78.0%.

MS(ES+):m/e 405.15.

$^1$H-NMR (400 MHz, DMSO-d$_6$) δppm: 1.58 (3H, s, —CH$_3$), 4.32 (2H, s, —CH$_2$), 5.00 (1H, q, —CHCH$_3$), 5.38 (2H, s, —CH$_2$), 6.41 (1H, d, Ar—H), 6.57 (1H, dd, Ar—H), 6.87 (1H, d, Ar—H), 6.97 (1H, dd, Ar—H), 7.24 (2H, d, Ar—H), 7.37 (1H, dd, Ar—H), 7.39 (2H, d, Ar—H), 7.42 (1H, dd, Ar—H), 7.85 (2H, d, Ar—H), 7.90 (1H, d, Ar—H), 8.33 (1H, d, Ar—H), 8.70 (1H, s, Ar—H), 10.11 (1H, s, —C(=O)—NH—), 10.03 (1H, s, —C(=O)—NH—), 5.79 (2H, s, —NH$_2$).

EXAMPLE 7

V-9 N-(2-amino-4-pyridyl)-4-(benzyloxyacylaminomethyl)benzamide

N,N-carbonyldiimidazole (1.62 g, 10 mmol), anhydrous tetrahydrofuran (10 ml), benzenemethanol (1.08 g, 10 mmol), p-aminobenzoic acid (1.52 g, 10 mmol), and 10 ml of 1 mol/L sodium hydroxide solution are used according to the method for the production of intermediate III in Method two to obtain 2.67 g of 4-(benzyloxyacylaminomethyl)benzoic acid (intermediate M-6) as a white solid, with a yield of 93.8%.

M-6 (0.285 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.172 g of a light pink solid, with a yield of 45.7%.

MS(ES+):m/e 377.10.

$^1$H-NMR (400 MHz, DMSO-d$_6$) δppm: 4.22 (2H, s, —CH$_2$), 5.05 (2H, s, —CH$_2$), 6.66 (1H, d, Ar—H), 7.24 (2H, d, Ar—H), 7.33 (2H, d, Ar—H), 7.37 (1H, dd, Ar—H), 7.39 (2H, dd, Ar—H), 7.49 (1H, d, Ar—H), 7.83 (2H, d, Ar—H), 8.38 (1H, d, Ar—H), 10.11 (1H, s, —C(=O)—NH—), 10.13 (1H, s, —C(=O)—NH—), 5.77 (2H, s, —NH$_2$).

EXAMPLE 8

V-10 N-(2-amino-3-pyridyl)-4-(benzyloxyacylaminomethyl)benzamide

M-6 (0.285 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.173 g of a white solid, with a yield of 46.0%.

MS(ES+):m/e 377.19.

$^1$H-NMR (400 MHz, DMSO-d$_6$) δppm: 4.26 (2H, s, —CH$_2$), 5.05 (2H, s, —CH$_2$), 6.64 (1H, dd, Ar—H), 6.95 (1H, d, Ar—H), 7.33 (2H, d, Ar—H), 7.37 (1H, dd, Ar—H), 7.39 (2H, dd, Ar—H), 7.75 (1H, d, Ar—H), 7.83 (2H, d, Ar—H), 9.58 (1H, s, —C(=O)—NH—), 9.13 (1H, s, —C(=O)—NH—), 5.44 (2H, s, —NH$_2$).

EXAMPLE 9

V-11 N-(2-amino-3-pyridyl)-4-[(4-methylbenzyloxyacyl)aminomethyl]benzamide

N,N-carbonyldiimidazole (1.62 g, 10 mmol), p-methylbenzenemethanol (1.22 g, 10 mmol), p-aminobenzoic acid (1.52 g, 10 mmol), and 10 ml of 1 mol/L sodium hydroxide solution are used according to the method for the production of compound III in Method two to obtain 2.86 g of 4-[(4-methylbenzyloxyacyl)aminomethyl]benzoic acid (intermediate M-7) as a white solid, with a yield of 95.7%.

M-7 (0.299 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.180 g of a white solid, with a yield of 46.2%.

MS(ES+):m/e 390.16.

$^1$H-NMR (400 MHz, DMSO-d$_6$) δppm: 2.19 (3H, s, —CH$_3$), 4.25 (2H, s, —CH$_2$), 5.05 (2H, s, —CH$_2$), 6.64 (1H, dd, Ar—H), 6.95 (1H, d, Ar—H), 6.99 (2H, d, Ar—H), 7.07 (2H, d, Ar—H), 7.24 (2H, d, Ar—H), 7.75 (1H, d, Ar—H), 7.83 (2H, d, Ar—H), 9.58 (1H, s, —C(=O)—NH—), 9.13 (1H, s, —C(=O)—NH—), 5.44 (2H, s, —NH$_2$).

EXAMPLE 10

V-12 N-(2-amino-4-pyridyl)-4-[(4-methylbenzyloxyacyl)aminomethyl]benzamide

M-7 (0.299 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.172 g of a white solid, with a yield of 44.1%.

MS(ES+):m/e 390.13.

$^1$H-NMR (400 MHz, DMSO-d$_6$) δppm: 2.19 (3H, s, —CH$_3$), 4.33 (2H, s, —CH$_2$), 5.05 (2H, s, —CH$_2$), 6.66 (1H, d, Ar—H), 7.00 (2H, d, Ar—H), 7.07 (2H, d, Ar—H), 7.37 (2H, d, Ar—H), 7.49 (1H, d, Ar—H), 7.83 (2H, d, Ar—H), 8.38 (1H, s, Ar—H), 10.00 (1H, s, —C(=O)—NH—), 9.76 (1H, s, —C(=O)—NH—), 5.46 (2H, s, —NH$_2$).

EXAMPLE 11

V-13 N-(2-amino-3-pyridyl)-4-[(4-methoxybenzyloxyacyl)aminomethyl]benzamide

N,N-carbonyldiimidazole (1.62 g, 10 mmol), p-methoxybenzyloxymethanol (1.38 g, 10 mmol), p-aminobenzoic acid (1.52 g, 10 mmol), and 10 ml of 1 mol/L sodium hydroxide solution are used according to the method for the production of compound III in Method two to obtain 2.96 g of 4-[(4-methoxybenzyloxyacyl)aminomethyl]benzoic acid (intermediate M-8) as a white solid, with a yield of 94.0%.

M-8 (0.315 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.180 g of a white solid, with a yield of 44.3%.

MS(ES+):m/e 307.16.

$^1$H-NMR (400 MHz, DMSO-d$_6$) δppm: 3.91 (3H, s, —OCH$_3$), 4.22 (2H, s, —CH$_2$), 5.05 (2H, s, —CH$_2$), 6.64 (1H, dd, Ar—H), 6.91 (2H, d, Ar—H), 6.95 (1H, d, Ar—H), 6.99 (2H, d, Ar—H), 7.24 (2H, d, Ar—H), 7.75 (1H, d, Ar—H), 7.83 (2H, d, Ar—H), 10.11 (1H, s, —C(=O)—NH—), 9.96 (1H, s, —C(=O)—NH—), 5.78 (2H, s, —NH$_2$).

EXAMPLE 12

V-14 N-(2-amino-4-pyridyl)-4-[(4-methoxybenzyloxyacyl)aminomethyl]benzamide

V-11 (0.315 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.180 g of a white solid, with a yield of 40.0%.

MS(ES+):m/e 307.13.

$^1$H-NMR (400 MHz, DMSO-d$_6$) δppm: 3.93 (3H, s, —OCH$_3$), 4.28 (2H, s, —CH$_2$), 5.05 (2H, s, —CH$_2$), 6.69 (1H, d, Ar—H), 6.91 (2H, d, Ar—H), 6.99 (2H, d, Ar—H), 7.24 (2H, d, Ar—H), 7.49 (1H, d, Ar—H), 7.83 (2H, d, Ar—H), 8.38 (1H, s, Ar—H), 10.13 (1H, s, —C(=O)—NH—), 9.97 (1H, s, —C(=O)—NH—), 5.88 (2H, s, —NH$_2$).

EXAMPLE 13

V-15 N-(2-amino-3-pyridyl)-4-[(3,4,5-trimethoxybenzyloxyacyl)aminomethyl]benzamide N,N-carbonyldiimidazole (1.62 g, 10 mmol), 3,4,5-trimethoxybenzenemethanol (1.98 g, 10 mmol), p-aminobenzoic acid (1.52 g, 10 mmol), and 10 ml of 1 mol/L sodium hydroxide solution are used according to the method for the production of compound Ill in Method two to obtain 3.15 g of 4-[(3,4,5-trimethoxybenzyloxyacyl)aminomethyl]benzoic acid (intermediate M-9) as a white solid, with a yield of 84.1%.

M-9 (0.375 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.229 g of a white solid, with a yield of 49.2%.

MS(ES+):m/e 467.18.

$^1$H-NMR (400 MHz, DMSO-d$_6$) δppm: 3.91 (3H, s, —OCH$_3$), 3.92 (6H, s, —OCH$_3$), 4.22 (2H, s, —CH$_2$), 5.34 (2H, s, —CH$_2$), 6.15 (2H, d, Ar—H), 6.64 (1H, dd, Ar—H), 6.95 (1H, d, Ar—H), 7.24 (2H, d, Ar—H), 7.75 (1H, d, Ar—H), 7.83 (2H, d, Ar—H), 10.11 (1H, s, —C(=O)—NH—), 9.98 (1H, s, —C(=O)—NH—), 5.84 (2H, s, —NH$_2$).

EXAMPLE 14

V-16 N-(2-amino-4-pyridyl)-4-[(3,4,5-trimethoxybenzyloxyacyl)aminomethyl]benzamide M-9 (0.375 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.222 g of a white solid, with a yield of 47.6%.

MS(ES+):m/e 467.19.

$^1$H-NMR (400 MHz, DMSO-d$_6$) δppm: 3.91 (3H, s, —OCH$_3$), 3.92 (6H, s, —OCH$_3$), 4.27 (2H, s, —CH$_2$), 5.05 (2H, s, —CH$_2$), 6.15 (2H, d, Ar—H), 6.66 (1H, d, Ar—H), 7.24 (2H, d, Ar—H), 7.49 (1H, d, Ar—H), 7.83 (2H, d, Ar—H), 8.38 (1H, s, Ar—H), 10.01 (1H, s, —C(=O)—NH—), 9.98 (1H, s, —C(=O)—NH—), 5.74 (2H, s, —NH$_2$).

EXAMPLE 15

V-17 N-(2-amino-3-pyridyl)-4-[(4-nitrobenzyloxyacyl)aminomethyl]benzamide

N,N-carbonyldiimidazole (1.62 g, 10 mmol), p-nitrobenzenemethanol (1.53 g, 10 mmol), p-aminobenzoic acid (1.52 g, 10 mmol), and 10 ml of 1 mol/L sodium hydroxide solution are used according to the method for the production of compound III in Method two to obtain 2.90 g of 4-(nitrobenzyloxyacylaminomethyl)benzoic acid (intermediate M-10) as a light yellow solid, with a yield of 87.8%.

V-17 (0.330 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.197 g of a white solid, with a yield of 46.7%.

MS(ES+):m/e 422.10.

$^1$H-NMR (400 MHz, DMSO-d$_6$) δppm: 4.24 (2H, s, —CH$_2$), 5.05 (2H, s, —CH$_2$), 6.64 (1H, dd, Ar—H), 6.95 (1H, d, Ar—H), 7.24 (2H, d, Ar—H), 7.58 (2H, d, Ar—H), 7.75 (1H, d, Ar—H), 7.83 (2H, d, Ar—H), 8.22 (2H, d, Ar—H). 10.00 (1H, s, —C(=O)—NH—), 9.90 (1H, s, —C(=O)—NH—), 5.79 (2H, s, —NH$_2$).

EXAMPLE 16

V-18 N-(2-amino-3-pyridyl)-4-[(4-aminobenzyloxyacyl)aminomethyl]benzamide

Dissolving V-17 (0.421 g, 1 mmol) into methanol, thereto adding stannous chloride dihydrate (0.678 g, 3 mmol), refluxing 2 hours, and then concentrating methanol. The residue is poured into ice-water, and a saturated solution of potassium carbonate is added to adjust pH to 9. Extracting with dichloromethane and drying over anhydrous magnesium sulfate overnight. After concentrating the solvent, the product is recrystallized with ethyl acetate, to obtain 0.255 g of a light yellow solid, with a yield of 65.3%.

MS(ES+):m/e 392.16.

$^1$H-NMR (400 MHz, DMSO-d$_6$) δppm: 4.12 (2H, s, —CH$_2$), 5.1 (2H, s, —CH$_2$), 6.39 (2H, d, Ar—H). 6.64 (1H, dd, Ar—H), 6.94 (2H, d, Ar—H), 6.95 (1H, d, Ar—H), 7.24 (2H, d, Ar—H), 7.75 (1H, d, Ar—H), 7.83 (2H, d, Ar—H), 10.19 (1H, s, —C(=O)—NH—), 9.97 (1H, s, —C(=O)—NH—), 5.79 (2H, s, —NH$_2$), 5.89 (2H, s, —NH$_2$).

EXAMPLE 17

V-19 N-(2-amino-4-pyridyl)-4-[(4-nitrobenzyloxyacyl)aminomethyl]benzamide

M-10 (0.330 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the preparation of product V in Method two to obtain 0.194 g of a light yellow solid, with a yield of 46.0%.

MS(ES+):m/e 422.13.

$^1$H-NMR (400 MHz, DMSO-d$_6$) δppm: 4.29 (2H, s, —CH$_2$), 5.15 (2H, s, —CH$_2$), 6.66 (1H, d, Ar—H), 7.29 (2H, d, Ar—H), 7.49 (1H, d, Ar—H), 7.58 (2H, d, Ar—H), 7.87 (2H, d, Ar—H), 8.27 (2H, d, Ar—H), 8.38 (1H, s, Ar—H), 10.15 (1H, s, —C(=O)—NH—), 9.99 (1H, s, —C(=O)—NH—), 5.89 (2H, s, —NH$_2$).

EXAMPLE 18

V-20 N-(2-amino-4-pyridyl)-4-[(4-aminobenzyloxyacyl)aminomethyl]benzamide

Dissolving V-19 (0.421 g, 1 mmol) into methanol, thereto adding stannous chloride dihydrate (0.678 g, 3 mmol), refluxing 2 hours, and then concentrating methanol. The residue is poured into ice-water, and a saturated solution of potassium carbonate is added to adjust pH to 9. Extracting with dichloromethane and drying over anhydrous magnesium sulfate overnight. After concentrating the solvent, the product is recrystallized with ethyl acetate to obtain 0.258 g of a light yellow solid, with a yield of 66.0%.

MS(ES+):m/e 392.16.

$^1$H-NMR (400 MHz, DMSO-d$_6$) δppm: 4.34 (2H, s, —CH$_2$), 5.05 (2H, s, —CH$_2$), 6.39 (2H, d, Ar—H), 6.66 (1H, d, Ar—H), 6.94 (2H, d, Ar—H), 7.24 (2H, d, Ar—H), 7.49 (1H, d, Ar—H), 7.83 (2H, d, Ar—H), 8.38 (1H, s, Ar—H), 10.15 (1H, s, —C(=O)—NH—), 9.99 (1H, s, —C(=O)—NH—), 5.56 (2H, s, —NH$_2$), 5.89 (2H, s, —NH$_2$).

EXAMPLE 19

V-21 N-(2-amino-3-pyridyl)-4-[(4-fluorobenzyloxyacyl)aminomethyl]benzamide

N,N-carbonyldiimidazole (1.62 g, 10 mmol), p-fluorobenzenemethanol (1.26 g, 10 mmol), p-aminobenzoic acid (1.52 g, 10 mmol), and 10 ml of 1 mol/L sodium hydroxide solution are used according to the method for the production of the compound III in Method two to prepare 2.41 g of the 4-(fluorobenzyloxyacylaminomethyl)benzoic acid (intermediate M-11) as a white solid, with a yield of 79.5%.

M-11 (0.303 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the preparation of product V in Method two to obtain 0.225 g of a white solid, with a yield of 57.0%.

MS(ES+):m/e 395.13.

$^1$H-NMR (400 MHz, DMSO-d$_6$) δppm: 4.35 (2H, s, —CH$_2$), 5.12 (2H, s, —CH$_2$), 6.64 (1H, dd, Ar—H), 6.90 (2H, d, Ar—H), 6.99 (1H, d, Ar—H), 7.17 (2H, d, Ar—H), 7.24 (2H, d, Ar—H), 7.75 (1H, d, Ar—H), 7.83 (2H, d, Ar—H), 10.16 (1H, s, —C(=O)—NH—), 10.29 (1H, s, —C(=O)—NH—), 5.98 (2H, s, —NH$_2$).

EXAMPLE 20

V-22 N-(2-amino-4-pyridyl)-4-[(4-fluorobenzyloxyacyl)aminomethyl]benzamide

M-11 (0.303 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the preparation of product V in Method two to obtain 0.220 g of a white solid, with a yield of 55.8%.

MS(ES+):m/e 395.12.

$^1$H-NMR (400 MHz, DMSO-d$_6$) δppm: 4.32 (2H, s, —CH$_2$), 5.05 (2H, s, —CH$_2$), 6.66 (1H, d, Ar—H), 6.90 (2H, d, Ar—H), 7.18 (2H, d, Ar—H), 7.24 (2H, d, Ar—H), 7.49 (1H, d, Ar—H), 7.83 (2H, d, Ar—H), 8.38 (1H, s, Ar—H), 10.11 (1H, s, —C(=O)—NH—), 10.29 (1H, s, —C(=O)—NH—), 5.98 (2H, s, —NH$_2$).

EXAMPLE 21

V-23 N-(2-amino-3-pyridyl)-4-[(4-phenylbenzyloxyacyl)aminomethyl]benzamide

N,N-carbonyldiimidazole (1.62 g, 10 mmol), p-phenylbenzenemethanol (1.84 g, 10 mmol), p-aminobenzoic acid (1.52 g, 10 mmol), and 10 ml of 1 mol/L sodium hydroxide solution are used according to the method for the production of compound III in Method two to obtain 2.87 g of 4-(phenylbenzyloxyacylaminomethyl)benzoic acid (intermediate M-12) as a white solid, with a yield of 79.5%.

M-12 (0.361 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the preparation of product V in Method two to obtain 0.258 g of a white solid, with a yield of 57.0%.

MS(ES+):m/e 453.18

$^1$H-NMR (400 MHz, DMSO-d$_6$) δppm: 4.27 (2H, s, —CH$_2$), 5.05 (2H, s, —CH$_2$), 6.64 (1H, d, Ar—H), 6.95 (1H, dd, Ar—H), 7.24 (2H, d, Ar—H), 7.25 (2H, d, Ar—H), 7.38 (2H, d, Ar—H), 7.48 (5H, s, Ar—H), 7.75 (1H, d, Ar—H), 7.83 (2H, d, Ar—H), 10.11 (1H, s, —C(=O)—NH—), 10.29 (1H, s, —C(=O)—NH—), 5.98 (2H, s, —NH$_2$).

EXAMPLE 22

V-24 N-(2-amino-4-pyridyl)-4-[(4-phenylbenzyloxyacyl)aminomethyl]benzamide

M-12 (0.361 g, 1 mmol), 3,4-diaminopyridine (0.109 g 1 mmol), HBTU (0.379 g, 1 mmol), N,N-dimethylformamide (10 ml), and triethylamine (0.202 g, 2 mmol) are used according to the method for the preparation of product V in Method two to obtain 0.252 g of a white solid, with a yield of 55.8%.

MS(ES+):m/e 453.17

$^1$H-NMR (400 MHz, DMSO-d$_6$) δppm: 4.22 (2H, s; —CH$_2$), 5.05 (2H, s, —CH$_2$), 6.66 (1H, d, Ar—H), 7.24 (2H, d, Ar—H), 7.25 (2H, d, Ar—H), 7.38 (2H, d, Ar—H), 7.48 (5H, s, Ar—H), 7.49 (1H, d, Ar—H), 7.83 (2H, d, Ar—H), 8.38 (1H, s, Ar—H), 10.15 (1H, s, —C(=O)—NH—), 10.21 (1H, s, —C(=O)—NH—), 5.78 (2H, s, —NH$_2$).

EXAMPLE 23

V-25 N-(2-amino-3-pyridyl)-4-[(2-naphthylmethoxyacyl)aminomethyl]benzamide

N,N-carbonyldiimidazole (1.62 g, 10 mmol), 2-naphthylmethanol (1.58 g, 10 mmol), p-aminobenzoic acid (1.52 g, 10 mmol), and 10 ml of 1 mol/L sodium hydroxide solution are used according to the method for the production of compound III in Method two to obtain 2.66 g of 4-(2-naphthylmethoxyacylaminomethyl)benzoic acid (intermediate M-13) as a white solid, with a yield of 79.5%.

M-13 (0.335 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the preparation of product V in Method two to obtain 0.242 g of a white solid, with a yield of 57.0%.

MS(ES+):m/e 453.18

$^1$H-NMR (400 MHz, DMSO-d$_6$) δppm: 4.26 (2H, s, —CH$_2$), 5.45 (2H, s, —CH$_2$), 6.64 (1H, d, Ar—H), 6.95 (1H, dd, Ar—H), 7.24 (2H, d, Ar—H), 7.18 (1H, d, Ar—H), 7.46 (1H, s, Ar—H), 7.55 (1H, dd, Ar—H), 7.58 (1H, dd, Ar—H), 7.61 (1H, d, Ar—H), 7.64 (1H, d, Ar—H), 8.02 (1H, d, Ar—H), 7.75 (1H, d, Ar—H), 7.83 (2H, d, Ar—H), 10.16 (1H, s, —C(=O)—NH—), 10.21 (1H, s, —C(=O)—NH—), 5.78 (2H, s, —NH$_2$).

EXAMPLE 24

V-26 N-(2-amino-4-pyridyl)-4-[(2-naphthylmethoxyacyl)aminomethyl]benzamide

M-13 (0.335 g, 1 mmol, 3,4-diaminopyridine (0.109 g, 1 mmol), HBTU (0.379 g, 1 mmol), N,N-dimethylformamide (10 ml), and triethylamine (0.202 g, 2 mmol) are used according to the method for the preparation of product V in Method two to obtain 0.238 g of a white solid, with a yield of 55.8%.

MS(ES+):m/e 453.17

¹H-NMR (400 MHz, DMSO-d₆) δppm: 4.35 (2H, s, —CH₂), 5.54 (2H, s, —CH₂), 6.66 (1H, d, Ar—H). 7.49 (1H, d, Ar—H), 7.24 (2H, d, Ar—H), 7.18 (1H, d, Ar—H), 7.46 (1H, s, Ar—H), 7.65 (1H, dd, Ar—H), 7.68 (1H, dd, Ar—H), 7.71 (1H, d, Ar—H), 7.74 (1H, d, Ar—H), 8.02 (1H, d, Ar—H), 8.38 (1H, s, Ar—H), 7.83 (2H, d, Ar—H), 10.18 (1H, s, —C(=O)—NH—), 10.21 (1H, s, —C(=O)—NH—), 5.88 (2H, s, —NH₂).

EXAMPLE 25

V-27 N-(2-amino-3-pyridyl)-4-(cinnamoylaminomethyl)benzamide

Cinnamic acid (1.48 g, 10 mmol), thionylchloride (4.72 g, 40 mmol), dichloromethane (10 ml), p-aminobenzoic acid (1.52 g, 10 mmol), and 10 ml of 1 mol/L sodium hydroxide are used according to the method of the production of compound III in Method one to obtain 2.47 g of 4-(cinnamoylaminomethyl)benzoic acid (intermediate M-14) as a white solid, with a yield of 87.9%.

M-14 (0.281 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the preparation of product V in Method one to obtain 0.203 g of a white solid, with a yield of 54.6%.

MS(ES+):m/e 373.12.

¹H-NMR (400 MHz, DMSO-d₆) δppm: 4.29 (2H, s, —CH₂), 6.64 (1H, dd, Ar—H), 6.84 (1H, d, —CH=CH—), 6.95 (1H, d, Ar—H), 7.24 (2H, d, Ar—H), 7.47 (5H, s, Ar—H), 7.55 (1H, d, —CH=CH—), 7.75 (1H, d, Ar—H), 7.83 (2H, d, Ar—H), 10.28 (1H, s, —C(=O)—NH—), 10.22 (1H, s, —C(=O)—NH—), 5.89 (2H, s, —NH₂).

EXAMPLE 26

V-28 N-(2-amino-4-pyridyl)-4-(cinnamoylaminomethyl)benzamide

M-14 (0.281 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the preparation of product V in Method one to obtain 0.209 g of a white solid, with a yield of 56.1%.

MS(ES+):m/e 373.14

¹H-NMR (400 MHz, DMSO-d₆) δppm: 4.22 (2H, s, —CH₂), 6.66 (1H, d, Ar—H), 6.84 (1H, d, —CH=CH—), 7.24 (2H, d, Ar—H), 7.47 (5H, s, 7.49 (1H, d, Ar—H), 7.55 (1H, d, —CH=CH—), 7.83 (2H, d, Ar—H), 8.38 (1H, d, Ar—H), 10.28 (1H, s, —C(=O)—NH—), 10.22 (1H, s, —C(=O)—NH—), 5.89 (2H, s, —NH₂).

EXAMPLE 27

V-29 N-(2-amino-3-pyridyl)-4-[(4-methylcinnamoyl)aminomethyl]benzamide

P-methylcinnamic acid (1.62 g, 10 mmol), thionylchloride (4.72 g, 40 mmol), dichloromethane (10 ml), p-aminobenzoic acid (1.52 g, 10 mmol), and 10 ml of 1 mol/L sodium hydroxide are used according to the method for the production of compound III in Method one to obtain 2.68 g of 4-[(4-methylcinnamoyl)aminomethyl]benzoic acid (intermediate M-15) as a white solid, with a yield of 91.0%.

MS(ES+):m/e 312.12.

M-15 (0.295 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the preparation of product V in Method one to obtain 0.197 g of a white solid, with a yield of 51.0%.

MS(ES+):m/e387.18.

¹H-NMR (400 MHz, DMSO-d₆) δppm: 2.43 (3H, s, —CH₃), 4.29 (2H, s, —CH₂), 6.64 (1H, dd, Ar—H), 6.88 (1H, d, —CH=CH—), 6.95 (1H, d, Ar—H), 7.19 (2H, d, Ar—H), 7.24 (2H, d, Ar—H), 7.39 (2H, d, Ar—H), 7.55 (1H, d, —CH=CH—), 7.75 (1H, d, Ar—H), 7.83 (2H, d, Ar—H), 10.28 (1H, s, —C(=O)—NH—), 10.22 (1H, s, —C(=O)—NH—), 5.79 (2H, s, —NH₂).

EXAMPLE 28

V-30 N-(2-amino-4-pyridyl)-4-[(4-methylcinnamoyl)aminomethyl]benzamide

M-15 (0.295 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain of 0.192 g of a white solid, with a yield of 49.7%.

MS(ES+):m/e 387.17.

¹H-NMR (400 MHz, DMSO-d₆) δppm: 2.41 (3H, s, —CH₃), 4.29 (2H, s, —CH₂), 6.66 (1H, d, Ar—H), 6.84 (1H, d, —CH=CH—), 6.95 (1H, d, Ar—H), 7.18 (2H, d, Ar—H), 7.24 (2H, d, Ar—H), 7.39 (2H, d, Ar—H), 7.55 (1H, d, —CH=CH—), 7.83 (2H, d, Ar—H), 8.38 (1H, d, Ar—H), 10.28 (1H, s, —C(=O)—NH—), 10.22 (1H, s, —C(=O)—NH—), 5.79 (2H, s, —NH₂).

EXAMPLE 29

V-31 N-(2-amino-3-pyridyl)-4-[(4-methoxycinnamoyl)aminomethyl]benzamide

P-methoxycinnamate (1.78 g, 10 mmol), thionylchloride (4.72 g, 40 mmol), dichloromethane (10 ml), p-aminobenzoic acid (1.52 g, 10 mmol), and 10 ml of 1 mol/L sodium hydroxide are used according to the method for the production of intermediate III in Method one to obtain 2.80 g of 4-[(4-methoxycinnamoyl)aminomethyl]benzoic acid (intermediate M-16) as a white solid, with a yield of 90.0%.

M-16 (0.311 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.197 g of a white solid, with a yield of 48.9%.

MS(ES+):m/e403.18.

¹H-NMR (400 MHz, DMSO-d₆) δppm: 3.85 (3H, s, —OCH₃), 4.22 (2H, s, —CH₂), 6.64 (1H, dd, Ar—H), 6.84 (1H, d, —CH=CH—), 6.95 (1H, d, Ar—H), 7.09 (2H, d, Ar—H), 7.24 (2H, d, Ar—H), 7.55 (1H, d, —CH=CH—), 7.68 (2H, d, Ar—H), 7.75 (1H, d, Ar—H), 7.83 (2H, d, Ar—H), 10.30 (1H, s, —C(=O)—NH—), 10.35 (1H, s, —C(=O)—NH—), 5.87 (2H, s, —NH₂).

EXAMPLE 30

V-32 N-(2-amino-4-pyridyl)-4-[(4-methoxycinnamoyl)aminomethyl]benzamide

M-16 (0.311 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.192 g of a white solid, with a yield of 47.7%.

MS(ES+):m/e 403.17.

¹H-NMR (400 MHz, DMSO-d₆) δppm: 3.85 (3H, s, —OCH₃), 4.32 (2H, s, —CH₂), 6.66 (1H, d, Ar—H), 6.90 (1H, d, —CH=CH—), 6.95 (1H, d, Ar—H), 7.09 (2H, d, Ar—H), 7.27 (2H, d, Ar—H), 7.57 (1H, d, —CH=CH—), 7.68 (2H, d, Ar—H), 7.83 (2H, d, Ar—H), 8.38 (1H, d, Ar—H), 10.30 (1H, s, —C(=O)—NH—), 10.43 (1H, s, —C(=O)—NH—), 5.87 (2H, s, —NH₂).

EXAMPLE 31

V-33 N-(2-hydroxy-5-pyridyl)-4-[(3,4,5-trimethoxycinnamoyl)aminomethyl]benzamide 3,4,5-trimethoxycinnamic acid (2.38 g, 10 mmol), thionyichloride (4.72 g, 40 mmol), dichloromethane (10 ml), p-aminobenzoic acid (1.52 g, 10 mmol), and 10 ml of 1 mol/L sodium hydroxide are used according to the method for the production of compound III in Method one to obtain 3.39 g of 4-[(3,4,5-trimethoxycinnamoyl)aminomethyl]bennzoic acid (intermediate M-17) as a white solid, with a yield of 91.2%.

M-17 (0.371 g, 1 mmol), 3-amino-4-hydroxypyridine (0.110 g, 1 mmol), HBTU (0.379 g, 1 mmol), N,N-dimethylformamide (10 ml), and triethylamine (0.404 g, 4 mmol) are used according to the method for the production of product V in Method one to obtain 3.02 g of a white solid, with a yield of 63.4%.

MS(ES+):m/e 379.17

¹H-NMR (400 MHz, DMSO-d₆) δppm: 3.71 (3H, s, —OCH₃), 3.83 (6H, s, —OCH₃), 4.31 (2H, s, —CH₂), 6.78 (2H, s, Ar—H), 6.84 (1H, d, —CH=CH—), 6.87 (1H, d, Ar—H), 7.24 (2H, d, Ar—H), 7.57 (1H, d, —CH=CH—), 7.83 (2H, d, Ar—H), 8.06 (1H, d, Ar—H), 8.36 (1H, s, Ar—H), 10.32 (1H, s, —C(=O)—NH—), 10.43 (1H, s, —C(=O)—NH—), 9.89 (2H, s, —NH₂).

EXAMPLE 32

V-34 N-(2-pyridyl)-4-[(3,4,5-trimethoxycinnamoyl)aminomethyl]benzamide

M-17 (0.371 g, 1 mmol), 2-aminopyridine (0.094 g, 1 mmol), HBTU (0.379 g, 1 mmol), N,N-dimethylformamide (10 ml), and triethylamine (0.202 g, 2 mmol) are used according to the method for the production of product V in Method one to obtain 0.288 g of a white solid, with a yield of 64.5%.

MS(ES+):m/e 448.19.

¹H-NMR (400 MHz, DMSO-d₆) δppm: 3.71 (3H, s, —OCH₃), 3.83 (6H, s, —OCH₃), 4.21 (2H, s, —CH₂), 6.70 (1H, d, Ar—H), 6.73 (1H, dd, Ar—H), 6.78 (2H, s, Ar—H), 6.84 (1H, d, —CH=CH—), 7.24 (2H, d, Ar—H), 7.39 (1H, dd, Ar—H), 7.55 (1H, d, —CH=CH—), 7.83 (2H, d, Ar—H), 7.98 (1H, d, Ar—H), 10.32 (1H, s, —C(=O)—NH—), 10.43 (1H, s, —C(=O)—NH—).

EXAMPLE 33

V-35 N-(3-pyridyl)-4-[(3,4,5-trimethoxycinnamoyl)aminomethyl]benzamide

M-17 (0.371 g, 1 mmol), 2-aminopyridine (0.094 g, 1 mmol), HBTU 0 (0.379 g, 1 mmol), N,N-dimethylformamide (10 ml), and triethylamine (0.202 g, 2 mmol) are used according to the method for the production of product V in Method one to obtain 0.288 g of a white solid, with a yield of 56.3%.

MS(ES+):m/e 448.16.

¹H-NMR (400 MHz, DMSO-d₆) δppm: 3.71 (3H, s, —OCH₃), 3.83 (6H, s, —OCH₃), 4.26 (2H, s, —CH₂), 6.78 (2H, s, Ar—H), 6.84 (1H, d, —CH=CH—), 7.24 (2H, d, Ar—H), 7.41 (1H, dd, Ar—H), 7.55 (1H, d, —CH=CH—), 7.83 (2H, d, Ar—H), 7.92 (1H, d, Ar—H), 8.18 (1H, d, Ar—H), 8.93 (1H, d, Ar—H), 10.32 (1H, s, —C(=O)—NH—), 10.43 (1H, s, —C(=O)—NH—).

EXAMPLE 34

V-36 N-(2-amino-3-pyridyl)-4-[(3,4,5-trimethoxycinnamoyl)aminomethyl]benzamide

M-17 (0.311 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.205 g of a white solid, with a yield of 44.3%.

MS(ES+):m/e 463.17.

¹H-NMR (400 MHz, DMSO-d₆) δppm: 3.71 (3H, s, —OCH₃), 3.83 (6H, s, —OCH₃), 4.27 (2H, s, —CH₂), 6.64 (1H, dd, Ar—H), 6.78 (2H, s, Ar—H), 6.84 (1H, d, —CH=CH—), 6.95 (1H, d, Ar—H), 7.24 (2H, d, Ar—H), 7.55 (1H, d, —CH=CH—), 7.75 (1H, d, Ar—H), 7.83 (2H, d, Ar—H), 10.32 (1H, s, —C(=O)—NH—), 10.43 (1H, s, —C(=O)—NH—), 5.89 (2H, s, —NH₂).

EXAMPLE 35

V-37 N-(2-amino-4-pyridyl)-4-[(3,4,5-trimethoxycinnamoyl)aminomethyl]benzamide

M-17 (0.311 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.213 g of a white solid, with a yield of 46.1%.

MS(ES+):m/e 463.12.

¹H-NMR (400 MHz, DMSO-d₆) δppm: 3.71 (3H, s, —OCH₃), 3.83 (6H, s, —OCH₃), 4.25 (2H, s, —CH₂), 6.66 (1H, d, Ar—H), 6.78 (2H, s, Ar—H), 6.84 (1H, d, —CH=CH—), 7.24 (2H, d, Ar—H), 7.49 (1H, d, Ar—H), 7.55 (1H, d, —CH=CH—), 7.83 (2H, d, Ar—H), 8.38 (1H, s, Ar—H), 10.32 (1H, s, —C(=O)—NH—), 10.43 (1H, s, —C(=O)—NH—), 5.89 (2H, s, —NH₂).

EXAMPLE 36

V-38 N-(2-amino-3-pyridyl)-4-[(4-nitrocinnamoyl)aminomethyl]benzamide

P-nitrocinnamic acid (1.93 g, 10 mmol), thionylchloride (9.44 g, 80 mmol), dichloromethane (10 ml), p-aminobenzoic acid (1.52 g, 10 mmol), and 10 ml of 1 mol/L sodium hydroxide are used according to the method for the production of compound III in Method one to obtain 0.277 g of 4-[(4-nitrocinnamoyl)aminomethyl]benzoic acid (M-18) yellow solid, with a yield of 85.1%.

M-18 (0.426 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.180 g of yellow solid, with a yield of 43.2%.

MS(ES+):m/e 418.12.

¹H-NMR (400 MHz, DMSO-d₆) δppm: 4.22 (2H, s, —CH₂), 6.64 (1H, dd, Ar—H), 7.56 (2H, d, Ar—H), 8.14 (2H, d, Ar—H), 6.95 (1H, d, Ar—H), 7.23 (1H, d, —CH=CH—), 7.24 (2H, d, Ar—H), 7.69 (1H, d, —CH=CH—), 7.75 (1H, d, Ar—H), 7.83 (2H, d, Ar—H), 10.32 (1H, s, —C(=O)—NH—), 10.43 (1H, s, —C(=O)—NH—), 5.89 (2H, s, —NH$_2$).

EXAMPLE 37

V-39 N-(2-amino-3-pyridyl)-4-[(4-aminocinnamoyl) aminomethyl]benzamide

Dissolving V-38 (0.419 g, 1 mmol) into methanol, adding stannous chloride dihydrate (0.678 g, 3 mmol), refluxing 2 hours, and then concentrating methanol. The residue is poured into ice-water, and a saturated solution of potassium carbonate is added to adjust pH to about 9. Extracting with dichloromethane and drying over anhydrous magnesium sulfate overnight. After concentrating the solvent, the product is recrystallized with ethyl acetate, to obtain 0.253 g of a white solid, with a yield of 65.3%.

MS(ES+):m/e 388.18.

$^1$H-NMR (400 MHz, DMSO-d$_6$) δppm: 4.22 (2H, s, —CH$_2$), 6.64 (1H, dd, Ar—H), 6.41 (2H, d, Ar—H), 7.06 (2H, d, Ar—H), 6.95 (1H, d, Ar—H), 7.24 (2H, d, Ar—H), 7.55 (1H, d, —CH=CH—), 6.84 (1H, d, —CH=CH—), 7.75 (1H, d, Ar—H), 7.83 (2H, d, Ar—H), 10.32 (1H, s, —C(=O)—NH—), 10.43 (1H, s, —C(=O)—NH—), 5.89 (2H, s, —NH$_2$), 6.51 (2H, s, —NH$_2$).

EXAMPLE 38

V-40 N-(2-amino-4-pyridyl)-4-[(4-nitrocinnamoyl) aminomethyl]benzamide

M-18 (0.426 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.176 g of a yellow solid, with a yield of 42.3%.

MS(ES+):m/e 418.14.

$^1$H-NMR (400 MHz, DMSO-d$_6$) δppm: 4.26 (2H, s, —CH$_2$), 6.66 (1H, d, Ar—H), 7.13 (1H, d, —CH=CH—), 7.24 (2H, d, Ar—H), 7.49 (1H, d, Ar—H), 7.56 (2H, d, Ar—H), 7.69 (1H, d, —CH=CH—), 7.83 (2H, d, Ar—H), 8.14 (2H, d, Ar—H), 8.38 (1H, s, Ar—H), 10.32 (1H, s, —C(=O)—NH—), 10.43 (1H, s, —C(=O)—NH—), 5.89 (2H, s, —NH$_2$).

EXAMPLE 39

V-41 N-(2-amino-4-pyridyl)-4-[4-aminocinnamoyl) aminomethyl]benzamide

Dissolving V-40 (0.419 g, 1 mmol) in methanol, adding stannous chloride dihydrate (0.678 g, 3 mmol), refluxing 2 hours, and then concentrating methanol. The residue is poured into ice-water, and a saturated solution of potassium carbonate is added to adjust pH to 9. Extracting with dichloromethane and drying over anhydrous magnesium sulfate overnight. After concentrating the solvent, the product is recrystallized with ethyl acetate, to obtain 0.249 g of a yellow solid, with a yield of 64.2%.

MS(ES+):m/e 388.17.

$^1$H-NMR (400 MHz, DMSO-d$_6$) δppm: 4.19 (2H, s, —CH$_2$), 6.41 (2H, d, Ar—H), 6.66 (1H, d, Ar—H), 6.84 (1H, d, —CH=CH—), 7.05 (2H, d, Ar—H), 7.49 (1H, d, Ar—H), 7.55 (1H, d, —CH=CH—), 7.83 (2H, d, Ar—H), 8.14 (2H, d, Ar—H), 8.38 (1H, s, Ar—H), 10.32 (1H, s, —C(=O)—NH—), 10.43 (1H, s, —C(=O)—NH—), 5.89 (2H, s, —NH$_2$), 5.97 (2H, s, —NH$_2$).

EXAMPLE 40

V-42 N-(2-amino-3-pyridyl)-4-[(4-fluorocinnamoyl) aminomethyl]benzamide

P-fluorocinnamic acid (1.66 g, 10 mmol), thionylchloride (4.72 g, 40 mmol), dichloromethane (10 ml), p-aminobenzoic acid (1.52 g, 10 mmol), and 10 ml of 1 mol/L sodium hydroxide are used according to the method for the production of compound III in Method two to obtain 2.71 g of 4-[(4-fluorocinnamoyl)aminomethyl]benzoic acid (intermediate M-19) as a white solid, with a yield of 90.5%.

M-19 (0.299 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 1.83 g of a white solid, with a yield of 47.0%.

MS(ES+):m/e 391.12.

$^1$H-NMR (400 MHz, DMSO-d$_6$) δppm: 4.22 (2H, s, —CH$_2$), 6.64 (1H, dd Ar—H), 6.84 (1H, d, —CH=CH—), 6.95 (1H, d, Ar—H), 7.24 (2H, d, Ar—H), 7.28 (2H, d, Ar—H), 7.40 (2H, d, Ar—H), 7.55 (1H, d, —CH=CH—), 7.75 (1H, d, Ar—H), 7.83 (2H, d, Ar—H), 10.32 (1H, s, —C(=O)—NH—), 10.43 (1H, s, —C(=O)—NH—), 5.89 (2H, s, —NH$_2$).

EXAMPLE 41

V-43 N-(2-amino-4-pyridyl)-4-[(4-fluorocinnamoyl) aminomethyl]benzamide

M-19 (0.299 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.178 g of a white solid, with a yield of 45.7%.

MS(ES+):m/e 391.12.

$^1$H-NMR (400 MHz, DMSO-d$_6$) δppm: 4.18 (2H, s, —CH$_2$), 7.40 (2H, d, Ar—H), 6.66 (1H, d, Ar—H), 6.84 (1H, d, —CH=CH—), 7.28 (2H, d, Ar—H), 7.24 (2H, d, Ar—H), 7.49 (1H, d, Ar—H), 7.55 (1H, d, —CH=CH—), 7.83 (2H, d, Ar—H), 8.38 (1H, s, Ar—H), 10.32 (1H, s, —C(=O)—NH—), 10.43 (1H, s, —C(=O)—NH—), 5.89 (2H, s, —NH$_2$).

EXAMPLE 42

V-44 N-(2-amino-3-pyridyl)-4-[(3-pyridylacryloyl) aminomethyl]benzamide

Dissolving 3-pyridylacrylic acid (1.49 g, 10 mmol) and HBTU (3.79 g, 10 mmol) into 10 ml of acetonitrile, drop-adding triethylamine (2.02 g, 20 mmol), stirring at room temperature 30 minutes, to obtain a yellow sticky liquid. Dissolving p-aminobenzoic acid (1.52 g, 10 mmol) in 10 ml of 1 mol/L sodium hydroxide aqueous solution, and thereto drop-adding the above yellow sticky liquid at 60° C. After completion of drop-addition, maintaining the temperature for 1 hour to complete the reaction. The reaction solution is adjusted to pH of about 7 with concentrated hydrochloric acid. Large amount of solids are precipitated, filtrated and dried to obtain 1.90 g of 4-[(3-pyridylacryloyl)aminomethyl] benzoic acid (intermediate M-20) as a white solid, with a yield of 67.6%.

M-20 (0.282 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.201 g of a white solid, with a yield of 53.7%.

MS(ES+):m/e 374.12.

¹H-NMR (400 MHz, DMSO-d$_6$) δppm: 4.22 (2H, s, —CH$_2$), 6.64 (1H, dd, Ar—H), 6.84 (1H, d, —CH=CH—), 6.95 (1H, d, Ar—H), 7.24 (2H, d, Ar—H), 7.56 (1H, dd, Ar—H), 7.79 (1H, d, Ar—H), 7.55 (1H, d, —CH=CH—), 7.75 (1H, d, Ar—H), 7.83 (2H, d, Ar—H), 8.39 (1H, d, Ar—H), 10.32 (1H, s, —C(=O)—NH—), 10.43 (1H, s, —C(=O)—NH—), 5.89 (2H, s, —NH$_2$).

EXAMPLE 43

V-45 N-(2-amino-4-pyridyl)-4-[(3-pyridylacryloyl) aminomethyl]benzamide

M-20 (0.282 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.194 g of a white solid, with a yield of 52.1%.

MS(ES+):m/e 374.15.

¹H-NMR (400 MHz, DMSO-d$_6$) δppm: 4.30 (2H, s, —CH$_2$), 6.66 (1H, dd, Ar—H), 6.84 (1H, d, —CH=CH—), 7.24 (2H, d, Ar—H), 7.56 (1H, dd, Ar—H), 7.79 (1H, d, Ar—H), 7.55 (1H, d, —CH=CH—), 7.49 (1H, dd, Ar—H), 7.83 (2H, d, Ar—H), 8.38 (1H, s, Ar—H), 8.39 (1H, d, Ar—H), 10.32 (1H, s, —C(=O)—NH—), 10.43 (1H, s, —C(=O)—NH—), 5.89 (2H, s, —NH$_2$).

EXAMPLE 44

V-46 N-(2-amino-3-pyridyl)-4-(4-phenylcinnamoy-laminomethyl)benzamide 4-phenylcinnamic acid (2.24 g, 10 mmol), thionylchloride (4.72 g, 40 mmol), dichloromethane (10 ml), p-aminobenzoic acid (1.52 g, 10 mmol), and 10 ml of 1 mol/L sodium hydroxide are used according to the method for the production of compound III in Method two to obtain 2.78 g of 4-(phenylcinnamoylaminomethyl)benzoic acid (intermediate M-21) as a white solid, with a yield of 77.9%.

M-21 (0.357 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.245 g of a white solid, with a yield of 54.6%.

MS(ES+):m/e 449.12.

¹H-NMR (400 MHz, DMSO-d$_6$) δppm: 4.27 (2H, s, —CH$_2$), 6.64 (1H, dd, Ar—H), 6.84 (1H, d, —CH=CH—), 6.95 (1H, d, Ar—H), 7.24 (2H, d, 7.36 (2H, d, Ar—H), 7.48 (5H, s, Ar—H), 7.59 (2H, d, Ar—H), 7.55 (1H, d, —CH=CH—), 7.75 (1H, d, 7.83 (2H, d, Ar—H), 10.32 (1H, s, —C(=O)—NH—), 10.43 (1H, s, —C(=O)—NH—), 5.89 (2H, s, —NH$_2$).

EXAMPLE 45

V-47 N-(2-amino-4-pyridyl)-4-(4-phenylcinnamoy-laminomethyl)benzamide

M-21 (0.357 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.229 g of a white solid, with a yield of 51.1%.

MS(ES+):m/e 449.14

¹H-NMR (400 MHz, DMSO-d$_6$) δppm: 4.24 (2H, s, —CH$_2$), 6.66 (1H, d, Ar—H), 6.84 (1H, d, —CH=CH—), 7.24 (2H, d, Ar—H), 7.36 (2H, d, Ar—H), 7.47 (5H, s, Ar—H), 7.49 (1H, dd, Ar—H), 7.55 (1H, d, —CH=CH—), 7.59 (2H, d, Ar—H), 7.83 (2H, d, Ar—H), 8.38 (1H, s, Ar—H), 8.39 (1H, d, Ar—H), 10.32 (1H, s, —C(=O)—NH—), 10.43 (1H, s, —C(=O)—NH—), 5.89 (2H, s, —NH$_2$).

EXAMPLE 46

V-48 N-(2-amino-3-pyridyl)-4-(2-naphthylacryloy-laminomethyl)benzamide 2-naphthylacrylic acid (1.98 g, 10 mmol), thionylchloride (4.72 g, 40 mmol), dichloromethane (10 ml), p-aminobenzoic acid (1.52 g, 10 mmol), and 10 ml of 1 mol/L sodium hydroxide are used according to the method for the production of compound III in Method one to obtain 2.78 g of 4-(2-naphthylacryloylaminomethyl)benzoic acid (intermediate M-22) as a white solid, with a yield of 77.9%.

M-22 (0.331 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.231 g of a white solid, with a yield of 54.6%.

MS(ES+):m/e 423.12.

¹H-NMR (400 MHz, DMSO-d$_6$) δppm: 4.22 (2H, s, —CH$_2$), 6.64 (1H, dd, Ar—H), 6.84 (1H, d, —CH=CH—), 6.95 (1H, d, Ar—H), 7.24 (2H, d, Ar—H), 7.36 (1H, d, Ar—H), 7.55 (1H, d, —CH=CH—), 7.58 (1H, dd, Ar—H), 7.59 (1H, dd, Ar—H), 7.75 (1H, d, Ar—H), 7.71 (1H, s, Ar—H), 7.67 (1H, d, Ar—H), 7.75 (1H, d, Ar—H), 7.83 (2H, d, Ar—H), 8.01 (1H, d, Ar—H), 10.32 (1H, s, —C(=O)—NH—), 10.43 (1H, s, —C(=O)—NH—), 5.89 (2H, s, —NH$_2$).

EXAMPLE 47

V-49 N-(2-amino-3-pyridyl)-4-(2-naphthylacryloy-laminonnethyl)benzamide

M-22 (0.331 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.216 g of a white solid, with a yield of 51.1%.

MS(ES+):m/e 423.14

¹H-NMR (400 MHz, DMSO-d$_6$) δppm: 4.26 (2H, s, —CH$_2$), 6.66 (1H, d, Ar—H), 6.84 (1H, d, —CH=CH—), 7.24 (2H, d, Ar—H), 7.36 (1H, d, Ar—H), 7.55 (1H, d, —CH=CH—), 7.58 (1H, dd, Ar—H), 7.59 (1H, dd, Ar—H), 7.49 (1H, d, Ar—H), 7.71 (1H, s, Ar—H), 7.67 (1H, d, Ar—H), 7.75 (1H, d, Ar—H), 7.83 (2H, d, Ar—H), 8.01 (1H, d, Ar—H), 8.38 (1H, s, Ar—H), 10.32 (1H, s, —C(=O)—NH—), 10.43 (1H, s, —C(=O)—NH—), 5.89 (2H, s, —NH$_2$).

EXAMPLE 48

V-50 N-(2-amino-3-pyridyl)-4-[(3-phenylpropionyl) aminomethyl]benzamide 3-phenylpropionic acid (1.50 g, 10 mmol), thionylchloride (4.72 g, 40 mmol), dichloromethane (10 ml), p-aminobenzoic acid (1.52 g, 10 mmol), and 10 ml of 1 mol/L sodium hydroxide are used according to the method for the production of compound III in Method one to obtain 2.73 g of 4-[(3-phenylpropionyl)aminomethyl]benzoic acid (intermediate M-23) as a yellow solid, with a yield of 96.1%.

M-23 (0.283 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.199 g of a white solid, with a yield of 53.4%.
MS(ES+):m/e 375.12.
$^1$H-NMR (400 MHz, DMSO-d$_6$) δppm: 2.51 (2H, t, —CH$_2$), 2.80 (2H, t, —CH$_2$), 4.24 (2H, s, —CH$_2$), 6.64 (1H, dd, Ar—H), 6.95 (1H, d, Ar—H), 7.28 (2H, d, Ar—H), 7.30 (5H, s, Ar—H), 7.75 (1H, d, Ar—H), 7.83 (2H, d, Ar—H), 10.32 (1H, s, —C(=O)—NH—), 10.43 (1H, s, —C(=O)—NH—), 5.89 (2H, s, —NH$_2$).

EXAMPLE 49

V-51 N-(2-amino-4-pyridyl)-4-[(3-phenylpropionyl) aminomethyl]benzamide

M-23 (0.283 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.183 g of a white solid, with a yield of 49.0%.
MS(ES+):m/e 375.12.
$^1$H-NMR (400 MHz, DMSO-d$_6$) δppm: 2.51 (2H, t, —CH$_2$), 2.80 (2H, t, —CH$_2$), 4.24 (2H, s, —CH$_2$), 6.66 (1H, d, Ar—H), 7.24 (2H, d, Ar—H), 7.30 (5H, s, Ar—H), 7.49 (1H, d, Ar—H), 7.83 (2H, d, Ar—H), 8.38 (1H, s, Ar—H), 10.32 (1H, s, —C(=O)—NH—), 10.43 (1H, s, —C(=O)—NH—), 5.89 (2H, s, —NH$_2$).

EXAMPLE 50

V-52 N-(2-amino-3-pyridyl)-4-[3-(4-methylphenyl) propionylaminomethyl]benzamide

P-methylphenylpropionic acid (1.64 g, 10 mmol), thionylchloride (4.72 g, 40 mmol), dichloromethane (10 ml), p-aminobenzoic acid (1.52 g, 10 mmol), 10 ml of 1 mol/L sodium hydroxide are used according to the method for the production of compound III in Method one to obtain 2.68 g of 4-[3-(4-methylphenyl)propionylaminomethyl]benzoic acid (intermediate M-24) as a white solid, with a yield of 90.1%.
M-24 (0.297 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.199 g of a white solid, with a yield of 51.3%.
MS(ES+):m/e 389.12.
$^1$H-NMR (400 MHz, DMSO-d$_6$) δppm: 2.23 (3H, s, —CH$_3$), 2.51 (2H, t, —CH$_2$), 2.80 (2H, t, —CH$_2$), 4.24 (2H, s, —CH$_2$), 6.64 (1H, dd, Ar—H), 6.95 (1H, d, Ar—H), 7.24 (2H, d, Ar—H), 7.00 (2H, d, Ar—H), 7.05 (2H, d, Ar—H), 7.75 (1H, d, Ar—H), 7.83 (2H, d, Ar—H), 10.78 (1H, s, —C(=O)—NH—), 10.43 (1H, s, —C(=O)—NH—), 5.66 (2H, s, —NH$_2$).

EXAMPLE 51

V-53 N-(2-amino-4-pyridyl)-4-[3-(4-methylphenyl) propionylaminomethyl]benzamide

M-24 (0.297 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.185 g of a white solid, with a yield of 47.9%.
MS(ES+):m/e 389.12.
$^1$H-NMR (400 MHz, DMSO-d$_6$) δppm: 2.19 (3H, s, —CH$_3$), 2.51 (2H, t, —CH$_2$), 2.80 (2H, t, —CH$_2$), 4.24 (2H, s, —CH$_2$), 6.66 (1H, d, Ar—H), 7.24 (2H, d, Ar—H), 7.00 (2H, d, Ar—H), 7.05 (2H, d, Ar—H), 7.49 (1H, d, Ar—H), 7.83 (2H, d, Ar—H), 8.38 (1H, s, Ar—H), 10.32 (1H, s, —C(=O)—NH—), 10.43 (1H, s, —C(=O)—NH—), 5.89 (2H, s, —NH$_2$).

EXAMPLE 52

V-54 N-(2-amino-3-pyridyl)-4-[3-(4-methoxyphenyl)propionylaminomethyl]benzamide

P-methoxyphenylpropionic acid (1.80 g, 10 mmol), thionylchloride (4.72 g, 40 mmol), dichloromethane (10 ml), p-aminobenzoic acid (1.52 g, 10 mmol), and 10 ml of 1 mol/L sodium hydroxide are used according to the method for the production of compound III in Method one to obtain 2.82 g of 4-[3-(4-methoxyphenyl)propionylaminomethyl]benzoic acid (intermediate M-25) as a white solid, with a yield of 90.1%.
M-25 (0.313 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.208 g of a white solid, with a yield of 51.3%.
MS(ES+):m/e 405.12.
$^1$H-NMR (400 MHz, DMSO-d$_6$) δppm: 2.51 (2H, t, —CH$_2$), 2.80 (2H, t, —CH$_2$), 3.84 (3H, s, —OCH$_3$), 4.24 (2H, s, —CH$_2$), 6.64 (1H, dd, Ar—H), 6.95 (1H, d, Ar—H), 7.24 (2H, d, Ar—H), 6.72 (2H, d, Ar—H), 7.05 (2H, d, Ar—H), 7.75 (1H, d, Ar—H), 7.83 (2H, d, Ar—H), 10.32 (1H, s, —C(=O)—NH—), 10.43 (1H, s, —C(=O)—NH—), 5.89 (2H, s, —NH$_2$).

EXAMPLE 53

V-55 N-(2-amino-4-pyridyl)-4-[3-(4-methoxyphenyl)propionylaminomethyl]benzamide

M-25 (0.313 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.214 g of a white solid, with a yield of 52.9%.
MS(ES+):m/e 405.12.
$^1$H-NMR (400 MHz, DMSO-d$_6$) δppm: 2.51 (2H, t, —CH$_2$), 2.80 (2H, t, —CH$_2$), 3.84 (3H, s, —OCH$_3$), 4.24 (2H, s, —CH$_2$), 6.66 (1H, d, Ar—H), 7.24 (2H, d, Ar—H), 6.72 (2H, d, Ar—H), 7.05 (2H, d, Ar—H), 7.49 (1H, d, Ar—H), 7.83 (2H, d, Ar—H), 8.38 (1H, s, Ar—H), 10.32 (1H, s, —C(=O)—NH—), 10.43 (1H, s, —C(=O)—NH—), 5.89 (2H, s, —NH$_2$).

EXAMPLE 54

V-56 N-(2-amino-3-pyridyl)-4-[3-(3,4,5-methoxyphenyl)propionylaminomethyl]benzamide 3,4,5-trimethoxyphenylpropionic acid (2.40 g, 10 mmol), thionylchloride (4.72 g, 40 mmol), dichloromethane (10 ml), p-aminobenzoic acid (1.52 g, 10 mmol), and 10 ml of 1 mol/L sodium hydroxide are used according to the method for the production of compound III in Method one to obtain 3.04 g of 4-[3-(3,4,5-methoxyphenyl)propionylaminomethyl]benzoic acid (intermediate M-26) as a white solid, with a yield of 81.7%.
M-26 (0.373 g 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.202 g of a white solid, with a yield of 43.5%.

MS(ES+):m/e 465.21.

$^1$H-NMR (400 MHz, DMSO-d$_6$) δppm: 2.51 (2H, t, —CH$_2$), 2.80 (2H, t, —CH$_2$), 3.84 (3H, s, —OCH$_3$), 3.89 (6H, s, —OCH$_3$), 4.27 (2H, s, —CH$_2$), 6.64 (1H, dd, Ar—H), 6.95 (1H, d, Ar—H), 7.24 (2H, d, Ar—H), 6.33 (2H, s, Ar—H), 7.75 (1H, d, Ar—H), 7.83 (2H, d, Ar—H), 10.32 (1H, s, —C(=O)—NH—), 10.43 (1H, s, —C(=O)—NH—), 5.89 (2H, s, —NH$_2$).

EXAMPLE 55

V-57 N-(2-amino-4-pyridyl)-4-[3-(3,4,5-methoxyphenyl)propionylaminomethyl]benzamide M-26 (0.373 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.204 g of a white solid, with a yield of 44.0%.

MS(ES+):m/e 465.21.

$^1$H-NMR (400 MHz, DMSO-d$_6$) δppm: 2.51 (2H, t, —CH$_2$), 2.80 (2H, t, —CH$_2$), 3.84 (3H, s, —OCH$_3$), 3.89 (6H, s, —OCH$_3$), 4.24 (2H, s, —CH$_2$), 6.66 (1H, d, Ar—H), 7.24 (2H, d, Ar—H), 6.33 (2H, s, Ar—H), 7.49 (1H, d, Ar—H), 7.83 (2H, d, Ar—H), 8.38 (1H, s, Ar—H), 10.32 (1H, s, —C(=O)—NH—), 10.43 (1H, s, —C(=O)—NH—), 5.89 (2H, s, —NH$_2$).

EXAMPLE 56

V-58 N-(2-amino-3-pyridyl)-4-[3-(4-nitrophenyl)propionylaminomethyl]benzamide

P-nitrophenylpropionic acid (1.95 g, 10 mmol), thionylchloride (9.44 g, 80 mmol), p-aminobenzoic acid (1.52 g, 10 mmol), and 10 ml of 1 mol/L sodium hydroxide are used according to the method for the production of compound III in Method two to obtain 2.69 g of 4-[3-(4-nitrophenyl)propionylaminomethyl]benzoic acid (intermediate M-27) as a white solid, with a yield of 82.0%.

M-27 (0.328 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.181 g of a yellow solid, with a yield of 43.2%.

MS(ES+):m/e 420.16.

$^1$H-NMR (400 MHz, DMSO-d$_6$) δppm: 2.51 (2H, t, —CH$_2$), 2.80 (2H, t, —CH$_2$), 4.24 (2H, s, —CH$_2$), 6.64 (1H, dd, Ar—H), 6.95 (1H, d, Ar—H), 7.24 (2H, d, Ar—H), 7.38 (2H, d, Ar—H), 7.75 (1H, d, Ar—H), 8.24 (2H, d, Ar—H), 7.83 (2H, d, Ar—H), 10.32 (1H, s, —C(=O)—NH—), 10.43 (1H, s, —C(=O)—NH—), 5.89 (2H, s, —NH$_2$).

EXAMPLE 57

V-59 N-(2-amino-3-pyridyl)-4-[3-(4-aminophenyl)propionylaminomethyl]benzamide

Dissolving V-58 (0.419 g, 1 mmol) into methanol, adding stannous chloride dihydrate (0.678 g, 3 mmol), refluxing 2 hours, and then concentrating methanol. The residue is poured into ice-water, and a saturated solution of potassium carbonate is added to adjust pH to 9. Extracting with dichloromethane and drying over anhydrous magnesium sulfate overnight. After concentrating solvent, the product is recrystallized with ethyl acetate, to obtain 0.203 g of a yellow solid, with a yield of 52.1%.

MS(ES+):m/e 390.19.

$^1$H-NMR (400 MHz, DMSO-d$_6$) δppm: 2.51 (2H, t, —CH$_2$), 2.80 (2H, t, —CH$_2$), 4.24 (2H, s, —CH$_2$), 6.64 (1H, dd, Ar—H), 6.87 (2H, d, Ar—H), 6.95 (1H, d, Ar—H), 7.24 (2H, d, Ar—H), 6.41 (2H, d, Ar—H), 7.75 (1H, d, Ar—H), 7.83 (2H, d, Ar—H), 10.32 (1H, s, —C(=O)—NH—), 10.43 (1H, s, —C(=O)—NH—), 5.89 (2H, s, —NH$_2$), 5.97 (2H, s, —NH$_2$).

EXAMPLE 58

V-60 N-(2-amino-4-pyridyl)-4-[3-(4-nitrophenyl)propionylaminomethyl]benzamide

M-27 (0.328 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.179 g of a white solid, with a yield of 42.8%.

MS(ES+):m/e 420.12.

$^1$H-NMR (400 MHz, DMSO-d$_6$) δppm: 2.54 (2H, t, —CH$_2$), 2.87 (2H, t, —CH$_2$), 4.29 (2H, s, —CH$_2$), 6.66 (1H, d, Ar—H), 7.24 (2H, d, Ar—H), 7.36 (2H, d, Ar—H), 8.29 (2H, d, Ar—H), 7.49 (1H, d, Ar—H), 7.83 (2H, d, Ar—H), 8.38 (1H, s, Ar—H), 10.68 (1H, s, —C(=O)—NH—), 10.59 (1H, s, —C(=O)—NH—), 5.89 (2H, s, —NH$_2$).

EXAMPLE 59

V-61 N-(2-amino-4-pyridyl)-4-[3-(4-aminophenyl)propionylaminomethyl]benzamide

Dissolving V-60 (0.419 g, 1 mmol) in methanol, adding stannous chloride dihydrate (0.678 g, 3 mmol), refluxing 2 hours, and then concentrating methanol. The residue is poured into ice-water, and a saturated solution of potassium carbonate is added to adjust pH to 9. Extracting with dichloromethane and drying over anhydrous magnesium sulfate overnight. After concentrating the solvent, the product is recrystallized with ethyl acetate, to obtain 0.259 g of a light yellow solid, with a yield of 66.6%.

MS(ES+):m/e 390.19.

$^1$H-NMR (400 MHz, DMSO-d$_6$) δppm: 2.51 (2H, t, —CH$_2$), 2.80 (2H, t, —CH$_2$), 4.28 (2H, s, —CH$_2$). 6.66 (1H, d, Ar—H), 7.24 (2H, d, Ar—H), 6.41 (2H, d, Ar—H), 6.87 (2H, d, Ar—H), 7.49 (1H, d, Ar—H), 7.83 (2H, d, Ar—H), 8.38 (1H, s, Ar—H), 10.32 (1H, s, —C(=O)—NH—), 10.43 (1H, s, —C(=O)—NH—), 5.89 (2H, s, —NH$_2$), 5.96 (2H, s, —NH$_2$).

EXAMPLE 60

V-62 N-(2-amino-3-pyridyl)-4-[3-(4-fluorophenyl)propionylaminomethyl]benzamide

P-fluorophenylpropionic acid (1.68 g, 10 mmol), thionylchloride (9.44 g, 40 mmol), p-aminobenzoic acid (1.52 g, 10 mmol), and 10 ml of 1 mol/L sodium hydroxide are used according to the method for the production of compound III in Method one to obtain 0.262 g of 4-[3-(4-fluorophenyl)propionylaminomethyl]benzoic acid (intermediate M-28) as a white solid, with a yield of 87.0%.

M-28 (0.301 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.187 g of a white solid, with a yield of 47.8%.

MS(ES+):m/e 393.16.

$^1$H-NMR (400 MHz, DMSO-d$_6$) δppm: 2.51 (2H, t, —CH$_2$), 2.80 (2H, t, —CH$_2$), 4.32 (2H, s, —CH$_2$), 6.64 (1H, dd, Ar—H), 6.92 (2H, d, Ar—H), 6.95 (1H, d, Ar—H), 7.10 (2H, d, Ar—H), 7.24 (2H, d, Ar—H), 7.75 (1H, d, Ar—H), 7.83 (2H, d, Ar—H), 10.34 (1H, s, —C(=O)—NH—), 10.43 (1H, s, —C(=O)—NH—), 5.77 (2H, s, —NH$_2$).

EXAMPLE 61

V-63 N-(2-amino-4-pyridyl)-4-[3-(4-fluorophenyl)propionylaminomethyl]benzamide

M-28 (0.301 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.184 g of a white solid, with a yield of 46.9%.

MS(ES+):m/e 393.16.

$^1$H-NMR (400 MHz, DMSO-d$_6$) δppm: 2.51 (2H, t, —CH$_2$), 2.80 (2H, t, —CH$_2$), 4.24 (2H, s, —CH$_2$), 6.66 (1H, d, Ar—H), 7.24 (2H, d, Ar—H), 6.92 (2H, d, Ar—H), 7.10 (2H, d, Ar—H), 7.49 (1H, d, Ar—H), 7.83 (2H, d, Ar—H), 8.38 (1H, s, Ar—H), 10.32 (1H, s, —C(=O)—NH—), 10.43 (1H, s, —C(=O)—NH—), 5.89 (2H, s, —NH$_2$).

EXAMPLE 62

V-64 N-(2-amino-3-pyridyl)-4-[3-(3-pyridyl)propionylaminomethyl]benzamide

Dissolving M-20 (5.64 g, 10 mmol) into 100 ml methanol, adding 10% of palladium on carbon 0.3 g, introducing hydrogen gas and stirring at room temperature 3 hours. After filtrating and concentrating to remove methanol, 5.45 g of 4-[(3-pyridine propionyl)aminomethyl]benzoic acid (intermediate M-29) as a white solid is obtained, with a yield of 95.9%.

M-29 (0.284 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.188 g of a white solid, with a yield of 50.1%.

MS(ES+):m/e 376.11.

$^1$H-NMR (400 MHz, DMSO-d$_6$) δppm: 2.51 (2H, t, —CH$_2$), 2.83 (2H, t, —CH$_2$), 4.30 (2H, s, —CH$_2$), 6.64 (1H, dd, Ar—H), 6.95 (1H, d, Ar—H), 7.24 (2H, d, Ar—H), 7.29 (1H, dd, Ar—H), 7.69 (1H, d, Ar—H), 7.75 (1H, d, Ar—H), 7.83 (2H, d, Ar—H), 8.35 (1H, d, Ar—H), 8.57 (1H, s, Ar—H), 9.56 (1H, s, —C(=O)—NH—), 9.43 (1H, s, —C(=O)—NH—), 5.73 (2H, s, —NH$_2$).

EXAMPLE 63

V-65 N-(2-amino-4-pyridyl)-4-[3-(3-pyridyl)propionylaminomethyl]benzamide

M-29 (0.284 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.196 g of a white solid, with a yield of 52.3%.

MS(ES+):m/e 376.18.

$^1$H-NMR (400 MHz, DMSO-d$_6$) δppm: 2.53 (2H, t, —CH$_2$), 2.82 (2H, t, —CH$_2$), 4.24 (2H, s, —CH$_2$), 6.68 (1H, d, Ar—H), 7.24 (2H, d, Ar—H), 7.29 (1H, dd, Ar—H), 7.69 (1H, d, Ar—H), 7.49 (1H, d, Ar—H), 7.83 (2H, d, Ar—H), 8.38 (1H, s, Ar—H), 8.35 (1H, d, Ar—H), 8.57 (1H, s, Ar—H), 10.66 (1H, s, —C(=O)—NH—), 10.45 (1H, s, —C(=O)—NH—), 5.97 (2H, s, —NH$_2$).

EXAMPLE 64

V-66 N-(2-amino-3-pyridyl)-4-[3-(4-phenyl)phenylpropionylaminomethyl]benzamide

Dissolving M-21 (7.14 g, 10 mmol) in 100 ml of methanol, adding 10% of palladium on carbon 0.3 g, introducing hydrogen gas and stirring at room temperature 3 hours. After filtrating and concentrating to remove methanol, 7.05 g of 4-[3-(4-phenyl)phenylpropionyl)aminomethyl]benzoic acid (intermediate M-30) as a white solid is obtained, with a yield of 98.2%.

M-30 (0.359 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.225 g of a white solid, with a yield of 50.1%.

MS(ES+):m/e 451.11.

$^1$H-NMR (400 MHz, DMSO-d$_6$) δppm: 2.51 (2H, t, —CH$_2$), 2.83 (2H, t, —CH$_2$), 4.32 (2H, s, —CH$_2$), 6.64 (1H, dd, Ar—H), 6.95 (1H, d, Ar—H), 7.24 (2H, d, Ar—H), 7.18 (2H, d, Ar—H), 7.40 (2H, d, Ar—H), 7.50 (5H, t, Ar—H), 7.75 (1H, d, Ar—H), 7.83 (2H, d, Ar—H), 10.32 (1H, s, —C(=O)—NH—), 10.43 (1H, s, —C(=O)—NH—), 5.89 (2H, s, —NH$_2$).

EXAMPLE 65

V-67 N-(2-amino-4-pyridyl)-4-[3-(4-phenyl)phenylpropionylaminomethyl]benzamide

M-30 (0.359 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.235 g of a white solid, with a yield of 52.3%.

MS(ES+):m/e 451.18.

$^1$H-NMR (400 MHz, DMSO-d$_6$) δppm: 2.51 (2H, t, —CH$_2$), 2.80 (2H, t, —CH$_2$), 4.24 (2H, s, —CH$_2$), 6.66 (1H, d, Ar—H), 7.24 (2H, d, Ar—H), 7.18 (2H, d, Ar—H), 7.40 (2H, d, Ar—H), 7.48 (5H, s, Ar—H), 7.49 (1H, d, Ar—H), 7.83 (2H, d, Ar—H), 8.38 (1H, s, Ar—H), 10.32 (1H, s, —C(=O)—NH—), 10.43 (1H, s, —C(=O)—NH—), 5.89 (2H, s, —NH$_2$).

EXAMPLE 66

V-68 N-(2-amino-3-pyridyl)-4-[3-(2-naphthyl)propionylaminomethyl]benzamide

Dissolving M-22 (6.62 g, 10 mmol) in 100 ml of methanol, adding 10% of palladium on carbon 0.3 g, introducing hydrogen gas and stirring at room temperature 3 hours. After filtrating and concentrating to remove methanol, 6.59 g of 4-[3-(4-phenyl)phenylpropionyl)aminomethyl]benzoic acid (intermediate M-31) as a white solid is obtained, with a yield of 99.3%.

M-31 (0.333 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.225 g of a white solid, with a yield of 53.1%.

MS(ES+):m/e 425.11.

$^1$H-NMR (400 MHz, DMSO-d$_6$) δppm: 2.51 (2H, t, —CH$_2$), 2.94 (2H, t, —CH$_2$) 4.24 (2H, s, —CH$_2$), 6.64 (1H, dd, Ar—H), 6.95 (1H, d, Ar—H), 7.24 (2H, d, Ar—H), 7.18 (1H, d, Ar—H), 7.46 (1H, s, Ar—H), 7.55 (1H, dd, Ar—H), 7.58 (1H, dd, Ar—H), 7.61 (1H, d, Ar—H), 7.64 (1H, d, Ar—H), 8.02 (1H, d, Ar—H), 7.75 (1H, d, Ar—H), 7.83 (2H, d, Ar—H), 10.32 (1H, s, —C(=O)—NH—), 10.43 (1H, s, —C(=O)—NH—), 5.89 (2H, s, —NH$_2$).

EXAMPLE 67

V-69 N-(2-amino-4-pyridyl)-4-[3-(2-naphthyl)propionylaminomethyl]benzamide

M-31 (0.333 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.221 g of a white solid, with a yield of 52.3%.

MS(ES+):m/e 451.18.

$^1$H-NMR (400 MHz, DMSO-d$_6$) δppm: 2.51 (2H, t, —CH$_2$), 2.93 (2H, t, —CH$_2$), 4.28 (2H, s, —CH$_2$), 6.66 (1H, d, Ar—H), 7.24 (2H, d, Ar—H), 7.18 (1H, d, Ar—H), 7.46 (1H, s, Ar—H), 7.55 (1H, dd, Ar—H), 7.58 (1H, dd, Ar—H), 7.61 (1H, d, Ar—H), 7.64 (1H, d, Ar—H), 8.02 (1H, d, Ar—H), 7.49 (1H, d, Ar—H), 7.83 (2H, d, Ar—H), 8.38 (1H, s, Ar—H), 10.32 (1H, s, —C(=O)—NH—), 10.43 (1H, s, —C(=O)—NH—), 5.89 (2H, s, —NH$_2$).

EXAMPLE 68

V-70 N-(2-amino-3-pyridyl)-4-[(3-benzylureido) methyl]benzamide

N,N-carbonyldiimidazole (1.62 g, 10 mmol), benzyl amine (1.07 g, 10 mmol), p-aminobenzoic acid (1.52 g, 10 mmol), and 10 ml of 1 mol/L sodium hydroxide solution are used according to the method for the production of compound III in Method two to obtain 2.65 g of 4-[(3-benzylureido)methyl] benzoic acid (intermediate M-32) as a white solid, with a yield of 93.0%.

M-32 (0.284 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.179 g of a white solid, with a yield of 47.8%.

MS(ES+):m/e 376.15.

$^1$H-NMR (400 MHz, DMSO-d$_6$) δppm: 4.26 (2H, s, —CH$_2$), 4.29 (2H, s, —CH$_2$), 6.64 (1H, dd, Ar—H), 6.98 (1H, d, Ar—H), 7.26 (2H, d, Ar—H), 7.30 (5H, s, Ar—H), 7.75 (1H, d, Ar—H), 7.83 (2H, d, Ar—H), 11.02 (1H, s, —C(=O)—NH—), 10.78 (1H, s, —C(=O)—NH—), 5.89 (2H, s, —NH$_2$).

EXAMPLE 69

V-71 N-(2-amino-4-pyridyl)-4-[(3-benzylureido) methyl]benzamide

M-32 (0.284 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.196 g of a white solid, with a yield of 52.1%.

MS(ES+):m/e 376.12.

$^1$H-NMR (400 MHz, DMSO-d$_6$) δppm: 4.20 (2H, s, —CH$_2$), 4.27 (2H, s, —CH$_2$), 6.66 (1H, d, Ar—H), 7.24 (2H, d, Ar—H), 7.30 (5H, s, Ar—H), 7.49 (1H, d, Ar—H), 7.83 (2H, d, Ar—H), 8.38 (1H, s, Ar—H), 10.32 (1H, s, —C(=O)—NH—), 10.43 (1H, s, —C(=O)—NH—), 5.89 (2H, s, —NH$_2$).

EXAMPLE 70

V-72 N-(2-amino-3-pyridyl)-4-[(4-methoxybenzylureido)methyl]benzamide

N,N-carbonyldiimidazole (1.62 g, 10 mmol), p-methyl benzyl amine (1.21 g, 10 mmol), p-aminobenzoic acid (1.52 g, 10 mmol), and 10 ml of 1 mol/L sodium hydroxide solution are used according to the method for the production of compound III in Method two to obtain 2.83 g of 4-[(4-methylbenzylureido)methyl]benzoic acid (intermediate M-33) as a white solid, with a yield of 95.0%.

M-33 (0.298 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.184 g of a white solid, with a yield of 47.3%.

MS(ES+):m/e 390.18.

$^1$H-NMR (400 MHz, DMSO-d$_6$) δppm: 2.24 (3H, s, —CH$_3$), 4.25 (2H, s, —CH$_2$), 4.27 (2H, s, —CH$_2$), 6.64 (1H, dd, Ar—H), 6.95 (1H, d, Ar—H), 7.24 (2H, d, Ar—H), 7.12 (2H, d, Ar—H), 7.19 (2H, d, Ar—H), 7.75 (1H, d, Ar—H), 7.83 (2H, d, Ar—H), 10.32 (1H, s, —C(=O)—NH—), 10.43 (1H, s, —C(=O)—NH—), 5.89 (2H, s, —NH$_2$).

EXAMPLE 71

V-73 N-(2-amino-4-pyridyl)-4-[(4-methylbenzylureido)methyl]benzamide

M-33 (0.298 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.168 g of a white solid, with a yield of 43.2%.

MS(ES+):m/e 390.17.

$^1$H-NMR (400 MHz, DMSO-d$_6$) δppm: 2.26 (3H, s, —CH$_3$), 4.24 (2H, s, —CH$_2$), 4.27 (2H, s, —CH$_2$), 6.66 (1H, d, Ar—H), 7.24 (2H, d, Ar—H), 7.12 (2H, d, Ar—H), 7.19 (2H, d, Ar—H), 7.49 (1H, d, Ar—H), 7.85 (2H, d, Ar—H), 8.38 (1H, s, Ar—H), 10.32 (1H, s, —C(=O)—NH—), 10.43 (1H, s, —C(=O)—NH—), 5.89 (2H, s, —NH$_2$).

EXAMPLE 72

V-74 N-(2-amino-3-pyridyl)-4-[(4-methoxybenzylureido)methyl]benzamide

N,N-carbonyldiimidazole (1.62 g, 10 mmol), p-methoxy benzyl (1.37 g, 10 mmol), p-aminobenzoic acid (1.52 g, 10 mmol), and 10 ml of 1 mol/L sodium hydroxide solution are used according to the method for the production of compound III in Method two to obtain 2.98 g of 4-[(4-methoxybenzylureido)methyl]benzoic acid (intermediate M-34) as a white solid, with a yield of 95.0%.

MS(ES+):m/e 315.12.

M-34 (0.314 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.192 g of a white solid, with a yield of 47.3%.

MS(ES+):m/e 406.18.

¹H-NMR (400 MHz, DMSO-$d_6$) δppm: 3.82 (3H, s, —OC$\underline{H}_3$), 4.24 (2H, s, —C$\underline{H}_2$), 4.27 (2H, s, —C$\underline{H}_2$), 6.64 (1H, dd, Ar—$\underline{H}$), 6.95 (1H, d, Ar—$\underline{H}$), 6.69 (2H, d, Ar—$\underline{H}$), 6.98 (2H, d, Ar—$\underline{H}$), 7.19 (2H, d, Ar—$\underline{H}$), 7.75 (1H, d, Ar—$\underline{H}$), 7.83 (2H, d, Ar—$\underline{H}$), 10.33 (1H, s, —C(=O)—N$\underline{H}$—), 10.96 (1H, s, —C(=O)—N$\underline{H}$—), 5.66 (2H, s, —N$\underline{H}_2$).

EXAMPLE 73

V-75 N-(2-amino-4-pyridyl)-4-[(4-methoxybenzylureido)methyl]benzamide

M-34 (0.314 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.175 g of a white solid, with a yield of 43.2%.

MS(ES+):m/e 406.17.

¹H-NMR (400 MHz, DMSO-$d_6$) δppm: 3.82 (3H, s, —OC$\underline{H}_3$), 4.24 (2H, s, —C$\underline{H}_2$), 4.27 (2H, s, —C$\underline{H}_2$), 6.66 (1H, d, Ar—$\underline{H}$), 7.24 (2H, d, Ar—$\underline{H}$), 6.69 (2H, d, Ar—$\underline{H}$), 6.98 (2H, d, Ar—$\underline{H}$), 7.49 (1H, d, Ar—$\underline{H}$), 7.83 (2H, d, Ar—$\underline{H}$), 8.38 (1H, s, Ar—$\underline{H}$), 10.32 (1H, s, —C(=O)—N$\underline{H}$—), 10.43 (1H, s, —C(=O)—N$\underline{H}$—), 5.89 (2H, s, —N$\underline{H}_2$).

EXAMPLE 74

V-76 N-(2-amino-3-pyridyl)-4-[(3,4,5-trimethoxybenzylureido)methyl]benzamide N,N-carbonyldiimidazole (1.62 g, 10 mmol), 3,4,5-trimethoxybenzyl amine (1.97 g, 10 mmol), p-aminobenzoic acid (1.52 g, 10 mmol), and 10 ml of 1 mol/L sodium hydroxide are used according to the method for the production of compound III in Method two to obtain 3.54 g of 4-[(3,4,5-trimethoxybenzylureido)methyl]benzoic acid (intermediate M-35) as a white solid, with a yield of 94.6%.

M-35 (0.374 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.201 g of a white solid, with a yield of 43.2%.

MS(ES+):m/e 466.21.

¹H-NMR (400 MHz, DMSO-$d_6$) δppm: 3.82 (3H, s, —OC$\underline{H}_3$), 3.85 (6H, s, —OCH$_3$), 4.42 (2H, s, —C$\underline{H}_2$), 4.44 (2H, s, —C$\underline{H}_2$), 6.64 (1H, dd, Ar—$\underline{H}$), 6.95 (1H, d, Ar—$\underline{H}$), 6.59 (2H, d, Ar—$\underline{H}$), 7.24 (2H, d, Ar—$\underline{H}$), 7.75 (1H, d, Ar—$\underline{H}$), 7.83 (2H, d, Ar—$\underline{H}$), 10.32 (1H, s, —C(=O)—N$\underline{H}$—), 10.43 (1H, s, —C(=O)—N$\underline{H}$—), 5.89 (2H, s, —N$\underline{H}_2$).

EXAMPLE 75

V-77 N-(2-amino-4-pyridyl)-4-[(3,4,5-trimethoxybenzylureido)methyl]benzamide M-35 (0.374 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.220 g of a white solid, with a yield of 47.2%.

MS(ES+):m/e 466.12.

¹H-NMR (400 MHz, DMSO-$d_6$) δppm: 3.82 (3H, s, —OC$\underline{H}_3$), 3.85 (6H, s, —OCH$_3$), 4.34 (2H, s, —C$\underline{H}_2$), 4.39 (2H, s, —C$\underline{H}_2$), 6.66 (1H, d, Ar—$\underline{H}$), 7.24 (2H, d, Ar—$\underline{H}$), 6.59 (2H, d, Ar—$\underline{H}$), 7.49 (1H, d, Ar—$\underline{H}$), 7.83 (2H, d, Ar—$\underline{H}$), 8.38 (1H, s, Ar—$\underline{H}$), 10.32 (1H, s, —C(=O)—N$\underline{H}$—), 10.43 (1H, s, —C(=O)—N$\underline{H}$—), 5.89 (2H, s, —N$\underline{H}_2$).

EXAMPLE 76

V-78 N-(2-amino-3-pyridyl)-4-[(4-nitrobenzylureido)methyl]benzamide

N,N-carbonyldiimidazole (1.62 g, 10 mmol), 4-nitrobenzyl amine (1.52 g, 10 mmol), p-aminobenzoic acid (1.52 g, 10 mmol), and 10 ml of 1 mol/L sodium hydroxide solution are used according to the method for the production of compound III in Method two to obtain 2.49 g of 4-[(4-nitrobenzylureido)methyl]benzoic acid (intermediate M-36) as a yellow solid, with a yield of 75.4%.

M-36 (0.329 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.198 g of a yellow solid, with a yield of 47.1%.

MS(ES+):m/e 421.12.

¹H-NMR (400 MHz, DMSO-$d_6$) δppm: 4.42 (2H, s, —C$\underline{H}_2$), 4.44 (2H, s, —C$\underline{H}_2$), 6.64 (1H, dd, Ar—$\underline{H}$), 6.95 (1H, d, Ar—$\underline{H}$), 7.32 (2H, d, Ar—$\underline{H}$), 8.17 (2H, d, Ar—$\underline{H}$), 7.24 (2H, d, Ar—$\underline{H}$), 7.75 (1H, d, Ar—$\underline{H}$), 7.83 (2H, d, Ar—$\underline{H}$), 10.32 (1H, s, —C(=O)—N$\underline{H}$—), 10.43 (1H, s, —C(=O)—N$\underline{H}$—), 5.89 (2H, s, —N$\underline{H}_2$).

EXAMPLE 77

V-79 N-(2-amino-3-pyridyl)-4-[(4-aminobenzylurea)methyl]benzamide

Dissolving V-78 (0.420 g, 1 mmol) in methanol, adding stannous chloride dihydrate (0.678 g, 3 mmol), refluxing 2 hours, and then concentrating methanol. The residue is poured into ice-water, and a saturated solution of potassium carbonate is added to adjust pH to 9. Extracting with dichloromethane and drying over anhydrous magnesium sulfate overnight. After concentrating the solvent, the product is recrystallized with ethyl acetate, to obtain 0.203 g of a light yellow solid, with a yield of 52.0%.

MS(ES+):m/e 391.18.

¹H-NMR (400 MHz, DMSO-$d_6$) δppm: 4.42 (2H, s, —C$\underline{H}_2$), 4.44 (2H, s, —C$\underline{H}_2$), 6.64 (1H, dd, Ar—$\underline{H}$), 6.95 (1H, d, Ar—$\underline{H}$), 6.34 (2H, d, Ar—$\underline{H}$), 6.81 (2H, d, Ar—$\underline{H}$), 7.24 (2H, d, Ar—$\underline{H}$), 7.75 (1H, d, Ar—$\underline{H}$), 7.83 (2H, d, Ar—$\underline{H}$), 10.46 (1H, s, —C(=O)—N$\underline{H}$—), 10.97 (1H, s, —C(=O)—N$\underline{H}$—), 5.86 (2H, s, —N$\underline{H}_2$), 5.99 (2H, s, —N$\underline{H}_2$).

EXAMPLE 78

V-80 N-(2-amino-4-pyridyl)-4-[(4-nitrobenzylureido)methyl]benzamide

M-36 (0.329 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the product of product V in Method two to obtain 0.211 g of a light yellow solid, with a yield of 50.2%.

MS(ES+):m/e 421.12.

¹H-NMR (400 MHz, DMSO-$d_6$) δppm: 4.34 (2H, s, —C$\underline{H}_2$), 4.39 (2H, s, —C$\underline{H}_2$), 6.66 (1H, d, Ar—$\underline{H}$), 7.24 (2H, d, Ar—$\underline{H}$), 7.32 (2H, d, Ar—$\underline{H}$), 8.17 (2H, d, Ar—$\underline{H}$), 7.49 (1H, d, Ar—$\underline{H}$), 7.83 (2H, d, Ar—$\underline{H}$), 8.38 (1H, s, Ar—$\underline{H}$), 10.32 (1H, s, —C(=O)—N$\underline{H}$—), 10.43 (1H, s, —C(=O)—N$\underline{H}$—), 5.89 (2H, s, —N$\underline{H}_2$).

EXAMPLE 79

V-81 N-(2-amino-4-pyridyl)-4-[(4-aminobenzylureido)methyl]benzamide

Dissolving V-80 (0.420 g, 1 mmol) in methanol, adding stannous chloride dihydrate (0.678 g, 3 mmol), refluxing 2 hours, and then concentrating methanol. The residue is poured into ice-water, and a saturated solution of potassium carbonate is added to adjust pH to 9. Extracting with dichloromethane and drying over anhydrous magnesium sulfate overnight. After concentrating the solvent, the product is recrystallized with ethyl acetate, to obtain 0.194 g of a light yellow solid, with a yield of 49.7%.

MS(ES+):m/e 391.12.

$^1$H-NMR (400 MHz, DMSO-$d_6$) δppm: 4.34 (2H, s, —C$\underline{H}_2$), 4.39 (2H, s, —C$\underline{H}_2$), 6.66 (1H, d, Ar—$\underline{H}$), 7.24 (2H, d, Ar—$\underline{H}$), 6.34 (2H, d, Ar—$\underline{H}$), 6.81 (2H, d, Ar—$\underline{H}$), 7.49 (1H, d, Ar—$\underline{H}$), 7.83 (2H, d, Ar—$\underline{H}$), 8.38 (1H, s, Ar—$\underline{H}$), 10.32 (1H, s, —C(=O)—N$\underline{H}$—), 10.43 (1H, s, —C(=O)—N$\underline{H}$—), 5.89 (2H, s, —N$\underline{H}_2$), 6.13 (2H, s, —N$\underline{H}_2$).

EXAMPLE 80

V-82 N-(2-amino-3-pyridyl)-4-[(4-fluorobenzylureido)methyl]benzamide

N,N-carbonyldiimidazole (1.62 g, 10 mmol), 4-fluorobenzylamine (1.25 g, 10 mmol), p-aminobenzoic acid (1.52 g, 10 mmol), 10 ml of 1 mol/L sodium hydroxide solution are used according to the method for the production of compound III in Method two to obtain 2.72 g of 4-[(4-fluorobenzylurea)methyl]benzoic acid (intermediate M-37) as a white solid, with a yield of 90.0%.

M-37 (0.302 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 2.27 g of a white solid, with a yield of 58.0%.

MS(ES+):m/e 393.15.

$^1$H-NMR (400 MHz, DMSO-$d_6$) δppm: 4.42 (2H, s, —C$\underline{H}_2$), 4.44 (2H, s, —C$\underline{H}_2$), 6.64 (1H, dd, Ar—$\underline{H}$), 6.95 (1H, d, Ar—$\underline{H}$), 7.04 (2H, d, Ar—$\underline{H}$), 7.10 (2H, d, Ar—$\underline{H}$), 7.24 (2H, d, Ar—$\underline{H}$), 7.75 (1H, d, Ar—$\underline{H}$), 7.83 (2H, d, Ar—$\underline{H}$), 10.32 (1H, s, —C(=O)—N$\underline{H}$—), 10.43 (1H, s, —C(=O)—N$\underline{H}$—), 5.89 (2H, s, —N$\underline{H}_2$).

EXAMPLE 81

V-83 N-(2-amino-4-pyridyl)-4-[(4-fluorobenzylureido)methyl]benzamide

M-37 (0.302 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 2.30 g of a white solid, with a yield of 58.6%.

MS(ES+):m/e 393.16.

$^1$H-NMR (400 MHz, DMSO-$d_6$) δppm: 4.34 (2H, s, —C$\underline{H}_2$), 4.39 (2H, s, —C$\underline{H}_2$), 6.66 (1H, d, Ar—$\underline{H}$), 7.24 (2H, d, Ar—$\underline{H}$), 7.04 (2H, d, Ar—$\underline{H}$), 7.10 (2H, d, Ar—$\underline{H}$), 7.49 (1H, d, Ar—$\underline{H}$), 7.83 (2H, d, Ar—$\underline{H}$), 8.38 (1H, s, Ar—$\underline{H}$), 10.32 (1H, s, —C(=O)—N$\underline{H}$—), 10.43 (1H, s, —C(=O)—N$\underline{H}$—), 5.89 (2H, s, —N$\underline{H}_2$).

EXAMPLE 82

V-84 N-(2-amino-3-pyridyl)-4-[(3-pyridylmethylureido)methyl]benzamide

N,N-carbonyldiimidazole (1.62 g, 10 mmol), 3-aminomethylpyridine (1.08 g, 10 mmol), p-aminobenzoic acid (1.52 g, 10 mmol), and 10 ml of 1 mol/L sodium hydroxide solution are used according to the method for the production of compound III in Method two to obtain 2.65 g of 4-[(3-pyridylmethylureido)methyl]benzoic acid (intermediate M-38) as a white solid, with a yield of 93.3%. MS(ES+):m/e 286.13.

M-38 (0.285 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.192 g of a white solid, with a yield of 51.0%.

MS(ES+):m/e 377.12.

$^1$H-NMR (400 MHz, DMSO-$d_6$) δppm: 4.42 (2H, s, —C$\underline{H}_2$), 4.49 (2H, s, —C$\underline{H}_2$), 6.67 (1H, dd, Ar—$\underline{H}$), 6.98 (1H, d, Ar—$\underline{H}$), 7.42 (1H, dd, Ar—$\underline{H}$), 7.88 (1H, d, Ar—$\underline{H}$), 7.24 (2H, d, Ar—$\underline{H}$), 7.75 (1H, d, Ar—$\underline{H}$), 7.83 (2H, d, Ar—$\underline{H}$), 8.39 (1H, d, Ar—$\underline{H}$), 8.77 (1H, s, Ar—$\underline{H}$), 9.97 (1H, s, —C(=O)—N$\underline{H}$—), 10.66 (1H, s, —C(=O)—N$\underline{H}$—), 5.89 (2H, s, —N$\underline{H}_2$).

EXAMPLE 83

V-85 N-(2-amino-4-pyridyl)-4-[(3-pyridylmethylureido)methyl]benzamide

M-38 (0.285 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.193 g of a white solid, with a yield of 51.3%.

MS(ES+):m/e 377.12.

$^1$H-NMR (400 MHz, DMSO-$d_6$) δppm: 4.34 (2H, s, —C$\underline{H}_2$), 4.39 (2H, s, —C$\underline{H}_2$), 6.66 (1H, d, Ar—$\underline{H}$), 7.24 (2H, d, Ar—$\underline{H}$), 7.42 (1H, dd, Ar—$\underline{H}$), 7.88 (1H, d, Ar—$\underline{H}$), 7.49 (1H, d, Ar—$\underline{H}$), 7.83 (2H, d, Ar—$\underline{H}$), 8.38 (1H, s, Ar—$\underline{H}$), 8.37 (1H, d, Ar—$\underline{H}$), 8.75 (1H, s, Ar—$\underline{H}$), 10.32 (1H, s, —C(=O)—N$\underline{H}$—), 10.43 (1H, s, —C(=O)—N$\underline{H}$—), 5.89 (2H, s, —N$\underline{H}_2$).

EXAMPLE 84

V-86 N-(2-amino-3-pyridyl)-4-[(3-biphenylmethylureido)methyl]benzamide

N,N-carbonyldiimidazole (1.62 g, 10 mmol), 4-aminomethylbiphenyl (1.83 g, 10 mmol), p-aminobenzoic acid (1.52 g, 10 mmol), and 10 ml of 1 mol/L sodium hydroxide solution are used according to the method for the production of compound III in Method two to obtain 3.36 g of 4-[(3-biphenylmethylurea)methyl]benzoic acid (intermediate M-39) as a white solid, with a yield of 93.3%.

M-39 (0.360 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.230 g of a white solid, with a yield of 51.0%.

MS(ES+):m/e 452.20.

$^1$H-NMR (400 MHz, DMSO-$d_6$) δppm: 4.39 (2H, s, —C$\underline{H}_2$), 4.44 (2H, s, —C$\underline{H}_2$), 6.64 (1H, dd, Ar—$\underline{H}$), 6.95 (1H, d, Ar—$\underline{H}$), 7.12 (2H, d, Ar—$\underline{H}$), 7.33 (2H, d, Ar—$\underline{H}$), 7.48 (5H, s, Ar—$\underline{H}$), 7.24 (2H, d, Ar—$\underline{H}$), 7.75 (1H, d, Ar—$\underline{H}$), 7.83

(2H, d, Ar—H), 10.32 (1H, s, —C(=O)—NH—), 10.40 (1H, s, —C(=O)—NH—), 5.96 (2H, s, —NH₂).

EXAMPLE 85

V-87 N-(2-amino-4-pyridyl)-4-[(3-biphenylmethylureido)methyl]benzamide

M-39 (0.360 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.186 g of a white solid, with a yield of 41.3%.

MS(ES+):m/e 452.12.

¹H-NMR (400 MHz, DMSO-d₆) δppm: 4.34 (2H, s, —CH₂), 4.39 (2H, s, —CH₂), 6.66 (1H, d, Ar—H), 7.24 (2H, d, Ar—H), 7.12 (2H, d, Ar—H), 7.33 (2H, d, Ar—H), 7.48 (5H, s, Ar—H), 7.49 (1H, d, Ar—H). 7.83 (2H, d, Ar—H), 8.40 (1H, s, Ar—H), 10.32 (1H, s, —C(=O)—NH—), 10.43 (1H, s, —C(=O)—NH—), 5.89 (2H, s, —NH₂).

EXAMPLE 86

V-88 N-(2-amino-3-pyridyl)-4-[3-(2-naphthylmethyl)ureidomethyl]benzamide

N,N-carbonyldiimidazole (1.62 g, 10 mmol), 2-aminomethylnaphthalene (1.57 g, 10 mmol), p-aminobenzoic acid (1.52 g, 10 mmol), and 10 ml of 1 mol/L sodium hydroxide solution are used according to the method for the production of compound III in Method two to obtain 3.12 g of 4-[3-(2-naphthylmethyl)ureidomethyl]benzoic acid (intermediate M-40) as a white solid, with a yield of 93.3%.

M-40 (0.334 g, 1 mmol), 2,3-diaminopyridine (0.109 g, 1 mmol), HBTU (0.379 g, 1 mmol), N,N-dimethylformamide (10 ml), and triethylamine 0 (0.202 g, 2 mmol) are used according to the method for the production of product V in Method two to obtain 0.217 g of a white solid, with a yield of 51.0%.

MS(ES+):m/e 426.12.

¹H-NMR (400 MHz, DMSO-d₆) δppm: 4.44 (2H, s, —CH₂), 4.47 (2H, s, —CH₂), 6.64 (1H, dd, Ar—H), 6.96 (1H, d, Ar—H), 7.20 (1H, d, Ar—H), 7.61 (1H, d, Ar—H), 7.46 (1H, s, Ar—H), 7.55 (1H, dd, Ar—H), 7.58 (1H, dd, Ar—H), 7.64 (1H, d, Ar—H), 8.02 (1H, d, Ar—H), 7.24 (2H, d, Ar—H), 7.75 (1H, d, Ar—H), 7.83 (2H, d, Ar—H), 10.32 (1H, s, —C(=O)—NH—), 10.43 (1H, s, —C(=O)—NH—), 5.89 (2H, s, —NH₂).

EXAMPLE 87

V-89 N-(2-amino-4-pyridyl)-4-[3-(2-naphthylmethyl)ureidomethyl]benzamide

M-40 (0.334 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.218 g of a white solid, with a yield of 51.3%.

MS(ES+):m/e 426.12.

¹H-NMR (400 MHz, DMSO-d₆) δppm: 4.34 (2H, s, —CH₂), 4.39 (2H, s, —CH₂), 6.66 (1H, d, Ar—H), 7.24 (2H, d, Ar—H), 7.18 (1H, d, Ar—H), 7.61 (1H, d, Ar—H), 7.46 (1H, s, Ar—H), 7.55 (1H, dd, Ar—H), 7.58 (1H, dd, Ar—H), 7.64 (1H, d, Ar—H), 8.02 (1H, d, Ar—H), 7.49 (1H, d, Ar—H), 7.83 (2H, d, Ar—H), 8.38 (1H, s, Ar—H), 10.32 (1H, s, —C(=O)—NH—), 10.43 (1H, s, —C(=O)—NH—), 5.89 (2H, s, —NH₂).

EXAMPLE 88

V-90 N-(2-amino-4-pyridyl)-4-[(3,4,5-trimethoxycinnamoyl)-1-aminoethyl]benzamide M-90 (0.375 g, 1 mmol), 2-(1-aminoethyl)aniline (0.136 g, 1 mmol), HBTU (0.379 g, 1 mmol), N,N-dimethylformamide (10 ml), and triethylamine (0.202 g, 2 mmol) are used according to the method for the production of product V in Method two to obtain 0.222 g of a white solid, with a yield of 47.6%.

MS(ES+):m/e 481.19.

¹H-NMR (400 MHz, DMSO-d₆) δppm: 1.58 (3H, d, —CHCH₃), 3.91 (3H, s, —OCH₃), 3.92 (6H, s, —OCH₃), 5.05 (2H, q, —CH₂), 5.34 (2H, s, —CH₂), 6.15 (2H, d, Ar—H), 6.66 (1H, d, Ar—H), 7.30 (2H, d, Ar—H), 7.49 (1H, d, Ar—H), 7.90 (2H, d, Ar—H), 8.38 (1H, s, Ar—H), 10.32 (1H, s, —C(=O)—NH—), 10.43 (1H, s, —C(=O)—NH—), 5.89 (2H, s, —NH₂).

EXAMPLE 89

V-91 N-(2-amino-4-pyridyl)-4-[(phenylpiperazinylacyl)aminomethyl]benzamide 4-phenylpiperazine-1-carboxylic acid (2.06 g, 10 mmol), thionylchloride (4.72 g, 40 mmol), dichloromethane (10 ml), p-aminobenzoic acid (1.52 g, 10 mmol), and 10 ml of 1 mol/L sodium hydroxide are used according to the method for the production of compound III in Method two to obtain 3.09 g of 4-[(phenylpiperazinylacyl)aminomethyl]benzoic acid (intermediate M-41) as a white solid, with a yield of 91.2%.

M-41 (0.371 g, 1 mmol), 3,4-diaminopyridine (0.109 g, 1 mmol), HBTU (0.379 g, 1 mmol), N,N-dimethylformamide (10 ml), and triethylamine (0.404 g, 4 mmol) are used according to the method for the production of product V in Method one to obtain 0.270 g of a white solid, with a yield of 63.4%.

MS(ES+):m/e 431.17

¹H-NMR (400 MHz, DMSO-d₆) δppm: 3.35 (2H, d, —NCH₂CH₂), 3.39 (2H, d, —NCH₂CH₂), 4.22 (2H, s, —CH₂), 6.66 (1H, d, Ar—H), 6.94 (2H, d, Ar—H), 6.96 (1H, dd, Ar—H), 7.21 (2H, d, Ar—H), 7.24 (2H, d, Ar—H), 7.83 (2H, d, Ar—H), 7.46 (1H, d, Ar—H), 8.38 (1H, s, Ar—H), 10.42 (1H, s, —C(=O)—NH—), 10.49 (1H, s, —C(=O)—NH—), 5.89 (2H, s, —NH₂).

EXAMPLE 90

V-91 N-(2-amino-4-pyridyl)-4-[(3,4,5-trimethoxycinnamoyl)-2-phenylethylamino]benzamide 3,4,5-trimethoxycinnamic acid (2.38 g, 10 mmol), thionylchloride (4.72 g, 40 mmol), dichloromethane (10 ml), 4-(1-amino-2-phenylethyl)benzoic acid (2.41 g, 10 mmol), and 10 ml of 1 mol/L sodium hydroxide are used according to the method for the production of compound III in Method one to obtain 4.20 g of 4-[(3,4,5-trimethoxycinnamoyl)aminomethyl]benzoic acid (intermediate M-42) as a white solid, with a yield of 91.2%.

M-42 (0.371 g, 1 mmol), 3,4-diaminopyridine (0.109 g, 1 mmol), HBTU (0.379 g, 1 mmol), N,N-dimethylformamide (10 ml), and triethylamine (0.404 g, 4 mmol) are used according to the method for the production of product V in Method one to obtain 0.347 g of a white solid, with a yield of 63.4%.

MS(ES+):m/e 553.17

¹H-NMR (400 MHz, DMSO-d₆) δppm: 2.99 (1H, dd, —CHCH₂), 3.22 (1H, dd, —CHCH₂), 3.71 (3H, s, —OCH₃), 3.83 (6H, s, —OCH₃), 5.26 (1H, t, —CH), 7.26 (5H, s, Ar—H), 6.66 (1H, d, Ar—H), 6.84 (1H, d, —CH=CH—), 6.78 (2H, s, Ar—H), 7.30 (2H, d, Ar—H), 7.55 (1H, d, —CH=CH—), 7.90 (2H, d, Ar—H), 7.46 (1H, d, Ar—H), 8.38 (1H, s, Ar—H), 10.32 (1H, s, —C(=O)—NH—), 10.43 (1H, s, —C(=O)—NH—), 5.96 (2H, s, —NH₂).

EXAMPLE 91

V-31 N-(2-amino-3-pyridyl)-4-[(3-methoxycinnamoyl)aminomethyl]benzamide 3-methoxycinnamic acid (1.78 g, 10 mmol), thionylchloride (4.72 g, 40 mmol), dichloromethane (10 ml), p-aminobenzoic acid (1.52 g, 10 mmol), and 10 ml of 1 mol/L sodium hydroxide are used according to the method for the production of intermediate III in Method one to obtain 2.80 g of 4-[(3-methoxycinnamoyl)aminomethyl]benzoic acid (intermediate M-43) as a white solid, with a yield of 90.0%.

M-43 (0.311 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.197 g of a white solid, with a yield of 48.9%.

MS(ES+):m/e403.18.

¹H-NMR (400 MHz, DMSO-d₆) δppm: 3.73 (3H, s, —OCH₃), 4.22 (2H, s, —CH₂), 6.64 (1H, d, Ar—H), 6.66 (1H, d, Ar—H), 6.84 (1H, d, —CH=CH—), 6.86 (1H, d, Ar—H), 7.10 (1H, dd, Ar—H), 7.16 (1H, s, Ar—H), 7.24 (2H, d, Ar—H), 7.55 (1H, d, —CH=CH—), 7.83 (2H, d, Ar—H), 8.08 (1H, d, Ar—H), 8.38 (1H, s, Ar—H), 10.30 (1H, s, —C(=O)—NH—), 10.35 (1H, s, —C(=O)—NH—), 5.87 (2H, s, —NH₂).

EXAMPLE 92

V-32 N-(2-amino-4-pyridyl)-4-[(3-methoxycinnamoyl)aminomethyl]benzamide

M-43 (0.311 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.192 g of a white solid, with a yield of 47.7%.

MS(ES+):m/e 403.17.

¹H-NMR (400 MHz, DMSO-d₆) δppm: 3.85 (3H, s, —OCH₃), 4.32 (2H, s, —CH₂), 6.66 (1H, d, Ar—H), 6.90 (1H, d, —CH=CH—), 6.95 (1H, d, Ar—H), 7.09 (2H, d, Ar—H), 7.27 (2H, d, Ar—H), 7.57 (1H, d, —CH=CH—), 7.68 (2H, d, Ar—H), 7.83 (2H, d, Ar—H), 8.38 (1H, d, Ar—H), 10.30 (1H, s, —C(=O)—NH—), 10.43 (1H, s, —C(=O)—NH—), 5.87 (2H, s, —NH₂).

EXAMPLE 93

V-31 N-(2-amino-3-pyridyl)-4-[(3,4-dimethoxycinnamoyl)aminomethyl]benzamide 3,4-dimethoxycinnamic acid (2.08 g, 10 mmol), thionylchloride (4.72 g, 40 mmol), dichloromethane (10 ml), p-aminobenzoic acid (1.52 g, 10 mmol), and 10 ml of 1 mol/L sodium hydroxide are used according to the method for the production of intermediate III in Method one to obtain 3.07 g of 4-[(3,4-dimethoxycinnamoyl)aminomethyl]benzoic acid (intermediate M-44) as a white solid, with a yield of 90.0%.

M-44 (0.341 g, 1 mmol), 2,3-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.211 g of a white solid, with a yield of 48.9%.

MS(ES+):m/e433.18.

¹H-NMR (400 MHz, DMSO-d₆) δppm: 3.83 (3H, s, —OCH₃), 3.85 (3H, s, —OCH₃), 4.22 (2H, s, —CH₂), 6.64 (1H, dd, Ar—H), 6.84 (1H, d, —CH=CH—), 6.93 (1H, d, Ar—H), 6.95 (1H, d, Ar—H), 7.09 (1H, d, Ar—H), 7.24 (2H, d, Ar—H), 7.32 (1H, d, —CH=CH—), 7.75 (1H, d, Ar—H), 7.83 (2H, d, Ar—H), 10.30 (1H, s, —C(=O)—NH—), 10.35 (1H, s, —C(=O)—NH—), 6.11 (2H, s, —NH₂).

EXAMPLE 94

V-32 N-(2-amino-4-pyridyl)-4-[(3,4-dimethoxycinnamoyl)aminomethyl]benzamide

M-44 (0.341 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method one to obtain 0.206 g of a white solid, with a yield of 47.7%.

MS(ES+):m/e 433.17.

¹H-NMR (400 MHz, DMSO-d₆) δppm: 3.83 (3H, s, —OCH₃), 3.85 (3H, s, —OCH₃), 4.22 (2H, s, —CH₂), 6.66 (1H, d, Ar—H), 6.90 (1H, d, —CH=CH—), 6.95 (1H, d, Ar—H), 7.06 (1H, d, Ar—H), 7.22 (1H, d, Ar—H), 7.34 (2H, d, Ar—H), 7.57 (1H, d, —CH=CH—), 7.83 (2H, d, Ar—H), 8.08 (1H, d, Ar—H), 8.38 (1H, s, Ar—H), 10.30 (1H, s, —C(=O)—NH—), 10.43 (1H, s, —C(=O)—NH—), 5.85 (2H, s, —NH₂).

EXAMPLE 95

V-13 N-(2-amino-4-pyridyl)-4-[(3-methoxybenzyloxyacyl)aminomethyl]benzamide

N,N-carbonyldiimidazole (1.62 g, 10 mmol), 3-methoxybenzenemethanol (1.38 g, 10 mmol), p-aminobenzoic acid (1.52 g, 10 mmol), and 10 ml of 1 mol/L sodium hydroxide solution are used accoridng to the method for the production of compound III in Method two to obtain 2.96 g of 4-[(3-methoxybenzyloxyacyl)aminomethyl]benzoic acid (intermediate M-45) as a white solid, with a yield of 94.0%.

M-45 (0.315 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.179 g of a white solid, with a yield of 44.3%.

MS(ES+):m/e 407.16.

¹H-NMR (400 MHz, DMSO-d₆) δppm: 3.73 (3H, s, —OCH₃), 4.22 (2H, s, —CH₂), 5.35 (2H, s, —CH₂). 6.64 (1H, s, Ar—H), 6.66 (1H, d, Ar—H), 6.70 (1H, d, Ar—H), 6.75 (1H, d, Ar—H), 7.08 (1H, dd, Ar—H), 7.24 (2H, d, Ar—H), 7.75 (1H, d, Ar—H), 7.83 (2H, d, Ar—H), 8.08 (1H, d, Ar—H), 8.08 (1H, s, Ar—H), 10.11 (1H, s, —C(=O)—NH—), 9.96 (1H, s, —C(=O)—NH—), 5.78 (2H, s, —NH₂).

EXAMPLE 96

V-14 N-(2-amino-4-pyridyl)-4-[(3,4-dimethoxybenzyloxyacyl)aminomethyl]benzamide N,N-carbonyldiimidazole (1.62 g, 10 mmol), 3,4-dimethoxybenzenemethanol (1.68 g, 10 mmol), p-aminobenzoic acid (1.52 g, 10 mmol), and 10 ml of 1 mol/L sodium hydroxide solution are used according to the method for the production of compound III in Method two to obtain 3.24 g of a white solid 4-[(3-methoxybenzyloxyacyl)aminomethyl] benzoic acid (intermediate M-46), with a yield of 94.0%.

V-46 (0.345 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol) are used according to the method for the production of product V in Method two to obtain 0.174 g of a white solid, with a yield of 40.0%.

MS(ES+):m/e 437.13.

$^1$H-NMR (400 MHz, DMSO-d$_6$) δppm: 3.75 (3H, s, —OCH$_3$), 3.83 (3H, s, —OCH$_3$), 4.22 (2H, s, —CH$_2$), 5.30 (2H, s, —CH$_2$), 6.59 (1H, s, Ar—H), 6.66 (1H, d, Ar—H), 6.70 (1H, d, Ar—H), 6.91 (1H, d, Ar—H), 7.24 (2H, d, Ar—H), 7.83 (2H, d, Ar—H), 7.08 (1H, d, Ar—H), 8.38 (1H, s, Ar—H), 10.13 (1H, s, —C(=O)—NH—), 9.97 (1H, s, —C(=O)—NH—), 5.85 (2H, s, —NH$_2$).

EXAMPLE 97

An Assay for Determining the In Vitro Inhibition Activity of the Compound on Histone Deacetylase A 96-well plate (black) for determining luciferase is made by Costar Company of U.S. The histone deacetylase is obtained by homogenization of liver of rats. The histone deacetylase reacts with small molecular fluorescent substrate MAL such that the substrate MAL is deacetylated to become ML. The residual substrate MAL that does not participate the reaction is obtained by extracting, and its fluorescent value is determined to calculate the activity of enzyme and the inhibiton activity of the compound to the enzyme.

The compound to be detected is dissolved with 200 μL of DMSO. The stock solution of the compound to be detected is diluted with PBS to a concentration of the working solution. The histone deacetylase, the MAL fluorescent substrate and the compound to be detected are mixed in a water bath at 37° C. and reacted 16 hours. The final concentration of the compound to be detected is: MS275 and its similar compound: 10, 100 μmol/.

The reaction solution is extracted with ethyl acetate. The extract is pumped in vacuum and thereto added 110 μL of methanol (40%). Taking 50 μL/well to a 96-well plate and making a fluorescent detection at 325/390 nm.

The negative control wherein histone deacetylase is not added to the reaction is 100% inhibition. The control that only contains histone deacetylase without any inhibitor is the background (0% inhibition).

The inhibition rate of the sample to be detected=(the detected fluorescent value−the background)/(the fluorescent value of the negative control−background)×100%

The inhibition rate and the standard deviation in the results are the average inhibition percentage and the standard deviation of each parallel well in each dosage group.

TABLE 2

The in vitro inhibition activity of the compound on histone deacetylase

| compound | inhibition rate % average number ± SD dosage(10 μmol/L) n = 4 | | inhibition rate % average number ± SD dosage(100 μmol/L) n = 4 | |
|---|---|---|---|---|
| MS275 | 45.588 | 1.343 | 66.300 | 2.905 |
| V-1 | 0.479 | 0.763 | 0.293 | 0.433 |
| V-2 | −0.124 | 0.688 | 0.080 | 0.306 |
| V-3 | 0.170 | 0.912 | 0.481 | 0.238 |
| V-4 | 1.644 | 0.544 | 12.033 | 1.851 |
| V-5 | 9.422 | 0.172 | 37.240 | 1.099 |
| V-24 | 46.547 | 0.537 | 70.300 | 1.010 |
| V-34 | 0.148 | 0.202 | 3.772 | 0.619 |
| V-35 | 2.554 | 0.964 | 1.983 | 0.676 |
| V-36 | 3.894 | 1.292 | 20.670 | 6.069 |
| V-37 | 32.472 | 0.665 | 69.945 | 1.667 |
| V-47 | 46.423 | 0.166 | 72.140 | 2.019 |

EXAMPLE 98

An assay for determining the in vitro inhibition activity of the compound on histone deacetylase is conducted according to the specification of HDAC inhibitor screeing kid (Biovision Company/Catalog #K340-100). The compound to be detected is formulated to a solution of 2 mM, 200 uM, and 40 uM, and the inhibition rate of the compound on enzyme is detected under their respective concentrations.

The following are the results:

TABLE 3

The in vitro inhibition activity of the compound on histone deacetylase as detected by the kit

| | Compound | 2 mM | | 62.5 μM | | 3.91 μM | |
|---|---|---|---|---|---|---|---|
| | | Inhibition rate (%) | SD | Inhibition rate(%) | SD | Inhibition rate(%) | SD |
| | MS-275 | 82.2 | 0.2 | 60.5 | 0.3 | 32.5 | 0.7 |
| 1 | V-4 | 65.2 | 1.1 | 19.8 | 2.4 | 9.4 | 4.5 |
| 2 | V-5 | 77.1 | 0.5 | 28.0 | 2.3 | 7.6 | 1.6 |
| 3 | V-7 | 78.2 | 0.4 | 36.0 | 1.2 | 9.5 | 2.9 |
| 4 | V-8 | 35.3 | 4.3 | 10.3 | 1.5 | 6.3 | 4.9 |
| 5 | V-9 | 36.7 | 2.1 | 16.8 | 2.2 | 2.8 | 0.2 |
| 6 | V-10 | 47.1 | 0.2 | 38.0 | 0.9 | 14.5 | 0.8 |
| 7 | V-11 | 39.2 | 1.0 | 22.1 | 1.8 | 6.5 | 1.0 |
| 8 | V-12 | 46.2 | 0.2 | 41.1 | 0.2 | 8.9 | 5.4 |
| 9 | V-13 | 50.0 | 2.2 | 7.8 | 2.8 | 1.9 | 2.5 |
| 10 | V-14 | 77.2 | 0.1 | 32.9 | 0.7 | 12.0 | 1.7 |
| 11 | V-15 | −12.5 | 13.0 | 11.1 | 1.1 | 4.1 | 0.2 |
| 12 | V-17 | 85.2 | 1.7 | 43.0 | 3.8 | 16.8 | 0.4 |
| 13 | V-19 | 50.0 | 4.0 | 20.1 | 0.2 | 1.0 | 1.9 |
| 14 | V-20 | 64.8 | 4.4 | 47.1 | 0.3 | 16.8 | 0.6 |
| 15 | V-25 | 61.4 | 1.7 | 51.5 | 0.4 | 13.7 | 2.1 |
| 16 | V-26 | 58.6 | 1.6 | 56.8 | 0.6 | 24.8 | 0.1 |
| 17 | V-27 | 66.7 | 0.3 | 59.7 | 0.6 | 19.7 | 1.4 |
| 18 | V-28 | 66.0 | 1.9 | 56.8 | 1.1 | 30.4 | 0.3 |
| 19 | V-29 | 72.3 | 0.7 | 57.8 | 0.3 | 22.7 | 3.8 |
| 20 | V-30 | 67.5 | 1.5 | 56.9 | 1.4 | 28.2 | 0.8 |
| 21 | V-34 | 79.2 | 1.3 | 39.1 | 1.6 | 10.1 | 0.3 |
| 22 | V-35 | 84.2 | 1.3 | 47.5 | 0.3 | 19.9 | 0.8 |
| 23 | V-36 | 40.7 | 1.3 | 37.3 | 3.1 | 17.5 | 0.2 |
| 24 | V-38 | 76.1 | 0.4 | 55.2 | 0.7 | 24.2 | 0.6 |
| 25 | V-40 | 72.8 | 1.1 | 55.2 | 0.4 | 20.5 | 0.8 |
| 26 | V-42 | 82.4 | 2.0 | 40.2 | 2.6 | 11.4 | 1.1 |
| 27 | V-48 | 61.9 | 1.0 | 32.6 | 1.1 | 13.2 | 0.2 |
| 28 | V-50 | 37.8 | 1.4 | 31.0 | 1.3 | 8.6 | 1.3 |
| 29 | V-52 | 69.8 | 3.4 | 17.3 | 2.9 | 3.5 | 0.8 |
| 30 | V-54 | 42.5 | 0.4 | 3.1 | 2.4 | 2.2 | 0.5 |
| 31 | V-60 | 38.8 | 7.1 | 16.8 | 1.7 | 3.2 | 1.3 |
| 32 | V-91 | 81.8 | 0.1 | 47.8 | 0.7 | 10.1 | 1.2 |
| 33 | V-92 | 65.7 | 2.2 | 56.1 | 0.1 | 24.0 | 2.5 |
| 34 | V-93 | 55.3 | 5.7 | 48.0 | 0.1 | 14.3 | 1.1 |
| 35 | V-95 | 90.6 | 0.9 | 46.7 | 0.6 | 17.2 | 0.0 |
| 36 | V-96 | 85.0 | 1.2 | 42.2 | 2.8 | 14.0 | 2.2 |

EXAMPLE 99

An Assay for Detecting the In Vitro Inhibition Activity of Compound to Tumor Cells The cytotoxicity of samples to tumor cell strains is determined through MTT.

The result is shown in Table 4:

TABLE 4

The in vitro proliferation inhibition activity of the compound on various cell strains

| No. of the sample | Cell activity (IC50, µg/ml) | | |
|---|---|---|---|
| | K562 | A549 | Hut 78 |
| MS-275 | 3.20 | 24.42 | 0.15 |
| V-1 | >100 | >100 | 12.50 |
| V-2 | >100 | >100 | 76.21 |
| V-3 | >100 | >100 | 38.76 |
| V-4 | >100 | >100 | 4.21 |
| V-5 | >100 | >100 | 0.40 |
| V-24 | 6.23 | 7.11 | 0.30 |
| V-34 | >100 | >100 | 68.55 |
| V-35 | >100 | >100 | 60.94 |
| V-36 | >100 | >100 | 17.07 |
| V-37 | >100 | >100 | 1.86 |
| V-47 | 1.15 | 12.24 | 0.11 |

Note:
K562: human chronic myeloid leukemia cell strain, A549 (human lung adenocarcinoma cells), Hut 78 (T-cell Leukemia cell).

EXAMPLE 100

An Assay for Detecting the In Vitro Inhibition Activity of the Compound on Tumor Cells Detecting the inhibition rate of the compound concentrations of 100 µM and 10 µM to Hut78 T-cell Leukemia cell, Jurkat E6-1 human T-cell lymphoma, PANC-1 human pancreatic cancer cells, A549 human lung cancer cells, K562 human chronic myeloid leukemia cells, Hep3B2.1-7 human liver cancer cells, MDA-MB-435s human breast cancer cells, Colo320 human rectal cancer cells and PC-3 human prostate cancer using CCK-8 method. The following is the specific results:

TABLE 5

The in vitro proliferation inhibition activity of the compound on Hut-78, PANC-1 cell strains

| No. | Name | Hut-78 (inhibition %) | | | | PANC-1 (inhibition %) | | | |
|---|---|---|---|---|---|---|---|---|---|
| | | 100 µM | SD 100 µM | 10 µM | SD 10 µM | 100 µM | SD 100 µM | 10 µM | SD 10 µM |
| Positive drug | MS-275 | 85.3 | 6.5 | 61.8 | 6.7 | 31.6 | 4.0 | 12.4 | 7.3 |
| 1 | V-4 | 67.2 | 14.6 | 36.0 | 1.9 | 65.4 | 3.8 | 40.2 | 3.1 |
| 2 | V-5 | 72.8 | 2.3 | 43.4 | 4.1 | 74.1 | 2.7 | 20.7 | 9.8 |
| 3 | V-7 | 72.9 | 1.9 | 18.2 | 8.0 | 5.5 | 11.3 | 5.7 | 9.5 |
| 4 | V-8 | 15.8 | 3.0 | 6.4 | 9.6 | 11.9 | 1.7 | 14.4 | 6.8 |
| 5 | V-9 | 43.9 | 2.5 | 15.0 | 6.4 | 45.9 | 2.5 | 10.5 | 14.3 |
| 6 | V-10 | 66.6 | 1.4 | 15.5 | 3.9 | 19.7 | 12.6 | 16.9 | 7.5 |
| 7 | V-11 | 60.3 | 4.8 | 10.7 | 4.8 | 35.2 | 0.0 | 1.1 | 8.4 |
| 8 | V-12 | 83.6 | 1.7 | 17.5 | 6.2 | 34.9 | 6.1 | -1.8 | 3.5 |
| 9 | V-13 | 24.0 | 1.9 | 10.8 | 1.4 | 26.4 | 1.2 | 22.3 | 6.9 |
| 10 | V-14 | 47.5 | 2.1 | 8.1 | 4.0 | 19.0 | 1.5 | 13.0 | 4.7 |
| 11 | V-15 | 24.6 | 3.8 | 28.5 | 1.6 | 21.1 | 6.1 | 24.0 | 3.6 |
| 12 | V-17 | 62.5 | 1.7 | 12.5 | 9.5 | 21.9 | 7.5 | 15.8 | 5.1 |
| 13 | V-19 | 54.0 | 7.6 | 19.8 | 2.0 | 36.8 | 9.1 | 26.0 | 9.2 |
| 14 | V-20 | 91.1 | 2.4 | 22.0 | 5.8 | 15.7 | 5.3 | -2.8 | 9.3 |
| 15 | V-23 | 10.4 | 0.9 | 20.7 | 2.7 | 0.5 | 3.9 | 7.2 | 5.9 |
| 16 | V-24 | 20.7 | 2.1 | 26.2 | 1.2 | 7.8 | 0.8 | 8.0 | 0.5 |
| 17 | V-25 | 53.5 | 4.1 | 23.4 | 1.7 | 25.1 | 10.3 | 12.0 | 8.0 |
| 18 | V-26 | 82.3 | 2.4 | 39.9 | 4.3 | 23.9 | 3.7 | 0.9 | 1.5 |
| 19 | V-27 | 77.0 | 2.7 | 43.0 | 7.0 | 26.2 | 9.0 | 20.2 | 10.9 |
| 20 | V-28 | 85.7 | 4.5 | 44.4 | 3.5 | 52.0 | 1.9 | -1.7 | 5.0 |
| 21 | V-29 | 75.6 | 1.0 | 45.2 | 4.7 | 33.3 | 1.9 | 12.5 | 2.1 |
| 22 | V-30 | 71.8 | 3.9 | 42.3 | 3.9 | 39.4 | 4.2 | 12.3 | 5.8 |
| 23 | V-34 | 53.1 | 2.3 | 9.9 | 3.8 | 4.0 | 2.8 | 9.2 | 4.2 |
| 24 | V-35 | 72.9 | 5.8 | 15.5 | 1.8 | 22.1 | 9.1 | 17.5 | 3.6 |
| 25 | V-36 | 60.0 | 2.1 | 8.1 | 1.8 | 39.5 | 0.5 | 20.8 | 1.4 |
| 26 | V-38 | 86.9 | 1.2 | 39.6 | 2.4 | 40.8 | 6.8 | 5.1 | 9.5 |
| 27 | V-40 | 69.3 | 3.1 | 29.2 | 0.8 | 9.5 | 5.9 | 4.4 | 1.2 |
| 28 | V-41 | 74.0 | 0.3 | 19.4 | 0.8 | 18.4 | 5.3 | 0.9 | 8.9 |
| 29 | V-42 | 55.8 | 4.7 | 28.2 | 2.9 | 50.6 | 0.4 | 20.8 | 1.0 |
| 30 | V-43 | 49.6 | 1.6 | 25.7 | 4.1 | 35.9 | 1.7 | 3.1 | 1.1 |
| 31 | V-46 | 13.4 | 3.1 | 16.4 | 2.8 | 0.4 | 4.1 | 8.1 | 1.0 |
| 32 | V-47 | 38.3 | 2.5 | 39.9 | 2.3 | -3.0 | 3.8 | 2.8 | 3.9 |
| 33 | V-48 | 47.4 | 5.3 | -0.4 | 3.6 | -1.8 | 6.9 | -2.2 | 6.8 |
| 34 | V-49 | 54.4 | 3.6 | 2.3 | 8.7 | 7.3 | 3.4 | -6.1 | 2.7 |
| 35 | V-50 | 46.9 | 4.9 | 0.4 | 4.5 | 12.9 | 2.4 | 10.2 | 0.9 |
| 36 | V-51 | 35.2 | 1.1 | -0.5 | 1.4 | -6.1 | 7.3 | 1.4 | 5.8 |
| 37 | V-52 | 50.8 | 4.0 | 6.5 | 2.8 | 17.7 | 1.2 | 13.3 | 4.5 |
| 38 | V-53 | 45.7 | 2.1 | -0.3 | 3.9 | 5.1 | 0.5 | 5.4 | 0.7 |
| 39 | V-54 | 10.6 | 5.2 | 0.9 | 3.2 | 11.7 | 0.3 | 15.6 | 0.4 |

TABLE 5-continued

The in vitro proliferation inhibition activity of the compound on Hut-78, PANC-1 cell strains

| | | Hut-78 (inhibition %) | | | | PANC-1 (inhibition %) | | | |
|---|---|---|---|---|---|---|---|---|---|
| No. | Name | 100 μM | SD 100 μM | 10 μM | SD 10 μM | 100 μM | SD 100 μM | 10 μM | SD 10 μM |
| 40 | V-55 | −2.4 | 2.8 | −5.5 | 8.4 | −6.1 | 4.0 | −7.5 | 2.1 |
| 41 | V-60 | 28.5 | 0.9 | 11.8 | 5.2 | 26.1 | 4.0 | 27.3 | 3.0 |
| 42 | V-61 | 44.0 | 2.0 | 2.0 | 9.6 | −2.6 | 1.8 | −9.2 | 0.1 |
| 43 | V-91 | 68.3 | 1.4 | 26.8 | 1.8 | 8.5 | 1.8 | 2.4 | 3.0 |
| 44 | V-92 | 78.5 | 3.3 | 46.2 | 2.6 | 33.3 | 1.9 | 6.3 | 2.4 |
| 45 | V-93 | 64.7 | 2.2 | 27.2 | 8.8 | 16.6 | 1.1 | 9.8 | 2.9 |
| 46 | V-94 | 66.7 | 3.8 | 12.9 | 1.5 | 27.3 | 3.8 | 6.0 | 12.0 |
| 47 | V-95 | 58.0 | 0.4 | 8.0 | 4.7 | 48.7 | 0.5 | 7.0 | 1.2 |
| 48 | V-96 | 41.7 | 2.5 | −0.4 | 6.3 | 64.8 | 60.3 | −0.4 | 13.5 |

TABLE 6

The in vitro proliferation inhibition activity of the compound on Jurkat E6-1, K562 cell strains

| | | Jurkat E6-1 (inhibition %) | | | | K562 (inhibition %) | | | |
|---|---|---|---|---|---|---|---|---|---|
| No | Name | 100 μM | SD 100 μM | 10 μM | SD 10 μM | 100 μM | SD 100 μM | 10 μM | SD 10 μM |
| Positive drug | MS-275 | 96.1 | 0.8 | 89.5 | 1.5 | 74.6 | 2.1 | 66.2 | 1.5 |
| 1 | V-4 | 79.3 | 0.7 | 48.5 | 0.7 | 30.8 | 5.4 | 22.4 | 1.6 |
| 2 | V-5 | 85.9 | 0.3 | 58.5 | 2.1 | 64.4 | 3.7 | 21.0 | 8.0 |
| 3 | V-7 | 96.0 | 0.8 | 27.1 | 2.4 | 85.1 | 1.6 | 51.0 | 4.0 |
| 4 | V-8 | 23.7 | 6.2 | 5.4 | 5.5 | 38.1 | 6.9 | −1.3 | 6.6 |
| 5 | V-9 | 87.9 | 0.9 | 62.2 | 1.8 | 83.2 | 3.0 | 49.4 | 3.0 |
| 6 | V-10 | 93.3 | 2.0 | 27.2 | 3.5 | 87.2 | 2.0 | 53.6 | 2.1 |
| 7 | V-11 | 91.0 | 0.3 | 26.4 | 3.7 | 82.6 | 1.3 | 29.7 | 3.3 |
| 8 | V-12 | 96.3 | 0.2 | 36.4 | 2.2 | 94.5 | 1.0 | 56.9 | 3.0 |
| 9 | V-13 | 22.8 | 1.2 | 0.9 | 3.2 | 30.3 | 1.8 | −2.8 | 7.2 |
| 10 | V-14 | 72.8 | 4.3 | 25.3 | 7.3 | 62.1 | 1.5 | 45.0 | 2.7 |
| 11 | V-15 | 26.3 | 3.5 | 18.6 | 1.7 | 32.3 | 0.2 | 20.4 | 6.8 |
| 12 | V-17 | 87.4 | 2.3 | 25.0 | 7.9 | 69.8 | 2.8 | 49.3 | 2.2 |
| 13 | V-19 | 77.8 | 2.4 | 19.1 | 2.7 | 65.1 | 0.7 | 25.0 | 1.8 |
| 14 | V-20 | 96.5 | 0.2 | 23.8 | 4.3 | 88.7 | 1.4 | 34.0 | 8.4 |
| 15 | V-23 | 13.9 | 4.2 | 33.7 | 3.2 | 11.9 | 8.6 | 27.2 | 0.8 |
| 16 | V-24 | 22.1 | 3.0 | 37.2 | 6.3 | 29.7 | 2.0 | 42.8 | 2.3 |
| 17 | V-25 | 80.2 | 1.5 | 20.3 | 1.9 | 72.4 | 2.3 | 33.6 | 4.2 |
| 18 | V-26 | 95.7 | 0.2 | 76.6 | 1.8 | 87.5 | 2.5 | 58.5 | 7.1 |
| 19 | V-27 | 80.9 | 2.0 | 58.3 | 2.2 | 85.8 | 1.7 | 54.3 | 2.6 |
| 20 | V-28 | 89.4 | 1.6 | 84.8 | 1.5 | 92.9 | 1.6 | 64.3 | 4.9 |
| 21 | V-29 | 89.7 | 0.4 | 49.3 | 2.9 | 85.2 | 2.0 | 52.2 | 2.5 |
| 22 | V-30 | 88.2 | 1.3 | 83.1 | 1.7 | 83.4 | 3.1 | 60.9 | 4.0 |
| 23 | V-34 | 52.7 | 3.5 | 4.7 | 2.3 | 61.2 | 1.4 | 12.8 | 2.3 |
| 24 | V-35 | 91.4 | 2.3 | 30.7 | 3.7 | 75.3 | 2.8 | −1.7 | 7.3 |
| 25 | V-36 | 83.3 | 2.2 | 12.5 | 0.7 | 64.8 | 4.5 | 34.1 | 3.5 |
| 26 | V-38 | 95.1 | 0.8 | 76.9 | 1.4 | 88.2 | 2.1 | 54.0 | 3.8 |
| 27 | V-40 | 87.6 | 0.7 | 31.6 | 2.1 | 75.0 | 3.5 | 45.0 | 2.6 |
| 28 | V-41 | 96.2 | 1.7 | 51.5 | 3.3 | 83.8 | 1.8 | 57.4 | 3.6 |
| 29 | V-42 | 93.7 | 0.3 | 62.4 | 0.9 | 67.7 | 1.5 | 27.9 | 2.3 |
| 30 | V-43 | 96.8 | 1.0 | 69.1 | 0.9 | 60.8 | 0.3 | 13.8 | 1.6 |
| 31 | V-46 | 1.9 | 1.8 | 14.8 | 3.0 | 18.9 | 10.6 | 27.3 | 6.1 |
| 32 | V-47 | 76.6 | 0.7 | 59.4 | 1.1 | 62.1 | 5.7 | 58.0 | 3.4 |
| 33 | V-48 | 61.9 | 2.9 | 9.7 | 2.9 | 57.2 | 2.3 | 20.0 | 6.6 |
| 34 | V-49 | 93.7 | 1.0 | 28.4 | 5.9 | 71.0 | 1.8 | 22.1 | 2.4 |
| 35 | V-50 | 75.9 | 3.0 | 8.9 | 6.0 | 75.7 | 1.4 | 23.8 | 9.0 |
| 36 | V-51 | 42.4 | 4.9 | 14.8 | 3.9 | 53.5 | 2.0 | −2.4 | 1.8 |
| 37 | V-52 | 73.8 | 1.0 | 7.6 | 5.4 | 67.3 | 3.0 | 29.0 | 10.5 |
| 38 | V-53 | 83.5 | 1.8 | 16.9 | 3.7 | 64.9 | 1.2 | 6.6 | 6.1 |
| 39 | V-54 | 5.8 | 4.1 | 2.9 | 5.4 | 13.1 | 10.6 | 12.7 | 10.8 |
| 40 | V-55 | 0.6 | 3.0 | 10.6 | 2.8 | −17.4 | 7.6 | −12.8 | 6.9 |
| 41 | V-60 | 33.3 | 2.8 | 11.0 | 4.9 | 42.7 | 2.3 | 14.6 | 7.3 |
| 42 | V-61 | 90.3 | 0.9 | 21.2 | 3.8 | 62.8 | 2.0 | 7.3 | 13.9 |
| 43 | V-91 | 89.9 | 1.0 | 23.7 | 2.4 | 81.6 | 1.9 | 37.4 | 3.1 |
| 44 | V-92 | 95.5 | 0.8 | 87.5 | 1.5 | 91.1 | 0.5 | 68.7 | 2.3 |
| 45 | V-93 | 93.1 | 0.6 | 23.4 | 3.6 | 67.3 | 2.8 | 23.7 | 4.1 |
| 46 | V-94 | 95.6 | 1.0 | 65.6 | 3.4 | 85.7 | 2.0 | 35.0 | 4.3 |
| 47 | V-95 | 93.8 | 0.7 | 21.6 | 1.9 | 71.9 | 2.5 | 50.6 | 1.4 |
| 48 | V-96 | 83.4 | 0.6 | 15.4 | 4.1 | 61.6 | 0.9 | 41.1 | 2.5 |

TABLE 7

The in vitro proliferation inhibition activity of the compound on A549, MDA-MB-435s cell strains

| | | A549 (inhibition %) | | | | 435s (inhibition %) | | | |
|---|---|---|---|---|---|---|---|---|---|
| NO | Name | 100 μM | SD 100 μM | 10 μM | SD 10 μM | 100 μM | SD 100 μM | 10 μM | SD 10 μM |
| Positive drug | MS-275 | 92.3 | 0.3 | 58.9 | 11.2 | 59.3 | 5.3 | 2.7 | 6.0 |
| 1 | V-4 | 89.7 | 0.8 | 50.6 | 0.9 | 87.5 | 3.0 | 26.7 | 5.4 |
| 2 | V-5 | 84.8 | 1.1 | 65.6 | 1.6 | 86.9 | 1.8 | 35.8 | 1.9 |
| 3 | V-7 | 72.3 | 6.4 | −7.8 | 1.2 | 85.5 | 0.8 | 4.5 | 2.6 |
| 4 | V-8 | −19.4 | 38.8 | −43.9 | 50.0 | −10.4 | 4.7 | −20.7 | 7.6 |
| 5 | V-9 | −13.1 | 14.8 | −44.3 | 44.3 | 84.1 | 8.1 | −14.3 | 5.3 |
| 6 | V-10 | 45.7 | 2.8 | −16.9 | 1.9 | 79.1 | 1.8 | 8.0 | 5.1 |
| 7 | V-11 | 24.9 | 14.0 | −7.4 | 13.4 | 85.4 | 9.2 | −16.5 | 2.8 |
| 8 | V-12 | 38.0 | 60.8 | −5.9 | 2.7 | 94.5 | 0.5 | 14.2 | 4.9 |
| 9 | V-13 | 42.3 | 3.2 | 24.6 | 10.8 | 11.8 | 6.0 | −11.9 | 2.8 |
| 10 | V-14 | 40.1 | 0.3 | −4.4 | 0.6 | 82.9 | 1.4 | 9.4 | 10.1 |
| 11 | V-15 | 12.9 | 6.1 | 15.3 | 8.5 | 42.4 | 1.2 | 30.6 | 7.2 |
| 12 | V-17 | 55.1 | 1.5 | −9.0 | 3.7 | 77.2 | 4.5 | 5.7 | 11.5 |
| 13 | V-19 | 57.1 | 10.3 | 18.3 | 3.0 | 89.1 | 2.0 | 27.5 | 2.9 |
| 14 | V-20 | 72.2 | 1.5 | −17.6 | 1.8 | 63.9 | 1.4 | 19.5 | 3.1 |
| 15 | V-23 | 3.5 | 5.0 | 4.7 | 5.0 | 21.0 | 4.1 | 21.6 | 2.1 |
| 16 | V-24 | 65.7 | 0.2 | 48.7 | 10.9 | 50.4 | 3.2 | 49.8 | 2.6 |
| 17 | V-25 | 67.9 | 3.0 | 29.8 | 5.3 | 73.3 | 3.7 | 32.5 | 8.1 |
| 18 | V-26 | 79.1 | 0.5 | 9.5 | 1.5 | 81.4 | 2.5 | 22.7 | 5.6 |
| 19 | V-27 | 37.3 | 4.1 | 6.3 | 2.9 | 77.0 | 7.7 | 33.0 | 5.5 |
| 20 | V-29 | 41.3 | 3.3 | 0.0 | 5.3 | 57.8 | 4.8 | 17.0 | 7.6 |
| 21 | V-28 | 96.4 | 0.4 | 17.1 | 3.6 | 88.8 | 11.7 | 25.2 | 5.9 |
| 22 | V-30 | 69.9 | 1.3 | 21.8 | 1.6 | 81.4 | 6.6 | 18.0 | 4.6 |
| 23 | V-34 | 6.2 | 6.0 | −7.4 | 11.4 | 42.9 | 6.0 | 21.5 | 4.3 |
| 24 | V-35 | 20.8 | 5.1 | 7.3 | 2.0 | 24.5 | 4.7 | −10.8 | 11.5 |
| 25 | V-36 | 12.0 | 3.9 | 2.4 | 8.0 | 61.2 | 2.2 | 30.8 | 6.5 |
| 26 | V-38 | 63.7 | 1.5 | 4.2 | 5.7 | 73.6 | 5.9 | 16.6 | 3.2 |
| 27 | V-40 | 47.7 | 5.9 | 2.8 | 1.7 | 76.3 | 2.2 | 28.5 | 5.8 |
| 28 | V-41 | 69.8 | 1.2 | 6.3 | 0.9 | 78.5 | 1.7 | 10.1 | 6.3 |
| 29 | V-42 | 88.8 | 1.0 | 56.3 | 0.7 | 89.2 | 1.0 | 24.2 | 6.2 |
| 30 | V-43 | 85.5 | 0.3 | 41.2 | 1.1 | 86.4 | 1.9 | 18.8 | 6.3 |
| 31 | V-46 | 4.1 | 4.6 | 7.7 | 2.2 | 4.1 | 5.8 | 16.4 | 4.1 |
| 32 | V-47 | 8.0 | 0.4 | 9.4 | 2.0 | 29.2 | 3.5 | 21.8 | 5.8 |
| 33 | V-48 | 9.8 | 7.6 | 3.9 | 7.0 | 26.6 | 4.4 | 10.0 | 11.1 |
| 34 | V-49 | 39.9 | 8.0 | −9.5 | 1.7 | 51.9 | 3.3 | 10.3 | 5.4 |
| 35 | V-50 | 14.2 | 3.8 | 8.6 | 2.8 | 36.9 | 5.3 | 14.7 | 3.8 |
| 36 | V-51 | −3.2 | 5.3 | −8.9 | 11.0 | 31.3 | 4.4 | 14.1 | 5.6 |
| 37 | V-52 | 9.9 | 1.5 | 9.8 | 0.1 | 22.8 | 3.1 | 13.9 | 6.1 |
| 38 | V-53 | −1.0 | 0.8 | −6.1 | 3.3 | 38.6 | 6.0 | 9.3 | 6.3 |
| 39 | V-54 | 12.8 | 2.8 | 7.5 | 1.9 | 14.0 | 4.9 | 14.6 | 5.8 |
| 40 | V-55 | −15.3 | 17.6 | −16.5 | 12.5 | 4.9 | 5.2 | 6.5 | 6.4 |
| 41 | V-60 | 12.2 | 2.2 | 3.7 | 0.1 | −3.4 | 4.0 | −7.8 | 5.9 |
| 42 | V-61 | 38.7 | 3.5 | −19.3 | 0.7 | 45.2 | 5.1 | 4.9 | 5.0 |
| 43 | V-91 | 48.9 | 11.3 | 17.7 | 4.6 | 71.2 | 4.0 | 25.9 | 3.1 |
| 44 | V-92 | 54.2 | 44.1 | 2.2 | 9.9 | 77.7 | 2.1 | 23.7 | 7.4 |
| 45 | V-93 | 3.4 | 1.5 | −2.5 | 2.3 | 48.5 | 8.7 | 16.3 | 9.2 |
| 46 | V-94 | 58.4 | 3.6 | 9.1 | 2.5 | 77.0 | 2.1 | 15.1 | 5.2 |
| 47 | V-95 | 48.3 | 3.3 | −12.6 | 5.8 | 72.5 | 1.1 | 4.2 | 12.1 |
| 48 | V-96 | 33.4 | 17.2 | −6.2 | 9.2 | 69.6 | 1.5 | 1.9 | 10.5 |

TABLE 8

The in vitro proliferation inhibition activity of the compound on Hep3B, PC-3 cell strains

| | | Hep3B (inhibition %) | | | | PC-3 (inhibition %) | | | |
|---|---|---|---|---|---|---|---|---|---|
| No | Name | 100 μM | SD 100 μM | 10 μM | SD 10 μM | 100 μM | SD 100 μM | 10 μM | SD 10 μM |
| Positive drug | MS-275 | 52.1 | 0.1 | 10.8 | 7.5 | 71.5 | 0.4 | 12.5 | 3.2 |
| 1 | V-4 | 37.4 | 17.5 | 2.6 | 8.0 | 91.5 | 0.5 | 79.5 | 0.4 |
| 2 | V-5 | 53.6 | 10.4 | 31.2 | 10.4 | 92.4 | 0.8 | 90.3 | 1.2 |
| 3 | V-7 | 59.2 | 3.5 | −12.3 | 6.9 | 36.9 | 2.7 | 0.6 | 8.4 |
| 4 | V-8 | −12.1 | 2.3 | −10.2 | 6.4 | 15.9 | 8.2 | 5.2 | 16.1 |
| 5 | V-9 | 66.6 | 4.2 | 7.3 | 11.3 | 66.7 | 5.8 | 0.0 | 6.6 |
| 6 | V-10 | 57.5 | 10.7 | −7.0 | 24.4 | 56.0 | 12.1 | 23.7 | 4.1 |
| 7 | V-11 | 53.2 | 15.7 | 8.1 | 4.6 | 49.8 | 6.9 | 8.1 | 12.4 |
| 8 | V-12 | 90.4 | 2.6 | 5.0 | 9.9 | 89.3 | 3.2 | 29.7 | 13.2 |
| 9 | V-13 | 26.2 | 7.6 | 27.0 | 11.2 | 19.3 | 5.5 | 5.1 | 8.5 |
| 10 | V-14 | 31.3 | 0.2 | 3.7 | 9.8 | 57.4 | 6.0 | 13.7 | 11.8 |
| 11 | V-15 | 43.0 | 2.5 | 22.3 | 17.7 | 18.8 | 2.1 | 21.9 | 7.5 |
| 12 | V-17 | 67.1 | 10.0 | 4.7 | 26.2 | 61.3 | 7.5 | 25.5 | 22.1 |

TABLE 8-continued

The in vitro proliferation inhibition activity of the compound on Hep3B, PC-3 cell strains

| | | Hep3B (inhibition %) | | | | PC-3 (inhibition %) | | | |
|---|---|---|---|---|---|---|---|---|---|
| No | Name | 100 μM | SD 100 μM | 10 μM | SD 10 μM | 100 μM | SD 100 μM | 10 μM | SD 10 μM |
| 13 | V-19 | 69.8 | 6.4 | 21.5 | 6.0 | 48.5 | 2.5 | −1.9 | 1.3 |
| 14 | V-20 | 79.3 | 2.3 | 7.2 | 11.1 | 84.4 | 2.5 | 22.9 | 8.5 |
| 15 | V-23 | 11.2 | 11.6 | 16.3 | 7.5 | 8.6 | 4.6 | 10.9 | 4.7 |
| 16 | V-24 | 13.5 | 8.5 | 24.8 | 2.0 | 3.4 | 1.4 | 5.1 | 11.2 |
| 17 | V-25 | 45.7 | 0.4 | 18.4 | 9.3 | 67.1 | 4.7 | 41.8 | 7.1 |
| 18 | V-26 | 75.1 | 2.4 | 13.8 | 5.2 | 72.2 | 3.9 | 45.2 | 1.9 |
| 19 | V-27 | 49.9 | 6.9 | 25.4 | 9.5 | 61.0 | 2.9 | 50.2 | 2.0 |
| 20 | V-28 | 60.0 | 6.3 | 23.5 | 5.2 | 75.5 | 0.5 | 48.1 | 2.6 |
| 21 | V-29 | 68.1 | 4.9 | 11.0 | 9.4 | 64.2 | 2.8 | 40.1 | 3.6 |
| 22 | V-30 | 69.2 | 2.8 | 38.3 | 13.8 | 69.0 | 1.3 | 44.6 | 3.9 |
| 23 | V-34 | 28.1 | 10.0 | 1.0 | 2.8 | 40.2 | 14.0 | 7.0 | 1.7 |
| 24 | V-35 | 69.5 | 0.7 | 14.3 | 8.5 | 63.7 | 2.3 | 13.1 | 2.2 |
| 25 | V-36 | 40.6 | 2.8 | 11.3 | 8.1 | 22.1 | 4.7 | −9.4 | 11.8 |
| 26 | V-38 | 63.5 | 3.0 | 11.7 | 7.2 | 52.6 | 0.2 | 8.7 | 7.0 |
| 27 | V-41 | 68.3 | 0.8 | −12.3 | 5.6 | 59.9 | 3.2 | 43.8 | 5.8 |
| 28 | V-43 | 60.5 | 4.0 | 22.5 | 6.6 | 94.5 | 0.5 | 88.0 | 0.8 |
| 29 | V-40 | 51.7 | 26.7 | −5.0 | 0.4 | 38.8 | 9.1 | 6.3 | 7.8 |
| 30 | V-42 | 58.8 | 1.5 | 21.2 | 3.1 | 89.4 | 0.7 | 81.4 | 0.3 |
| 31 | V-46 | −5.0 | 15.4 | 17.5 | 24.0 | −2.4 | 3.0 | −1.7 | 1.5 |
| 32 | V-47 | 19.2 | 15.2 | 11.2 | 24.7 | 12.8 | 8.6 | 7.2 | 9.4 |
| 33 | V-48 | 20.5 | 12.2 | −14.0 | 9.7 | 14.8 | 7.9 | −16.4 | 7.2 |
| 34 | V-49 | 63.4 | 1.5 | 11.0 | 3.6 | 53.8 | 2.8 | 28.3 | 5.3 |
| 35 | V-50 | 23.5 | 26.4 | −0.5 | 19.0 | −3.8 | 1.4 | 5.5 | 2.0 |
| 36 | V-52 | 78.6 | 9.2 | 19.0 | 2.7 | 24.7 | 6.0 | −7.4 | 2.6 |
| 37 | V-54 | 4.7 | 8.2 | 4.2 | 7.1 | 5.9 | 2.3 | 5.6 | 1.5 |
| 38 | V-51 | 26.9 | 14.9 | 24.9 | 11.7 | 45.0 | 2.1 | 21.4 | 14.0 |
| 39 | V-53 | 80.9 | 4.9 | 24.4 | 15.4 | 17.7 | 2.6 | −28.0 | 9.4 |
| 40 | V-55 | 7.2 | 1.3 | 21.7 | 1.2 | 10.9 | 1.8 | 13.3 | 9.8 |
| 41 | V-60 | 31.7 | 2.9 | 9.9 | 11.4 | 8.1 | 11.2 | 1.0 | 1.1 |
| 42 | V-61 | 72.7 | 0.1 | 25.0 | 3.9 | 58.7 | 1.7 | 22.3 | 4.8 |
| 43 | V-91 | 63.6 | 1.4 | 7.8 | 0.2 | 24.2 | 4.5 | 7.9 | 3.2 |
| 44 | V-92 | 80.5 | 0.9 | 20.2 | 3.5 | 73.8 | 1.3 | 41.0 | 5.7 |
| 45 | V-93 | 26.8 | 3.7 | 4.9 | 6.4 | 80.6 | 0.8 | 41.6 | 5.2 |
| 46 | V-94 | 69.4 | 3.0 | 4.5 | 17.0 | 87.8 | 0.7 | 54.2 | 5.9 |
| 47 | V-95 | 72.0 | 6.1 | 16.7 | 12.2 | 80.0 | 0.5 | 30.6 | 18.9 |
| 48 | V-96 | 35.2 | 7.2 | −0.9 | 27.5 | 53.3 | 4.9 | 27.8 | 5.8 |

TABLE 9

The in vitro proliferation inhibition activity of the compound on Colo320 cell strains

| | | Colo320 (inhibition %) | | | |
|---|---|---|---|---|---|
| No | Name | 100 μM | SD 100 μM | 10 μM | SD 10 μM |
| Positive drug | MS-275 | 61.6 | 0.5 | 18.0 | 4.6 |
| 1 | V-4 | 78.3 | 1.2 | 33.2 | 6.4 |
| 2 | V-5 | 92.9 | 12.4 | 39.6 | 1.1 |
| 3 | V-7 | 47.2 | 3.6 | −7.1 | 5.9 |
| 4 | V-8 | 16.8 | 12.2 | 7.1 | 5.0 |
| 5 | V-9 | 45.3 | 2.1 | 13.0 | 4.4 |
| 6 | V-10 | 59.2 | 4.1 | −5.5 | 4.2 |
| 7 | V-11 | 48.5 | 3.2 | 8.9 | 5.4 |
| 8 | V-12 | 86.4 | 0.2 | −1.8 | 2.8 |
| 9 | V-13 | 4.2 | 6.6 | 4.4 | 4.0 |
| 10 | V-14 | 23.3 | 6.0 | 6.4 | 6.3 |
| 11 | V-15 | 4.1 | 4.6 | 2.6 | 4.2 |
| 12 | V-17 | 46.1 | 2.7 | 2.4 | 3.7 |
| 13 | V-19 | 34.3 | 4.1 | 0.9 | 4.0 |
| 14 | V-20 | 82.7 | 18.7 | −14.3 | 4.8 |
| 15 | V-23 | 3.9 | 2.5 | 15.3 | 5.4 |
| 16 | V-24 | −17.1 | 3.2 | −2.3 | 7.9 |
| 17 | V-25 | 28.9 | 4.0 | 4.9 | 7.9 |
| 18 | V-26 | 56.3 | 14.5 | 7.7 | 4.0 |
| 19 | V-27 | 40.1 | 4.6 | 12.9 | 6.1 |
| 20 | V-28 | 58.8 | 19.4 | 6.5 | 2.7 |
| 21 | V-29 | 45.9 | 3.6 | 9.5 | 7.8 |
| 22 | V-30 | 40.8 | 15.8 | 5.4 | 3.8 |
| 23 | V-34 | 5.9 | 4.6 | 7.3 | 7.5 |
| 24 | V-35 | 16.5 | 8.6 | −1.7 | 5.1 |
| 25 | V-36 | 14.1 | 1.0 | 7.9 | 4.2 |
| 26 | V-38 | 44.4 | 11.2 | −0.2 | 6.0 |
| 27 | V-40 | 32.3 | 3.9 | 10.0 | 3.9 |
| 28 | V-41 | 35.5 | 4.1 | −7.2 | 1.0 |
| 29 | V-42 | 77.0 | 2.8 | 26.3 | 20.9 |
| 30 | V-43 | 59.4 | 2.0 | 19.1 | 2.4 |
| 31 | V-46 | −9.0 | 7.5 | 13.7 | 3.8 |
| 32 | V-47 | 6.0 | 2.8 | 11.0 | 4.6 |
| 33 | V-48 | 17.9 | 1.6 | 2.9 | 4.1 |
| 34 | V-49 | 33.8 | 4.2 | −2.5 | 1.0 |
| 35 | V-50 | 27.4 | 6.6 | 6.8 | 5.4 |
| 36 | V-51 | 7.9 | 3.4 | −5.7 | 0.9 |
| 37 | V-52 | 17.7 | 5.2 | 8.0 | 2.4 |
| 38 | V-53 | 18.5 | 1.9 | −8.0 | 6.7 |
| 39 | V-54 | 2.7 | 6.3 | 6.8 | 3.4 |
| 40 | V-55 | −2.8 | 5.3 | −11.2 | 6.7 |
| 41 | V-60 | 2.3 | 3.0 | −5.4 | 6.6 |
| 42 | V-61 | 18.9 | 2.7 | 8.3 | 0.1 |
| 43 | V-91 | 27.6 | 5.1 | 9.6 | 8.2 |
| 44 | V-92 | 65.5 | 1.2 | 6.0 | 2.4 |
| 45 | V-93 | 13.1 | 4.5 | 6.1 | 8.7 |
| 46 | V-94 | 17.8 | 5.0 | −6.4 | 1.0 |
| 47 | V-95 | 68.8 | 3.9 | −1.9 | 4.2 |
| 48 | V-96 | 27.0 | 2.5 | −0.8 | 3.6 |

EXAMPLE 101

| Tablet: | The compound of examples 1-93 | 10 mg |
|---|---|---|
| | Sucrose | 150 mg |
| | Corn starch | 38 mg |
| | Calcium stearate | 2 mg |

The formulation method: the active ingredient is mixed with sucrose and corn starch. The mixture is moistened by adding water, stirred homogeneously, dried, crushed and sieved. Thereto calcium stearate is added, and then the obtained mixture is mixed homogeneously and pressed to be a tablet. Each tablet has a weight of 200 mg and has 10 mg of the active ingredient.

EXAMPLE 102

| Injection: | The compound of examples 1-93 | 20 mg |
|---|---|---|
| | Water for injection | 80 mg |

The formulation method: the active ingredient is dissolved into water for injection, mixed homogenously, and filtrated. The obtained solution is distributed into ampoules under an aseptic condition. Each ampoule contains 10 mg solution and has 2 mg of the active ingredient.

The invention claimed is:

1. A compound selected from:
V-7 N-(2-amino-4-pyridyl)-4-(benzyloxyacylaminomethyl)benzamide;
V-9 N-(2-amino-3-pyridyl)-4-[(4-methylbenzyloxyacyl)aminomethyl]benzamide;
V-10 N-(2-amino-4-pyridyl)-4-[(4-methylbenzyloxyacyl)aminomethyl]benzamide;
V-11 N-(2-amino-3-pyridyl)-4-[(4-methoxybenzyloxyacyl)aminomethyl]benzamide;
V-12 N-(2-amino-4-pyridyl)-4-[(4-methoxybenzyloxyacyl)aminomethyl]benzamide;
V-14 N-(2-amino-4-pyridyl)-4-[(3,4,5-trimethoxybenzyloxyacyl)aminomethyl]benzamide;
V-17 N-(2-amino-4-pyridyl)-4-[(4-nitrobenzyloxyacyl)aminomethyl]benzamide;
V-19 N-(2-amino-3-pyridyl)-4-[(4-fluorobenzyloxyacyl)aminomethyl]benzamide;
V-20 N-(2-amino-4-pyridyl)-4-[(4-fluorobenzyloxyacyl)aminomethyl]benzamide;
V-24 N-(2-amino-4-pyridyl)-4-[(2-naphthylmethoxyacyl)aminomethyl]benzamide;
V-25 N-(2-amino-3-pyridyl)-4-(cinnamoylaminomethyl)benzamide;
V-26 N-(2-amino-4-pyridyl)-4-(cinnamoylaminomethyl)benzamide;
V-27 N-(2-amino-3-pyridyl)-4-[(4-methylcinnamoyl)aminomethyl]benzamide;
V-28 N-(2-amino-4-pyridyl)-4-[(4-methylcinnamoyl)aminomethyl]benzamide;
V-29 N-(2-amino-3-pyridyl)-4-[(4-methoxycinnamoyl)aminomethyl]benzamide;
V-30 N-(2-amino-4-pyridyl)-4-[(4-methoxycinnamoyl)aminomethyl]benzamide;
V-34 N-(2-amino-3-pyridyl)-4-[(3,4,5-trimethoxycinnamoyl)aminomethyl]benzamide;
V-35 N-(2-amino-4-pyridyl)-4-[(3,4,5-trimethoxycinnamoyl)aminomethyl]benzamide;
V-36 N-(2-amino-3-pyridyl)-4-[(4-nitrocinnamoyl)aminomethyl]benzamide;
V-37 N-(2-amino-4-pyridyl)-4-[(4-aminocinnamoyl)aminomethyl]benzamide;
V-38 N-(2-amino-4-pyridyl)-4-[(4-nitrocinnamoyl)aminomethyl]benzamide;
V-40 N-(2-amino-3-pyridyl)-4-[(4-fluorocinnamoyl)aminomethyl]benzamide;
V-41 N-(2-amino-4-pyridyl)-4-[(4-fluorocinnamoyl)aminomethyl]benzamide;
V-47 N-(2-amino-4-pyridyl)-4-(2-naphthylacryloylaminomethyl)benzamide;
V-91 N-(2-amino-3-pyridyl)-4-[(3-methoxycinnamoyl)aminomethyl]benzamide;
V-92 N-(2-amino-4-pyridyl)-4-[(3-methoxycinnamoyl)aminomethyl]benzamide;
V-93 N-(2-amino-3-pyridyl)-4-[(3,4-dimethoxycinnamoyl)aminomethyl]benzamide;
V-94 N-(2-amino-4-pyridyl)-4-[(3,4-dimethoxycinnamoyl)aminomethyl]benzamide;
V-95 N-(2-amino-4-pyridyl)-4-[(3-methoxybenzyloxyacyl)aminomethyl]benzamide or
V-96 N-(2-amino-4-pyridyl)-4-[(3,4-dimethoxybenzyloxyacyl)aminomethyl]benzamide,
or a salt thereof.

2. A composition comprising a therapeutically effective amount of the compound according to claim 1 or a salt thereof and a pharmaceutically acceptable carrier.

3. The compound according to claim 1, wherein the salt is hydrochloride, hydrobromide, sulfate, trifluoroacetate or methanesulfonane.

* * * * *